United States Patent
Grodeland et al.

(10) Patent No.: US 11,780,924 B2
(45) Date of Patent: Oct. 10, 2023

(54) HLA BINDING VACCINE MOIETIES AND USES THEREOF

(71) Applicants: UNIVERSITY OF OSLO, Oslo (NO); NYKODE THERAPEUTICS AS, Oslo (NO)

(72) Inventors: Gunnveig Grodeland, Oslo (NO); Bjarne Bogen, Oslo (NO); Agnete B. Fredriksen, Oslo (NO)

(73) Assignees: UNIVERSITY OF OSLO, Oslo (NO); NYKODE THERAPEUTICS ASA, Oslo (NO)

( * ) Notice: Subject to any disclaimer, the term of this patent is extended or adjusted under 35 U.S.C. 154(b) by 391 days.

(21) Appl. No.: 16/312,337

(22) PCT Filed: Jun. 21, 2017

(86) PCT No.: PCT/IB2017/000946
§ 371 (c)(1),
(2) Date: Dec. 21, 2018

(87) PCT Pub. No.: WO2017/221072
PCT Pub. Date: Dec. 28, 2017

(65) Prior Publication Data
US 2021/0403572 A1    Dec. 30, 2021

Related U.S. Application Data

(60) Provisional application No. 62/352,815, filed on Jun. 21, 2016.

(51) Int. Cl.
| | |
|---|---|
| C07K 16/28 | (2006.01) |
| A61K 39/12 | (2006.01) |
| A61K 39/39 | (2006.01) |
| C07K 16/34 | (2006.01) |
| C07K 16/46 | (2006.01) |
| A61K 39/00 | (2006.01) |

(52) U.S. Cl.
CPC .......... *C07K 16/2833* (2013.01); *A61K 39/00* (2013.01); *A61K 39/12* (2013.01); *A61K 39/39* (2013.01); *C07K 16/34* (2013.01); *C07K 16/46* (2013.01); *C07K 2317/53* (2013.01); *C07K 2317/55* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,057,540 A | 10/1991 | Kensil et al. | |
| 5,225,539 A | 7/1993 | Winter | |
| 6,005,099 A | 12/1999 | Davies et al. | |
| 8,932,693 B2 | 1/2015 | Hoffmann et al. | |
| 2005/0238660 A1 | 10/2005 | Babiuk et al. | |
| 2005/0281843 A1 | 12/2005 | Singh et al. | |
| 2010/0196267 A1 | 8/2010 | Goldenberg et al. | |

FOREIGN PATENT DOCUMENTS

| | | |
|---|---|---|
| EP | 0173494 | 3/1986 |
| EP | 0184187 | 6/1986 |
| EP | 0125023 | 6/1991 |
| EP | 0468520 | 1/1992 |
| EP | 0171496 | 5/1993 |
| EP | 0362279 | 1/1995 |
| EP | 0689454 | 9/1997 |
| EP | 0549074 | 1/1999 |
| EP | 0729473 | 8/2000 |
| GB | 2122204 B | 12/1985 |
| WO | WO 86/01533 | 3/1986 |
| WO | WO 87/02671 | 5/1987 |
| WO | WO 91/00906 | 1/1991 |
| WO | WO 91/10741 | 7/1991 |
| WO | WO 92/03917 | 3/1992 |
| WO | WO 92/03918 | 3/1992 |
| WO | WO 92/19265 | 11/1992 |
| WO | WO 93/13202 | 7/1993 |
| WO | WO 94/00153 | 1/1994 |
| WO | WO 95/17210 | 6/1995 |
| WO | WO 96/02555 | 2/1996 |
| WO | WO 96/11711 | 4/1996 |
| WO | WO 96/33739 | 10/1996 |
| WO | WO 98/16247 | 4/1998 |
| WO | WO 98/56414 | 12/1998 |
| WO | WO 99/10008 | 3/1999 |
| WO | WO 99/11241 | 3/1999 |
| WO | WO 99/12565 | 3/1999 |

(Continued)

OTHER PUBLICATIONS

Metzler et al. 'Solution structure of~uman CTLA-4 and delineation of a CD80/CD86 binding site conserved in CD28.' Nature Structural Biol. 4:527-531, 1997.*
Bork et al. 'Powers and Pitfalls in Sequence Analysis: The 70% Hurdle.' Gen. Res. 10:398-400, 2000.*
Doerks et al. 'Protein annotation: detective work for function prediction.' Trends in Genetics. 14:248-250, 1998.*
Smith et al. The challenges of genome sequence annotation or "the devil is in the details". Nat. Biotech. 15:1222-1223, 1997.*
Brenner S. 'Errors in genome annotation.' Trends in Genetics 15:132-133, 1999.*
Bowie et al. Decipering the Message in Protein Sequences: Tolerance to Amino Acid Substitutions. Science 247:1306-1310, 1990.*

(Continued)

*Primary Examiner* — Nora M Rooney
(74) *Attorney, Agent, or Firm* — Casimir Jones SC; J. Mitchell Jones

(57) ABSTRACT

The present invention relates to an immunoglobulin derived single-chain fragment variable (scFv) that broadly binds HLA II molecules and uses thereof. In particular, targeting of an antigen to antigen presenting cells with the HLAII-specific targeting unit provided herein find use in enhancing immune responses after vaccination.

12 Claims, 18 Drawing Sheets
Specification includes a Sequence Listing.

(56) References Cited

FOREIGN PATENT DOCUMENTS

| WO | WO 08/020079 | 2/2008 |
|---|---|---|
| WO | 2017/034906 | 3/2017 |

OTHER PUBLICATIONS

Hartl et al. 'DNA vaccines for allergy treatment.' Methods 32:328-339, 2004.*
Kuby et al. 'Immunology.' Fourth Edition, Chapter 18:449-465.*
Goel etal. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
MacCallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineers less immunogenic humanzied monoclonal antibody", Journal of Immunology, 2002. vol. 169, pp. 3076-3084.*
International Search Report, International Patent Application No. PCT/IB2017/000946, dated Feb. 6, 2018, 15 pages.
G. Grodeland et al. "The specificity of targeted vaccines for APC surface molecules influences the immune response phenotype" PLOS ones, vol. 8, No. 11, Jan. 1, 2013, pp. e80008-e80008.
G. Grodeland et al. "DNA Vaccine that targets hemagglutinin to MHC Class II Molecules Rapidly induces antibody-mediated protection against influenza" The Journal of Immunology, vol. 191, No. 6, Sep. 15, 2013, pp. 3221-3231.
Fredriksen et al. "DNA Vaccines Increase Immunogenicity of Idiotypic Tumor Antigen by Targeting Novel Fusion Proteins to Antigen-Presenting Cells" Molecular The, Academic Press, US, vo. 13, No. 4, Apr. 1, 2006, pp. 776-785.
Y. Guettinger et al. "A Recombinant Bispecific Single-Chain Fragment Variable Specific for HLA Class II and Fc RI (CD89) . . ." The Journal of Immunology, vol. 184, No. 3, Dec. 30, 2009, pp. 1210-1217.
G. Grodeland et al. "Antigen Targeting to Human HLA Class II Molecules Increases Efficacy of DNA Vaccination" The Journal of Immunology, vol. 197, No. 9, Sep. 26, 2016, pp. 3575-3585.
Al-Lazikani et al., Standard conformations for the canonical structures of immunoglobulins. J Mol Biol. Nov. 7, 1997;273(4):927-48.
Altschul et al., Basic local alignment search tool. J Mol Biol. Oct. 5, 1990;215(3):403-10.
Baier et al., Immunogenic targeting of recombinant peptide vaccines to human antigen-presenting cells by chimeric anti-HLA-DR and anti-surface immunoglobulin D antibody Fab fragments in vitro. J Virol. Apr. 1995;69(4):2357-65.
Baker et al., Electrostatics of nanosystems: application to microtubules and the ribosome. Proc Natl Acad Sci U S A. Aug. 28, 2001;98(18):10037-41.
Batista et al., The who, how and where of antigen presentation to B cells. Nat Rev Immunol. Jan. 2009;9(1):15-27.
Beidler et al., Cloning and high level expression of a chimeric antibody with specificity for human carcinoembryonic antigen. J Immunol. Dec. 1, 1988;141(11):4053-60.
Bergman et al., Development of a xenogeneic DNA vaccine program for canine malignant melanoma at the Animal Medical Center. Vaccine. May 22, 2006;24(21):4582-5.
Better et al., *Escherichia coli* secretion of an active chimeric antibody fragment. Science. May 20, 1988;240(4855):1041-3.

Biragyn et al., Genetic fusion of chemokines to a self tumor antigen induces protective, T-cell dependent antitumor immunity. Nat Biotechnol. Mar. 1999;17(3):253-8.
Blaney et al., Antibody Quality and Protection from Lethal Ebola Virus Challenge in Nonhuman Primates Immunized with Rabies Virus Based Bivalent Vaccine. PLoS Pathogens, 2013; 9(5). E1003389. 14 pages.
Bonifaz et al., Efficient targeting of protein antigen to the dendritic cell receptor DEC-205 in the steady state leads to antigen presentation on major histocompatibility complex class I products and peripheral CD8+ T cell tolerance. J Exp Med. Dec. 16, 2002;196(12):1627-38.
Bork. Powers and pitfalls in sequence analysis: the 70% hurdle. Genome Res. Apr. 2000;10(4):398-400.
Bowie et al., Deciphering the message in protein sequences: tolerance to amino acid substitions. Science,1990; 247 1306-1310.
Brazolot-Millan et al., CpG DNA can induce strong Th1 humoral and cell-mediated immune responses against hepatitis B surface antigen in young mice. Proc Natl Acad Sci U S A. Dec. 22, 1998;95(26):15553-8.
Brenner et al., Errors in genome annotation. Trends Genet. Apr. 1999;15(4):132-3.
Bruggeman et al., Designer mice: the prodDesigner mice: the production of human antibody repertoires in transgenic animals. Year Immunol. 1993;7:33-40.
Bruggemann et al., Human antibody production in transgenic mice: expression from 100 kb of the human IgH locus. Eur J Immunol. May 1991;21(5):1323-6.
Butler et al., Antibody repertoire development in swine. Dev Comp Immunol. 2006;30(1-2):199-221.
Caminschi et al., The dendritic cell subtype-restricted C-type lectin Clec9A is a target for vaccine enhancement. Blood. Oct. 15, 2008;112(8):3264-73.
Cao et al., DNA vaccines targeting the encoded antigens to dendritic cells induce potent antitumor immunity in mice. BMC Immunol. Aug. 14, 2013;14:39.
Carayanniotis et al., Adjuvant-free IgG responses induced with antigen coupled to antibodies against class II MHC. Nature. May 7-13, 1987;327(6117):59-61.
Charalambous et al., Dendritic cell targeting of survivin protein in a xenogeneic form elicits strong CD4+ T cell immunity to mouse survivin. J Immunol. Dec. 15, 2006;177(12):8410-21.
Chothia et al., Canonical structures for the hypervariable regions of immunoglobulins. J Mol Biol. Aug. 20, 1987;196(4):901-17.
Coloma et al., Primer design for the cloning of immunoglobulin heavy-chain leader-variable regions from mouse hybridoma cells using the PCR. Biotechniques. Aug. 1991;11(2):152-4, 156.
Davis et al., CpG DNA is a potent enhancer of specific immunity in mice immunized with recombinant hepatitis B surface antigen. J Immunol. Jan. 15, 1998;160(2):870-6.
Davis et al., West Nile virus recombinant DNA vaccine protects mouse and horse from virus challenge and expresses in vitro a noninfectious recombinant antigen that can be used in enzyme-linked immunosorbent assays. J Virol. May 2001;75(9):4040-7.
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Doerks et al., Protein annotation: detective work for function prediction. Trends Genet. Jun. 1998;14(6):248-50.
Du Pre et al., Tolerance to ingested deamidated gliadin in mice is maintained by splenic, type 1 regulatory T cells. Gastroenterology. Aug. 2011;141(2):610-20, e1-2.
Estrada et al., Intestinal immunization of mice with antigen conjugated to anti-MHC class II antibodies. Vaccine. Jul. 1995;13(10):901-7.
Fossum et al., Vaccine molecules targeting Xcr1 on cross-presenting DCs induce protective CD8+ T-cell responses against influenza virus. Eur J Immunol. Feb. 2015;45(2):624-35.
Fredriksen et al., Chemokine-idiotype fusion DNA vaccines are potentiated by bivalency and xenogeneic sequences. Blood. Sep. 15, 2007;110(6):1797-805.

(56) References Cited

OTHER PUBLICATIONS

Goel et al., Plasticity within the antigen-combining site may manifest as molecular mimicry in the humoral immune response. J Immunol. Dec. 15, 2004;173(12):7358-67.
Green et al., Antigen-specific human monoclonal antibodies from mice engineered with human Ig heavy and light chain YACs. Nat Genet. May 1994;7(1):13-21.
Grodeland et al., Efficient vaccine against pandemic influenza: combining DNA vaccination and targeted delivery to MHC class II molecules. Expert Rev Vaccines. Jun. 2015;14(6):805-14.
Grodeland et al., Polarizing T and B Cell Responses by APC-Targeted Subunit Vaccines. Front Immunol. Jul. 20, 2015;6:367. 7 pages.
Hartl et al., DNA vaccines for allergy treatment. Methods. Mar. 2004;32(3):328-39.
Higgins et al., Fast and sensitive multiple sequence alignments on a microcomputer. Comput Appl Biosci. Apr. 1989;5(2):151-3.
Hilgers et al., Synergistic effects of synthetic adjuvants on the humoral immune response. Int Arch Allergy Appl Immunol. 1986;79(4):392-6.
Hilgers et al., Synthetic sulpholipopolysaccharides: novel adjuvants for humoral immune responses. Immunology. Jan. 1987;60(1):141-6.
Holte et al., Intracellular events associated with inhibition of B cell activation by monoclonal antibodies to HLA class II antigens. Eur J Immunol. Jul. 1989;19(7):1221-5.
Huse et al., Generation of a Large Combinatorial Library of the Immunoglobulin Repertoire in Phage Lambda. Science, 1989; 246(4935):1275-1281.
Janeway et al., The Immune system in Health and disease. Vaccines Chapter 18. Active and passive immunization Designing Vaccines for Active immunizaiton Whole-organism vaccines. Garland Science. 2001. 449-465.
Jardine et al., HIV-1 Vaccines. Priming a broadly neutralizing antibody response to HIV-1 using a germline-targeting immunogen. Science. Jul. 10, 2015;349(6244):156-61.
Jones et al., Replacing the complementarity-determining regions in a human antibody with those from a mouse. Nature. 1986;321(6069):522-5.
Kabat et al, Sequences of Proteins of Immunological Interest,5th Ed., Public Health Service, National Institutes of Health, Bethesda, MD, NIH. 1991. TOC only. 11 pages.
Kacskovics et al., Five putative subclasses of swine IgG identified from the cDNA sequences of a single animal. J Immunol. Oct. 15, 1994;153(8):3565-73.
Kahn et al., Adjustable locks and flexible keys: plasticity of epitope-paratope interactions in germline antibodies. J Immunol. Jun. 1, 2014;192(11):5398-405.
Kawamura et al., Enhancement of antigenic potency in vitro and immunogenicity in vivo by coupling the antigen to anti-immunoglobulin. J Immunol. Jan. 1986;136(1):58-65.
Kensil et al., Separation and characterization of saponins with adjuvant activity from Quillaja saponaria Molina cortex. J Immunol. Jan. 15, 1991;146(2):431-7.
Kensil. Saponins as vaccine adjuvants. Crit Rev Ther Drug Carrier Syst. 1996;13(1-2):1-55.
Kibuuka et al., Safety and immunogenicity of Ebola virus an Marburg virus glycoprotein DNA vaccines assessed separate concomitantly in healthy Ugandan adults: a phase 1b, randomised, double-blind, placebo-controlled clinical trial. Lancet. Apr. 18, 2015;385(9977):1545-54.
Koff et al., Accelerating next-generation vaccine developme global disease prevention. Science. May 31, 2013;340(6136):1232910. 20 pages.
Kohler et al., Continuous cultures of fused cells secreting antibody of predefined specificity. Nature. Aug. 7, 1975;256(5517):495-7.
Lacaille-Dubois et al., A review of the biological and pharmacological activities of saponins. Phytomedicine. Mar. 1996;2(4):363-86.

Lampson et al., Two populations of Ia-like molecules on a human B cell line. J Immunol. Jul. 1980;125(1):293-9.
Larkin et al., Clustal W and Clustal X version 2.0. Bioinformatics. Nov. 1, 2007;23(21):2947-8.
Larrick et al., PCR Amplificaiton of Antibody Genes. Methods: Companion to Methods in Enzymology. 1991; 2:106-110.
Lees et al., Rapid stimulation of large specific antibody responses with conjugates of antigen and anti-IgD antibody. J Immunol. Dec. 1, 1990;145(11):3594-600.
Lefranc et al., IMGT unique numbering for immunoglobulin and T cell receptor variable domains and Ig superfamily V-like domains. Dev Comp Immunol. Jan. 2003;27(1):55-77.
Liu et al., Chimeric mouse-human IgG1 antibody that can mediate lysis of cancer cells. Proc Natl Acad Sci U S A. May 1987;84(10):3439-43.
Liu et al., Production of a mouse-human chimeric monoclonal antibody to CD20 with potent Fc-dependent biologic activity. J Immunol. Nov. 15, 1987;139(10):3521-6.
Logomasini et al., Jet injection devices for the needle-free administration of compounds, vaccines, and other agents. Int J Pharm Compd. Jul.-Aug. 2013;17(4):270-80.
Lonberg et al., Antigen-specific human antibodies from mice comprising four distinct genetic modifications. Nature. Apr. 28, 1994;368(6474):856-9.
Lunde et al., Antibodies engineered with IgD specificity efficiently deliver integrated T-cell epitopes for antigen presentation by B cells. Nat Biotechnol. Jul. 1999;17(7):670-5.
MacCallum et al., Antibody-antigen Interactions: Contact analysis and binding site topography. J. Mol. Biol. 1996;262,732-745.
Maiers et al., High-resolution HLA alleles and haplotypes in the United States population. Hum Immunol. Sep. 2007;68(9):779-88.
Marzi et al., Antibodies are necessary for rVSV/ZEBOV-GP-mediated protection against lethal Ebola virus challenge in nonhuman primates. Proc Natl Acad Sci U S A. Jan. 29, 2013;110(5):1893-8.
Mayer et al., TriFabs—Trivalent IgG-Shaped Bispecific Antibody Derivatives: Design, Generation, Characterization and Application for Targeted Payload Delivery. Int J Mol Sci. Nov. 17, 2015;16(11):27497-507.
McCluskie et al., CpG DNA is a potent enhancer of systemic and mucosal immune responses against hepatitis B surface antigen with intranasal administration to mice. J Immunol. Nov. 1, 1998;161(9):4463-6.
Metzler et al., Solution structure of human CTLA-4 and delineation of a CD80/CD86 binding site conserved in CD28. Nat Struct Biol. Jul. 1997;4(7):527-31.
Mjaaland et al., Modulation of immune responses with monoclonal antibodies. I. Effects on regional lymph node morphology and on anti-hapten responses to haptenized monoclonal antibodies. Eur J Immunol. Jul. 1990;20(7):1457-61.
Morrison et al., Chimeric human antibody molecules: mouse antigen-binding domains with human constant region domains. Proc Natl Acad Sci U S A. Nov. 1984;81(21):6851-5.
Morrison. Transfectomas provide novel chimeric antibodies. Science. Sep. 20, 1985;229(4719):1202-7.
Needleman et al., A general method applicable to the search for similarities in the amino acid sequence of two proteins. J Mol Biol. Mar. 1970;48(3):443-53.
Nepom et al., Critical contribution of beta chain residue 57 in peptide binding ability of both HLA-DR and -DQ molecules. Proc Natl Acad Sci U S A. Jul. 9, 1996;93(14):7202-6.
Nicholas et al., GeneDoc: analysis and visualization of genetic variation. EMBNEW News. 1997. 4 pages.
Nishimura et al., Recombinant human-mouse chimeric monoclonal antibody specific for common acute lymphocytic leukemia antigen. Cancer Res. Feb. 15, 1987;47(4):999-1005.
Norderhaug et al., Versatile vectors for transient and stable expression of recombinant antibody molecules in mammalian cells. J Immunol Methods. May 18, 1997;204(1):77-87.
Ol et al., Chimeric Antibodies. Bio. Techniques, 1986;4:214-221.
Orlandi et al., Cloning immunoglobulin variable domains Cloning immunoglobulin variable domains for expression by the polymerase chain reaction. Proc Natl Acad Sci U S A. May 1989;86(10):3833-7.

(56) References Cited

OTHER PUBLICATIONS

Poosarla et al., Computational de novo design of antibodies binding to a peptide with high affinity. Biotechnol Bioeng. Jun. 2017;114(6):1331-1342.
Powell et al., Vaccine Design—the Subunit and Adjuvant Approach, Plenum Press, New York, 1995. TOC only. 35 pages.
Rice et al., EMBOSS: the European Molecular Biology Open Software Suite. Trends Genet. Jun. 2000;16(6):276-7.
Riechmann et al., Single domain antibodies: comparison of camel VH and camelised human VH domains. J Immunol Methods. Dec. 10, 1999;231(1-2):25-38.
Robinson et al., The IPD and IMGT/HLA database: allele variant databases. Nucleic Acids Res. Jan. 2015;43(Database issue):D423-31.
Roos et al., Optimization of skin electroporation in mice to increase tolerability of DNA vaccine delivery to patients. Mol Ther. Sep. 2009;17(9):1637-42.
Roos et al., Skin electroporation: effects on transgene expression, DNA persistence and local tissue environment. PLoS One. Sep. 30, 2009;4(9):e7226. 10 pages.
Sastry et al., Cloning of the immunological repertoire in *Escherichia coli* for generation of monoclonal catalytic antibodies: construction of a heavy chain variable region-specific cDNA library. Proc Natl Acad Sci U S A. Aug. 1989;86(15):5728-32.
Schjetne et al., A mouse C kappa-specific T cell clone indicates that DC-SIGN is an efficient target for antibody-mediated delivery of T cell epitopes for MHC class II presentation. Int Immunol. Dec. 2002;14(12):1423-30.
Schjetne et al., Cutting edge: link between innate and adaptive immunity: Toll-like receptor 2 internalizes antigen for presentation to CD4+ T cells and could be an efficient vaccine target. J Immunol. Jul. 1, 2003;171(1):32-6.
Schjetne et al., Delivery of antigen to CD40 induces protective immune responses against tumors. J Immunol. Apr. 1, 2007;178(7):4169-76.
Shaw et al., Mouse/human chimeric antibodies to a tumor-associated antigen: biologic activity of the four human IgG subclasses. J Natl Cancer Inst. Dec. 7, 1988;80(19):1553-9.
Silver et al., Structural polymorphism of human DR antigens. Nature. May 31, 1979;279(5712):436-7.
Skea et al., The immunotargeting approach to adjuvant-independent immunization with influenza haemagglutinin. Vaccine. 1993;11(10):994-1002.
Smith et al., The challenges of genome sequence annotation or "the devil is in the details". Nat Biotechnol. Nov. 1997;15(12):1222-3.
Snider et al., Targeted antigen presentation using crosslinked antibody heteroaggregates. J Immunol. Sep. 1, 1987;139(5):1609-16.
Solberg et al., Balancing selection and heterogeneity across the classical human leukocyte antigen loci: a meta-analytic review of 497 population studies. Hum Immunol. Jul. 2008;69(7):443-64.
Soleimanpour et al, APC targeting enhances immunogenicity of a novel multistage Fc-fusion tuberculosis vaccine in mice. Appl Microbiol Biotechnol. Dec. 2015;99(24):10467-80.
Spång et al., Heterodimeric barnase-barstar vaccine molecules: influence of one versus two targeting units specific for antigen presenting cells. PLoS One. 2012;7(9):e45393. 10 pages.
Stanley et al., Chimpanzee adenovirus vaccine generates acute and durable protective immunity against ebolavirus challenge. Nat Med. Oct. 2014;20(10):1126-9.
Staudt et al., Generation of antibody diversity in the immune response of BALB/c mice to influenza virus hemagglutinin. I. Significant variation in repertoire expression between individual mice. J Exp Med. Feb. 1, 1983;157(2):687-704.
Stewart et al., Lentivirus-delivered stable gene silencing by RNAi in primary cells. RNA. Apr. 2003;9(4):493-501.
Sullivan et al., CD8+ cellular immunity mediates rAd5 vaccine protection against Ebola virus infection of nonhuman primates. Nat Med. Aug. 21, 2011;17(9):1128-31.
Sun et al., Chimeric antibody with human constant regions and mouse variable regions directed against carcinoma-associated antigen 17-1A. Proc Natl Acad Sci U S A. Jan. 1987;84(1):214-8.
Tuaillon et al., Human immunoglobulin heavy-chain minilocus recombination in transgenic mice: gene-segment use in mu and gamma transcripts. Proc Natl Acad Sci U S A. Apr. 15, 1993;90(8):3720-4.
Tunheim et al., Human receptors of innate immunity (CD14, TLR2) are promising targets for novel recombinant immunoglobulin-based vaccine candidates. Vaccine. Jun. 11, 2007;25(24):4723-34.
Van Der Linden et al., Induction of immune responses and molecular cloning of the heavy chain antibody repertoire of Lama glama. J. Immunol. Methods 2000; 240: 185-195.
Verhoeyan et al., Reshaping human antibodies: grafting an antilysozyme activity. Science. Mar. 25, 1988;239(4847):1534-6.
Wood et al., The synthesis and in vivo assembly of functional antibodies in yeast. Nature. Apr. 4-10, 1985;314(6010):446-9.
Yelton et al., Use of monoclonal anti-mouse immunoglobulin to detect mouse antibodies. Hybridoma. 1981;1(1):5-11.

\* cited by examiner

QTTSSLSASLGDRVTISCSASQDINNYLNWYQQKPDGTVKLLIYYTSSLH
SGVPSRFSGSGSGTDYSLTISNLEPEDIATYYCQQYSKFPRTFGGGTKLE
IKRGGGGSGGGGSGGGGSQIQLVQSGPELKKPGETVKISCKASGYTFINY
GMNWVKQTPGKGLKWMGWINTYSGEPTYPDDFKGRFAFSLETSASTAYLQ
LNNLKNEDMATYFCARGDYYGPFDNWGQGTTLTVSS
*ELKTPLGDTTHTEPKSCDTPPPCPRCP*
*GGGSSGGGSGGQPREPQVYTLPPSREEMTKNQVSLTCLVKGFYPSDIAVE*
*WESSGQPENNYNTTPPMLDSDGSFFLYSKLTVDKSRWQQGNIFSCSVMHE*
*ALHNRFTQKSLSLSPGKGLGGL**R*
DTICIGYHANNSTDTVDTVLEKNVTVTHSVNLLEDSHNGKLCRLKGIAPLQLGKCNIAG
WLLGNPECDPLLPVRSWSYIVETPNSENGICYPGDFIDYEELREQLSSVSSFERFEIFP
KESSWPNHNTNGVTAACSHEGKSSFYRNLLWLTEKEGSYPKLKNSYVNKKGKEVLVL
WGIHHPPNSKEQQNLYQNENAYVSVVTSNYNRRFTPEIAERPKVRDQAGRMNYYWT
LLKPGDTIIFEANGNLIAPMYAFALSRGFGSGIITSNASMHECNTKCQTPLGAINSSLPY
QNIHPVTIGECPKYVRSAKLRMVTGLRNIPSIQSRGLFGAIAGFIEGGWTGMIDGWYGY
HHQNEQGSGYAADQKSTQNAINGITNKVNTVIEKMNIQFTAVGKEFNKLEKRMENLNK
KVDDGFLDIWTYNAELLVLLENERTLDFHDSNVKNLYEKVKSQLKNNAKEIGNGCFEF
YHKCDNECMESVRNGTYDYPKYSEESKLNREKVDGVKLESMGIYQILAIYSTVASSL (SEQ ID NO:1)

panHLAII-targeting unit:

underline: aHLA-II VL double underline: aHLA-II VH bold: Linker that combines the two fragments of the scFv in the targeting unit

Dimerization unit (for Vaccibody protein) (italics):

italic boxed: Hinge, H1+ H4 italic: CH3 bold R to make the construct more hydrophilic

Influenza hemagglutinin in antigenic unit:

Shaded: CkCk antigen (from X87231)

FIG. 10 (cont'd)

panHLADR-targeting moiety:

<u>DIQMTQSPASLSVSVGETVTITCRASENIYSNLAWYRQKQGKSPQLLVFAASNLADGVPSRFSGSGSGTQYSLKINSLQSEDFGDYYCQHFWTTPWAFGGGTNLEIKR</u>GGGGSGGGGSGGGGS<u>QIQLVQSGPELKKPGETVKISCKASGFTFTN</u>

<u>YGMNWVKQAPGKGLKWMGWINTYTREPTYADDFKGRFAFSLETSASTAYLQINNLKNEDTAKYFCARDITAVVPTGFDYWGQGTTLTVSS</u>

ELKTPLGDTTHTEPKSCDTPPCPRCP

*GGGSSGGGSGGQPREPQVYTLPPSREEMTKNQVSLTCLVKGFYPSDIAVEWESSGQPENNYNTTPPMLDSDGSFFLYSKLTVDKSRWQQGNIFSCSVMHEALHNRFTQKSLSLSPGKGLGGL*R

DTICIGYHANNSTDTVDTVLEKNVTVTHSVNLLEDSHNGKLCRLKGIAPLQLGKCNIAGWLLGNPECDPLLPVRSWSYIVETPNSENGICYPGDFIDYEELREQLSSVSSFERFEIFPKESSWPNHNTNGVTAACSHEGKSSFYRNLLWLTEKEGSYPKLKNSYVNKKGKEVLVLWGIHHPPNSKEQQNLYQNENAYVSVVTSNYNRRFTPEIAERPKVRDQAGRMNYYWTLLKPGDTIIFEANGNLIAPMYAFALSRGFGSGIITSNASMHECNTKCQTPLGAINSSLPYQNIHPVTIGECPKYVRSAKLRMVTGLRNIPSIQSRGLFGAIAGFIEGGWTGMIDGWYGYHHQNEQGSGYAADQKSTQNAINGITNKVNTVIEKMNIQFTAVGKEFNKLEKRMENLNKKVDDGFLDIWTYNAELLVLLENERTLDFHDSNVKNLYEKVKSQLKNNAKEIGNGCFEFYHKCDNECMESVRNGTYDYPKYSEESKLNREKVDGVKLESMGIYQILAIYSTVASSL (SEQ ID NO:2)

panHLADR-targeting unit:

underline: aHLA-DR VL double underline: aHLA-DR VH bold: Linker

Dimerization unit (for Vaccibody protein):

boxed: Hinge, H1+ H4 italic: CH3 bold R to make the construct more hydrophilic

Influenza hemagglutinin in antigenic unit:

shaded: HA

FIG. 11A aHLAII – scFv:

QTTSSLSASLGDRVTISCSASQDINNYLNWYQQKPDGTVKLLIYYTSSLHSGVPSRFSGSGSGTDYSLTISNLEPEDIATYYCQQYSKFPRTFGGGTKLEIKRGGGGSGGGGSGGGGSQIQLVQSGPELKKPGETVKISCKASGYTFINYGMNWVKQTPGKGLKWMGWINTYSGEPTYPDDFKGRFAFSLETSASTAYLQLNNLKNEDMATYFCARGDYYGPFDNWGQGTTLTVSS (SEQ ID NO:3)

Underlined: aHLA-II VL
Shaded: aHLA-II VH
Bold: Linker
Double underlined: CDR regions

FIG. 11B

Light chain of scFv:

Summary Light chain:

CDR1: QDINNYLN (SEQ ID NO:4)
CDR2: LLIYYTSSLHS (SEQ ID NO:5)
CDR3: QQYSKFPRT (SEQ ID NO:6)

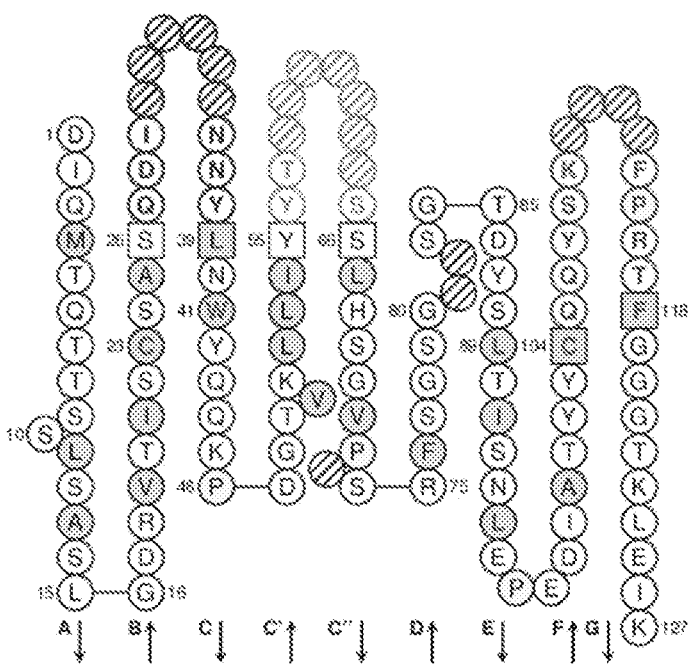

Heavy chain of scFv:

Summary heavy chain:

CDR1: GYTFINYGMN (SEQ ID NO:7)
CDR2: WMGWINTYSGEPTYP (SEQ ID NO:8)
CDR3: RGDYYGPFDN (SEQ ID NO:9)

FIG. 12A aHLA-DR scFv:

*DIQM*
*TQSPASLSVSVGETVTITC*<u>RASENIYSNLA</u>*WYRQKQGKSPQLL*<u>VFAASNL</u>
<u>AD</u>*GVPSRFSGSGSGTQYSLKINSLQSEDFGDYYC*<u>QHFWTTPWA</u>*FGGGTNL*
*EIKR*GGGGSGGGGSGGGGSQIQLVQSGPELKKPGETVKISCKAS<u>GFTFTN</u>
<u>YGMN</u>WVKQAPGKGLKWMG<u>WINTYTREPTYADDFKG</u>RFAFSLETSASTAYL
QINNLKNEDTAKYFC<u>ARDITAVVPTGFDY</u>WGQGTTLTVSS (SEQ ID NO:10)

Underlined: aHLA-DR VL

Shaded: aHLA-DR VH

Bold: Linker

Double underlined: CDR region

FIG. 12B

Light chain of scFv:

Summary Light chain:

CDR1: ENIYSNLA (SEQ ID NO:11)
CDR2: LLVFAASNLAD (SEQ ID NO:12)
CDR3: QHFWTTPWA (SEQ ID NO:13)

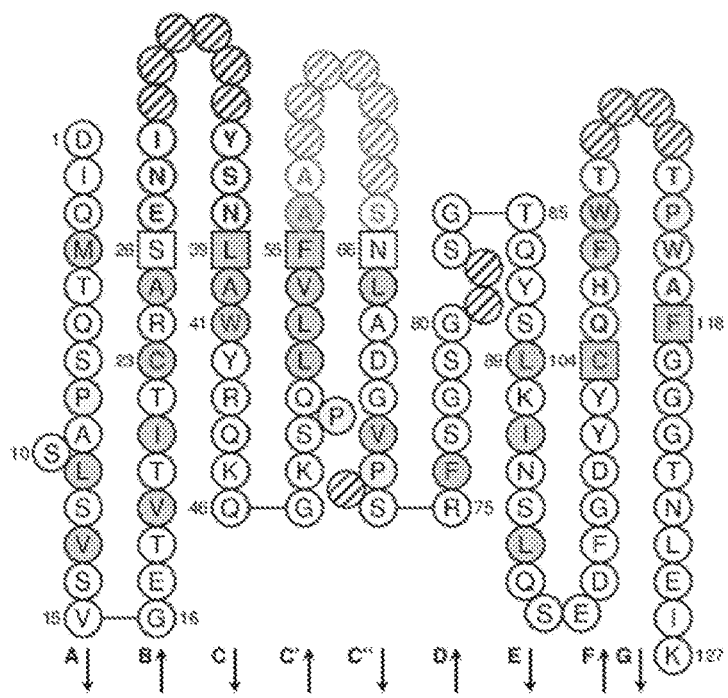

Heavy chain of scFv:

Summary heavy chain:

CDR1: GFTFTNYG (SEQ ID NO:14)
CDR2: WMGWINTYTREPTY (SEQ ID NO:15)
CDR3: ARDITAVVPTGFDY (SEQ ID NO:16)

FIG. 13

| | HKB1 | αpHLAII-CκCκ | αHLADR-CκCκ | αNIP-CκCκ | αMHCII-HA |
|---|---|---|---|---|---|
| rDR0101 | Yes | Yes | Yes | No | No |
| rDR0102 | Yes | Yes | Yes | No | No |
| rDR0103 | Yes | Yes | Yes | No | No |
| rDR0301 | Yes | Yes | Yes | No | No |
| rDR0302 | Yes | Yes | Yes | No | No |
| rDR0401 | Yes | Yes | Yes | No | No |
| rDR0404 | Yes | Yes | Yes | No | No |
| rDR0405 | Yes | Yes | Yes | No | No |
| rDR0701 | Yes | Yes | Yes | No | No |
| rDR0801 | Yes | Yes | Yes | No | No |
| rDR0901 | Yes | Yes | Yes | No | No |
| rDR1001 | Yes | Yes | Yes | No | No |
| rDR1101 | No | No | Yes | No | No |
| rDR1301 | Yes | Yes | Yes | No | No |
| rDR1303 | Yes | Yes | Yes | No | No |
| rDR1401 | Yes | Yes | Yes | No | No |
| rDR1501 | Yes | Yes | Yes | No | No |
| rDR1502 | Yes | Yes | Yes | No | No |
| rDR1601 | Yes | Yes | Yes | No | No |
| rDRB30101 | Yes | Yes | Yes | No | No |
| rDRB30202 | Yes | Yes | Yes | No | No |
| rDRB40101 | Yes | Yes | Yes | No | No |
| rDRB40103 | Yes | Yes | Yes | No | No |
| rDRB50101 | Yes | Yes | Yes | No | No |
| rDRB50202 | Yes | Yes | Yes | No | No |
| rDR0402 | Yes | Yes | Yes | No | No |
| rDR0403 | Yes | Yes | Yes | No | No |
| rDR1201 | Yes | Yes | Yes | No | No |
| rDR0902 | Yes | Yes | Yes | No | No |
| rDR1202 | Yes | Yes | Yes | No | No |
| rDR1602 | Yes | Yes | Yes | No | No |
| rDR1104 | No | No | Yes | No | No |
| rDR1503 | Yes | Yes | Yes | No | No |
| rDR1454 | Yes | Yes | Yes | No | No |
| rDR1402 | Yes | Yes | Yes | No | No |
| rDQ0201 | Yes | Yes | No | No | No |
| rDQ0201 | Yes | Yes | No | No | No |
| C4987DQ0201 | Yes | Yes | No | No | No |
| rDQ0202 | Yes | Yes | No | No | No |
| rDQ0401 | No | No | No | No | No |
| rDQ0402 | No | No | No | No | No |
| C4985DQ0501 | Yes | Yes | No | No | No |
| rDQ0502 | No | No | No | No | No |
| C4986DQ0601 | Yes | Yes | No | No | No |
| rDQ0602 | No | No | No | No | No |
| rDQ0301 | No | No | No | No | No |
| rDQ0301A0201 | No | No | No | No | No |
| C0124DQ0301 | Yes (very low) | No | No | No | No |
| rDQ0302 | No | No | No | No | No |
| rDQ0302 | No | No | No | No | No |
| rDQ0303 | No | No | No | No | No |
| C4952DQ0303 | No | No | No | No | No |

FIG. 13 (cont'd)

| | | | | | |
|---|---|---|---|---|---|
| G8113DQ8301 | Yes | Yes | No | No | No |
| G8191DQ8301 | No | No | No | No | No |
| C4934DQ8302 | No | No | No | No | No |
| C4976DQ8303 | No | No | No | No | No |
| C4107DQ8401 | Yes | Yes | No | No | No |
| rDQ0502 | No | No | No | No | No |
| C4958DQ0503 | Yes | Yes | No | No | No |
| rDQ0604 | Yes | Yes | No | No | No |
| rDQ0302A0201 | No | No | No | No | No |
| rDQ0201 | Yes | Yes | No | No | No |
| rDQ0402 | No | No | No | No | No |
| C4903DQ0609 | Yes | Yes | No | No | No |

| | | | | | |
|---|---|---|---|---|---|
| rDP0101 | Yes | Yes | No | No | No |
| rDP0201 | No | No | No | No | No |
| rDP0301 | No | No | No | No | No |
| rDP0401 | Yes | Yes | No | No | No |
| rDP0402 | No | No | No | No | No |
| rDP0501 | Yes | Yes | No | No | No |
| rDP0601 | No | No | No | No | No |
| rDP1001 | No | No | No | No | No |
| rDP1101 | Yes | Yes | No | No | No |
| rDP1301 | Yes | Yes | No | No | No |
| rDP1401 | No | No | No | No | No |
| rDP1701 | No | No | No | No | No |
| rDP1901 | Yes | Yes | No | No | No |
| rDP1501 | Yes | Yes | No | No | No |
| rDP1801 | No | No | No | No | No |
| rDP2001 | Yes | Yes | No | No | No |
| rDP0101A0103 | Yes | Yes | No | No | No |
| rDP0301A0104 | No | No | No | No | No |
| rDP1601A0104 | No | No | No | No | No |
| rDP1601A0105 | No | No | No | No | No |
| rDP2001A0104 | No | No | No | No | No |
| rDP0301 | Yes | Yes | No | No | No |
| rDP0501 | No | No | No | No | No |
| rDP0301A0201 | No | No | No | No | No |
| rDP1101A0104 | Yes | Yes | No | No | No |
| rDP2001A0202 | No | No | No | No | No |
| rDP1301A0104 | Yes | Yes | No | No | No |

HLA BINDING VACCINE MOIETIES AND USES THEREOF

CROSS-REFERENCE TO RELATED APPLICATIONS

This application is a U.S. 371 national phase entry of International Patent Application No. PCT/IB2017/000946, filed Jun. 21, 2017, which claims priority to U.S. Provisional Patent Application No. 62/352,815, filed Jun. 21, 2016, the contents of which are incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 31,000 Byte ASCII (Text) file named "34866-252_Replacement_ST25.txt" created on Aug. 13, 2021.

FIELD OF THE INVENTION

The present invention relates to an immunoglobulin derived single-chain fragment variable (scFv) that broadly binds HLA II molecules and uses thereof. In particular, targeting of an antigen to antigen presenting cells with the HLAII-specific targeting units provided herein, find use in enhancing immune responses after vaccination.

BACKGROUND OF THE INVENTION

Infectious diseases pose significant threats to the human population. Thus, there is a great need to develop vaccines against pathogens that display considerable variability, and that often have evolved complex mechanisms to evade immune recognition (1). Subunit vaccines are promising in this respect, since they can be constructed to contain antigens and structures that will induce the most relevant type of immune responses. However, a recurrent challenge is the low immunogenicity typically associated with subunit vaccines, whether delivered as DNA, RNA, or protein.

During the second half of the 1980s, targeting of protein antigen to surface molecules on APC was shown to substantially increase immune responses after immunization (4-6). This basic finding was confirmed by later reports (6-15). Initially, these experiments were performed with antigen that had been chemically conjugated to APC-specific antibodies (4, 6, 16). Later, genetic fusion of an APC-specific targeting unit and antigen has been a preferred method (7, 9, 10). Several different versions have been reported, such as Ig-based formats (7, 9, 10), single chain Fv (scFv) formats (17,18) or chemokines (8, 19, 20) as APC-specific targeting units.

The type of immune responses elicited by targeted vaccines are influenced by which surface molecules they bind to on APC (21). This issue is important since most successful vaccines owe their efficacy due to induction of protective antibodies. The best APC target for induction of antibodies so far appears to be MHCII molecules (5, 7, 13, 17, 22, 23).

Novel vaccines are needed to counter many of the complex pathogens of modern times (e.g. influenza, HIV, flavi viruses, tuberculosis, malaria), and antibodies represents a correlate of protection in many disease settings. Thus, targeting of antigen to MHCII molecules could be used to increase the efficacy of subunit vaccination. Such targeting could also reduce the amount of vaccine needed for induction of protective immunity, and the number of vaccine doses necessary. Furthermore, the rapid induction of antibodies after a single MHCII-targeted vaccination could provide a much needed first line defense against a threatening pandemic virus.

Targeting of antigen to MHCII molecules is also likely to be of relevance in therapeutic applications, where increased induction of antibodies with a particular specificity is likely to be beneficial.

SUMMARY OF THE INVENTION

The present invention relates to immunoglobulin derived single-chain fragment variables (scFvs) that broadly binds HLA II molecules, and uses thereof. In particular, targeting of an antigen to antigen presenting cells with the HLAII-specific targeting units provided herein find use in enhancing immune responses after vaccination.

In some embodiments, antigen binding protein that specifically binds to an MHC class II molecule comprises nucleic acid sequences encoding the amino acid sequences SEQ ID NOS: 4 (CDR 1), 5 (CDR 2) and 6 (CDR 3) determining the CDRs of the $V_L$ region, and the amino acid sequences SEQ ID NOS: 7 (CDR 1), 8 (CDR 2) and 9 (CDR 3) determining the CDRs of the $V_H$ region or an immunoglobulin, comprising: the amino acid sequences SEQ ID NOS: 11 (CDR 1), 12 (CDR 2) and 13 (CDR 3) determining the CDRs of the $V_L$ region, and the amino acid sequences SEQ ID NOS: 14 (CDR 1), 15 (CDR 2) and 16 (CDR 3) determining the CDRs of the $V_H$ region.

In some embodiments, the MHC class II molecule is a human HLAII molecule. In some embodiments, the antigen binding protein binds to at least 50 different MHC class II molecules. In some embodiments, the antigen binding protein binds to at least 100 different MHC class II molecules. In some embodiments, the antigen binding protein binds to MHC class II molecules from at least 5 different species of animals.

In some embodiments, antigen binding protein that specifically binds to an MHC class II molecule comprises nucleic acid sequences encoding the amino acid sequences SEQ ID NOS: 4 (CDR 1), 5 (CDR 2) and 6 (CDR 3) determining the CDRs of the $V_H$ region, and the amino acid sequences SEQ ID NOS: 7 (CDR 1), 8 (CDR 2) and 9 (CDR 3) determining the CDRs of the $V_L$ region or an immunoglobulin, comprising: the amino acid sequences SEQ ID NOS: 11 (CDR 1), 12 (CDR 2) and 13 (CDR 3) determining the CDRs of the $V_H$ region, and the amino acid sequences SEQ ID NOS: 14 (CDR 1), 15 (CDR 2) and 16 (CDR 3) determining the CDRs of the $V_L$ region.

In some embodiments, molecule of interest is an antigen. In some embodiments, molecule of interest comprises at least two distinct antigens. In some embodiments, the molecule of interest is an antigen derived from a pathogenic microorganism. In some embodiments, pathogenic microorganism is influenza virus or ebola virus. In some embodiments, the antigen is influenza hemagglutinin (HA), preferably H1, H2, H3, H5, H7 or H9.

In some embodiments, the nucleic acid further encodes a linker sequence between said immunoglobulin and said molecule of interest. In some embodiments, the linker sequence may be from about 5 to about 10, 20, 30, 40, or 50 amino acids in length. In some embodiments, the linker comprises a dimerization unit comprising a hinge region from an immunoglobulin and an immunoglobulin constant region. In some embodiments, the linker is a dimerization unit derived from a natural protein.

In some embodiments, the present invention provides a vaccine or pharmaceutical composition, comprising: a nucleic acid as described above and a pharmaceutically acceptable carrier. In some embodiments, the pharmaceutically acceptable carrier is saline or other physiologically acceptable solution. In some embodiments, the pharmaceutically acceptable carrier is a particle, such as a gold particle, suitable for use in a gene gun. In some embodiments, the composition further comprises an adjuvant.

In some embodiments, the present invention provides for use of the compositions or nucleic acids described above to induce an immune response against an antigen in a subject. In some embodiments, the present invention provides for use of the compositions or nucleic acids described above to treat or prevent infection by a pathogenic microorganism.

In some embodiments, the present invention provides methods of inducing an immune response, comprising: administering the composition or nucleic acid as described above to a subject under conditions such that said subject elicits an immune response to said molecule of interest. In some embodiments, the present invention provides methods treating or preventing infection by a pathogenic microorganism, comprising: administering the composition or nucleic acids described above to a subject under conditions such that said subject elicits an immune response to said molecule of interest.

In further embodiments, the present invention provides an MHC Class II (e.g., human HLAII) directing vaccine moiety (e.g., scFV, Fab, antigen binding domain, antibody fragment, or immunoglobulin) fused to or in operable association with a molecule of interest. In some embodiments, the MHC class II targeting moiety is a pan-specific MHC class II targeting molecule that binds to a plurality of different MHC class II molecules (e.g., at least 20, 30, 40, 50, 60, 70, 80, 90, 100 or more different MHC class II molecules). In some embodiments, the MHC class II targeting molecule binds to MHC class II molecule of a plurality of species of animals (e.g., at least 2, 3, 4, 5, 6, 7, 8, 9, 10 or more species) of both human, small mammals, and large mammals.

In some embodiments, the targeting moiety (e.g., antigen binding domain is an immunoglobulin comprising: the amino acid sequences SEQ ID NOS: 4 (CDR 1), 5 (CDR 2) and 6 (CDR 3) determining the CDRs of the $V_L$ region, and the amino acid sequences SEQ ID NOS: 7 (CDR 1), 8 (CDR 2) and 9 (CDR 3) determining the CDRs of the $V_H$ region or an immunoglobulin, comprising: the amino acid sequences SEQ ID NOS: 11 (CDR 1), 12 (CDR 2) and 13 (CDR 3) determining the CDRs of the $V_L$ region, and the amino acid sequences SEQ ID NOS: 14 (CDR 1), 15 (CDR 2) and 16 (CDR 3) determining the CDRs of the $V_H$ region.

In some embodiments, the targeting moiety is directly linked to an antigen (e.g., in the form of a fusion protein or nucleic acids encoding a fusion protein). In some embodiments, the targeting moiety is connected to an antigen via a multimerization unit (e.g., in the form of a dimerization unit securing bivalent display of the invention as well as the antigens; a trimerization domain securing trivalent display of antigens and the invention; or any multimerization units aiming at multivalent display of vaccine antigens, the invention, or both). In some embodiments, the composition is a fusion protein comprising one antigen binding protein in operable association with one distinct molecule of interest. In some embodiments, the composition is a fusion protein comprising one antigen binding protein in operable association with at least two distinct molecules of interest. In some embodiments, the composition is a fusion protein comprising at least two distinct antigen binding proteins in operable association with one distinct molecule of interest. In some embodiments, the composition comprises a dimerized or multimerized molecule comprising two of said fusion proteins, wherein each of said fusion proteins comprises the same or distinct antigen binding proteins and molecules of interest.

The present invention is not limited to display of the MHC Class II-specific targeting unit as a single chain fragment variable. In some embodiments, the targeting unit is inserted into a vaccine format in the form of an immunoglobulin or antibody fragment (e.g., Fab fragment), or as a full-length immunoglobulin.

Further embodiments provide a vaccine or pharmaceutical composition, comprising: any of the targeting units, fusion proteins or nucleic acids displaying either of the targeting units described herein, and a pharmaceutically acceptable carrier. In some embodiments, the composition further comprises an adjuvant.

Additional embodiments provide the use of the vaccine composition of claim to induce an immune response against an antigen in a subject and/or treat or prevent infection by a pathogenic microorganism.

Yet other embodiments provide a method of inducing an immune response and/or treating or preventing infection by a pathogenic microorganism, comprising: administering the vaccine composition to a subject under conditions such that the subject elicits an immune response to said molecule of interest.

Additional embodiments are described herein.

BRIEF DESCRIPTION OF THE DRAWINGS

FIG. 7. Antibody titers against ebola antigen in guinea pigs. IgG antibody titers specific to ZEBOV-GP in guinea pig sera. Two groups of six female Hartley guinea pigs each were immunized twice at a three-week interval with αHLAII-GP, via either electroporation (group A,) or squares). EBOV-GP-specific IgG antibody responses were detected using an in-house ELISA and log 10-transformed titers were calculated by linear regression. Two-way ANOVA tests were performed to determine statistical significance between groups at different time points, where $p<0.0001$ is indicated by four asterisks (****).

FIG. 8A-B. ZEBOV-GP-specific IgA antibody titers in guinea pig sera and saliva. Two groups of six female Hartley guinea pigs each were immunized twice at a three week interval with αHLAII-GP, via either electroporation (group A) or needle-free jet injection (group B). EBOV-GP-specific IgA antibody responses were detected using an in-house ELISA with sera (A) or saliva (B). Results are presented as log 10-transformed titers calculated by linear regression (A) or OD values at 1:5 dilution (B). Negative controls from guinea pigs immunized intraperitoneally with a non-relevant protein are shown where DO samples were missing. Two-way ANOVA tests were performed to determine statistical significance at different time points compared to day 0 or negative controls, where $p≤0.01$ or $p<0.0001$ is indicated by two () or four (**) asterisks, respectively.

FIG. 10. Sequence of exemplary fusion constructs of embodiments of the present invention.

FIG. 11A-B. Sequence and structure of aHLAII-scFv.

FIG. 12A-B. Sequence and structure of aHLA-DR scFv.

FIG. 13. Binding of vaccine proteins to HLA II-coated beads. The indicated purified vaccine proteins and IgM mAb from the hybridoma HKB1 were assayed for binding to 91 different beads coated with either HLA-DR, HLA-DQ or HLA-DP molecules as indicated.

DEFINITIONS

Figure 1:
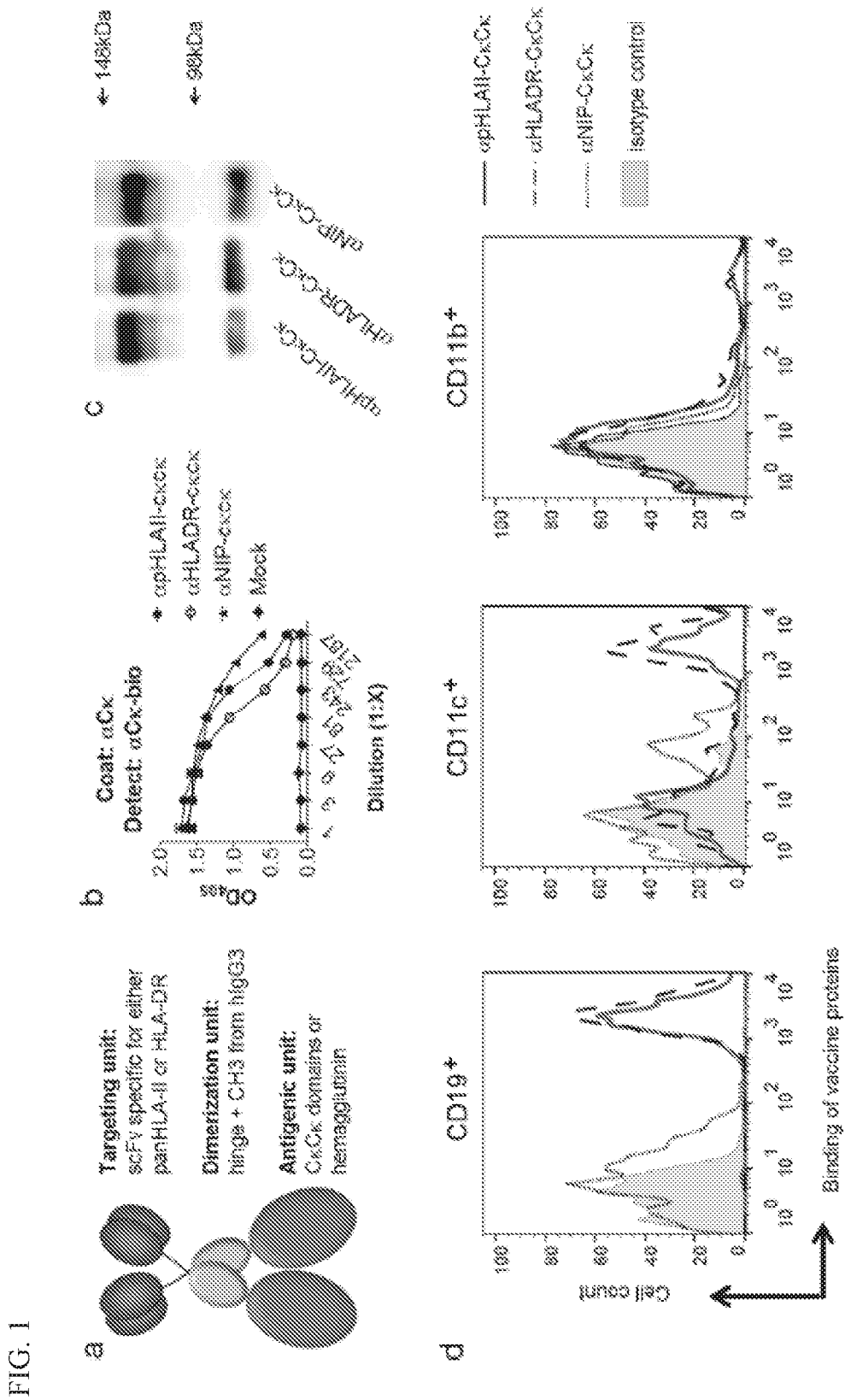
FIG. 1A-D. Characterization of vaccine proteins. (a) Schematic structure of a dimeric vaccine protein. The vaccine consists of two N-terminal HLA-specific targeting units in a scFv format that are linked to an Ig-based dimerization unit and two C-terminal antigenic units. (b) Vaccine proteins in supernatants from 293E cells transiently transfected with DNA constructs were examined in Sandwich ELISA. (c) Western blot of affinity purified vaccine proteins detected with mAb against human CH3 dimerization unit. The vaccine proteins are indicated below lanes, MW by arrows. d) FACS analyses of human PBMC stained with the indicated vaccine proteins. Binding to gated CD19+, CD11c+ and CD11b+ cells are shown.

A used herein, the terms "targeting moiety" and "targeting molecule" refer to molecules (e.g., antibodies or antibody fragments) that target a composition (e.g., a composition comprising a fusion protein or complex of a targeting moiety and a molecule of interest) to a target (e.g., a MHC class II molecule).

The term "antibody" and "immunoglobulin" are used herein are used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity. Also included are antibody fragments having an Fc region, and fusion proteins that comprise a region equivalent to the Fc region of an immunoglobulin.

An "antibody fragment" or "immunoglobulin fragment" are used interchangeably and refer to a molecule other than an intact antibody that comprises a portion of an intact antibody that binds the antigen to which the intact antibody binds. Examples of antibody fragments include but are not limited to Fv, Fab, Fab', Fab'-SH, F(ab').sub.2, single-chain antibody molecules (e.g. scFv), diabodies, and multispecific antibodies formed from antibody fragments.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Effector functions" are used herein refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; cytokine secretion; immune-complex-mediated antigen uptake by antigen presenting cells; down regulation of cell surface receptors (e.g. B cell receptor); and B cell activation. The term "wildtype" when used in reference to a protein refers to proteins encoded by the genome of a cell, tissue, or organism, other than one manipulated to produce synthetic proteins.

The term "antigen binding domain" refers to the part of an antigen binding molecule (e.g., antigen binding protein) that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH). In some embodiments, an antigen binding domains comprise "complementarity determining regions" (CDRS) of the variable regions.

The term "chimeric" antibody refers to an antibody in which a portion of the heavy and/or light chain is derived from a particular source or species, while the remainder of the heavy and/or light chain is derived from a different source or species. For chimeric antibodies, for example, the non-antigen binding components may be derived from a wide variety of species, including primates such as chimpanzees and humans. Humanized antibodies are a particularly preferred form of chimeric antibodies.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, β, δ, ε, γ, and μ.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

"Framework" or "FR" refers to variable domain residues other than hypervariable region (HVR) (or CDR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., J. Mol. Biol. 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The term "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; unnatural amino acids like p-aminophenylalanine, a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on). For an amino acid substitution, the following nomenclature is used: Original amino acid, position, substituted amino acid. Accordingly, the substitution of lysine with alanine at position 573 is designated as "K573A" and the substitution of lysine with proline at position 573 is designated as K573P. Multiple mutations are separated by addition marks ("+") or "/", e.g., "Gly205Arg+Ser411Phe" or "G205R/S411F", representing mutations at positions 205 and 411 substituting glycine (G) with arginine (R), and serine (S) with phenylalanine (F), respectively.

The relatedness between two amino acid sequences or between two nucleotide sequences is described by the parameter "identity". For purposes of the present invention, the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The optional parameters 11644.000-EP7 used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows: (Identical Residues×100)/(Length of Alignment−Total Number of Gaps in Alignment).

The expression "amino acid position corresponding to" a position in a reference sequence and similar expression is intended to identify the amino acid residue that in the primary or spatial structure corresponds to the particular position in the reference sequence. The skilled person will appreciate that this can be done by aligning a given sequence with the reference sequence and identifying the amino acid residue that aligns with the particular position in the reference sequence.

The expression Xnnn is intended to mean an amino acid residue X located in a position corresponding to position nnn in HSA and the expression XnnnY is intended to mean a substitution of any amino acid X located in a position corresponding to position nnn in HSA with the amino acid residue Y.

As used herein, the term "affinity" refers to a measure of the strength of binding between two members of a binding pair, for example, an immunoglobulin and antigen. $K_d$ is the dissociation constant and has units of molarity. The affinity constant is the inverse of the dissociation constant. An affinity constant is sometimes used as a generic term to describe this chemical entity. It is a direct measure of the energy of binding. The natural logarithm of K is linearly related to the Gibbs free energy of binding through the equation $\Delta G_0 = -RT \ LN(K)$ where R=gas constant and temperature is in degrees Kelvin. Affinity may be determined experimentally, for example by surface plasmon resonance (SPR) using commercially available Biacore SPR units (GE Healthcare).

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) and/or portion or component thereof (e.g., a protein antigen)) that is capable of eliciting an immune response in a subject. In some embodiments, immunogens elicit immunity against the immunogen (e.g., microorganism (e.g., pathogen or a pathogen product)).

As used herein, the term "vaccine" refers to any composition that generates and "immune response" that results in "immunity" (e.g., to an immunogen). In some embodiments, vaccines comprise a fusion protein or nucleic acid encoding a fusion protein that comprises a MHC II targeting molecule and a molecule of interest.

The term "sample" as used herein is used in its broadest sense. As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The present invention relates to MHC class II binding immunoglobulins and uses thereof. In particular, provided herein are MHC class II binding antibodies and fragments and uses thereof (e.g., in vaccines).

Embodiments of the present invention provide fusion proteins and nucleic acids encoding fusion proteins (e.g., DNA, RNA, or protein vaccines) or molecules comprising an immunoglobulin or fragment thereof that specifically binds to an MHC class II molecule and a molecule of interest (e.g., antigen). In some embodiments, the MHC class II targeting moiety is a pan-specific MHC class II targeting molecules that binds to a plurality of different MHC class II molecules (e.g., at least 20, 30, 40, 50, 60, 70, 80, 90, 100 or more different MHC class II molecules). In some embodiments, the MHC class II targeting molecule binds to MHC class II molecule of a plurality of species of animals (e.g., at least 2, 3, 4, 5, 6, 7, 8, 9, 10 or more species) of both human, small mammals, and large mammals.

L. MHC class II Targeting Entities

The present invention is not limited to the use of any particular MHC class II targeting entity (e.g., antigen binding protein) and the targeting entity may take the form of a full length immunoglobulin or fragment thereof as well as engineered molecules such as single chain antibodies. In some embodiments, the MHC class II-targeting entity is a scFv fragment derived from a monoclonal antibody. In some embodiments, the fusion protein encoded by a nucleic acid of the present invention comprises the MHC class II-specific targeting unit in the form of an antibody fragment, such as a Fab fragment, or a full-length immunoglobulin.

Constructs described herein utilize fusions or nucleic acids encoding fusions of at least a portion of an immunoglobulin fused to a molecule of interest.

In general, an immunoglobulin molecule is composed of two identical heavy and two identical light polypeptide chains, held together by interchain disulfide bonds. Each individual light and heavy chain folds into regions of about 110 amino acids, assuming a conserved three-dimensional conformation. The light chain comprises one variable region (termed VL) and one constant region (CL), while the heavy chain comprises one variable region (VH) and three constant regions (CH1, CH2 and CH3). Pairs of regions associate to form discrete structures. In particular, the light and heavy chain variable regions, VL and VH, associate to form an "FV" area that contains the antigen-binding site.

The variable regions of both heavy and light chains show considerable variability in structure and amino acid composition from one antibody molecule to another, whereas the constant regions show little variability. Each antibody recognizes and binds an antigen through the binding site defined by the association of the heavy and light chain, variable regions into an FV area. The light-chain variable region VL and the heavy-chain variable region VH of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDRs from a light chain and the three CDRs from a corresponding heavy chain form the antigen-binding site.

The amino acid sequences of many immunoglobulin heavy and light chains have been determined and reveal two important features of antibody molecules. First, each chain consists of a series of similar, although not identical, sequences, each about 110 amino acids long. Each of these repeats corresponds to a discrete, compactly folded region of protein structure known as a protein domain. The light chain is made up of two such immunoglobulin domains, whereas the heavy chain of the IgG antibody contains four.

The second important feature revealed by comparisons of amino acid sequences is that the amino-terminal sequences of both the heavy and light chains vary greatly between different antibodies. The variability in sequence is limited to approximately the first 110 amino acids, corresponding to the first domain, whereas the remaining domains are constant between immunoglobulin chains of the same isotype. The amino-terminal variable or V domains of the heavy and light chains ($V_H$ and $V_L$, respectively) together make up the V region of the antibody and confer on it the ability to bind specific antigen, while the constant domains (C domains) of the heavy and light chains (CH and CL, respectively) make up the C region. The multiple heavy-chain C domains are numbered from the amino-terminal end to the carboxy terminus, for example $C_H1$, $C_H2$, and so on.

The protein domains described above associate to form larger globular domains. Thus, when fully folded and assembled, an antibody molecule comprises three equal-sized globular portions joined by a flexible stretch of polypeptide chain known as the hinge region. Each arm of this Y-shaped structure is formed by the association of a light chain with the amino-terminal half of a heavy chain, whereas the trunk of the Y is formed by the pairing of the carboxy-terminal halves of the two heavy chains. The association of the heavy and light chains is such that the $V_H$ and $V_L$ domains are paired, as are the $C_H1$ and $C_L$ domains. The $C_H3$ domains pair with each other but the $C_H2$ domains do not interact; carbohydrate side chains attached to the $C_H2$ domains lie between the two heavy chains. The two antigen-binding sites are formed by the paired $V_H$ and $V_L$ domains at the ends of the two arms of the Y.

Proteolytic enzymes (proteases) that cleave polypeptide sequences have been used to dissect the structure of antibody molecules and to determine which parts of the molecule are responsible for its various functions. Limited digestion with the protease papain cleaves antibody molecules into three fragments. Two fragments are identical and contain the antigen-binding activity. These are termed the Fab fragments, for Fragment antigen binding. The Fab fragments correspond to the two identical arms of the antibody molecule, which contain the complete light chains paired with the $V_H$ and $C_H1$ domains of the heavy chains. The other fragment contains no antigen-binding activity but was originally observed to crystallize readily, and for this reason was named the Fc fragment, for Fragment crystallizable. This fragment corresponds to the paired $C_H2$ and $C_H3$ domains and is the part of the antibody molecule that interacts with effector molecules and cells. The functional differences between heavy-chain isotypes lie mainly in the Fc fragment. The hinge region that links the Fc and Fab portions of the antibody molecule is in reality a flexible tether, allowing independent movement of the two Fab arms, rather than a rigid hinge.

Throughout this disclosure, reference is made to the numbering system from Kabat, E. A., et al., Sequences of Proteins of Immunological Interest (National Institutes of Health, Bethesda, Md. (1987) and (1991). In these compendiums, Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. The Kabat numbering scheme is followed in this description. For purposes of this invention, to assign residue numbers to a candidate antibody amino acid sequence which is not included in the Kabat compendium, one follows the following steps. Generally, the candidate sequence is aligned with any immunoglobulin sequence or any consensus sequence in Kabat. Alignment may be done by hand, or by computer using commonly accepted computer programs; an example of such a program is the Align 2 program. Alignment may be facilitated by using some amino acid residues which are common to most Fab sequences. For example, the light and heavy chains each typically have two cysteines which have the same residue numbers; in $V_L$ domain the two cysteines are typically at residue numbers 23 and 88, and in the $V_H$ domain the two cysteine residues are typically numbered 22 and 92. Framework residues generally, but not always, have approximately the same number of residues, however the CDRs will vary in size. For example, in the case of a CDR from a candidate sequence which is longer than the CDR in the sequence in Kabat to which it is aligned, typically suffixes are added to the residue number to indicate the insertion of additional residues. For candidate sequences which, for example, align with a Kabat sequence for residues 34 and 36 but have no residue between them to align with residue 35, the number 35 is simply not assigned to a residue.

Monoclonal antibodies against HLA II targets for use in the fusion proteins described herein are produced by a variety of techniques including conventional monoclonal antibody methodologies such as the somatic cell hybridization techniques of Kohler and Milstein, Nature, 256:495 (1975). Although in some embodiments, somatic cell hybridization procedures are preferred, other techniques for producing monoclonal antibodies are contemplated as well (e.g., viral or oncogenic transformation of B lymphocytes). The preferred animal system for preparing hybridomas is the murine system.

Hybridoma production in the mouse is a well-established procedure. Immunization protocols and techniques for isolation of immunized splenocytes for fusion are known in the art. Fusion partners (e.g., murine myeloma cells) and fusion procedures are also known. Human monoclonal antibodies (mAbs) directed against human proteins can be generated using transgenic mice carrying the complete human immune system rather than-the mouse system. Splenocytes from the transgenic mice are immunized with the antigen of interest, which are used to produce hybridomas that secrete human mAbs with specific affinities for epitopes from a human protein. (See e.g., Wood et al., WO 91/00906, Kucherlapati et al., WO 91/10741; Lonberg et al., WO 92/03918; Kay et al., WO 92/03917 [each of which is herein incorporated by reference in its entirety]; N. Lonberg et al., Nature, 368: 856-859 [1994]; L. L. Green et al., Nature Genet., 7:13-21 [1994]; S. L. Morrison et al., Proc. Nat. Acad. Sci. USA, 81:6851-6855 [1994]; Bruggeman et al., Immunol., 7:33-40 [1993]; Tuaillon et al., Proc. Nat. Acad. Sci. USA, 90:3720-3724 [1993]; and Bruggeman et al. Eur. J. Immunol., 21:1323-1326 [1991]).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies. (See e.g., Sastry et al., Proc. Nat. Acad. Sci. USA, 86:5728 [1989]; Huse et al., Science, 246:1275 [1989]; and Orlandi et al., Proc. Nat. Acad. Sci. USA, 86:3833 [1989]). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and the PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies. (See e.g., Larrick et al., Biotechniques, 11:152-156 [1991]). A similar strategy can also be used to amplify human heavy and light chain variable regions from human antibodies (See e.g., Larrick et al., Methods: Companion to Methods in Enzymology, 2:106-110 [1991]).

Chimeric mouse-human monoclonal antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 [each of which is herein incorporated by reference in its entirety]; Better et al., Science, 240:1041-1043 [1988]; Liu et al., Proc. Nat. Acad. Sci. USA, 84:3439-3443 [1987]; Liu et al., J. Immunol., 139:3521-3526 [1987]; Sun et al., Proc. Nat. Acad. Sci. USA, 84:214-218 [1987]; Nishimura et al., Canc. Res., 47:999-1005 [1987]; Wood et al., Nature, 314:446-449 [1985]; and Shaw et al., J. Natl. Cancer Inst., 80:1553-1559 [1988]).

The chimeric antibody can be further humanized by replacing sequences of the Fv variable region that are not directly involved in antigen binding with equivalent sequences from human Fv variable regions. General reviews of humanized chimeric antibodies are provided by S. L. Morrison, Science, 229:1202-1207 (1985) and by Oi et al., Bio. Techniques, 4:214 (1986). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPIIbIIIa antibody producing hybridoma. The recombinant DNA encoding the chimeric antibody, or fragment thereof, can then be cloned into an appropriate expression vector.

Suitable humanized antibodies can alternatively be produced by CDR substitution (e.g., U.S. Pat. No. 5,225,539 (incorporated herein by reference in its entirety); Jones et al., Nature, 321:552-525 [1986]; Verhoeyan et al., Science, 239:1534 [1988]; and Beidler et al., J. Immunol., 141:4053 [1988]). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs; using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In some embodiments, the monoclonal antibody is a murine antibody or a fragment thereof. In other preferred embodiments, the monoclonal antibody is a bovine antibody or a fragment thereof. For example, the murine antibody can be produced by a hybridoma that includes a B cell obtained from a transgenic mouse having a genome comprising a heavy chain transgene and a light chain transgene fused to an immortalized cell. The antibodies can be of various isotypes, including, but not limited to: IgG (e.g., IgG1, IgG2, IgG2a, IgG2b, IgG2c, IgG3, IgG4); IgM; IgA1; IgA2; IgAsec; IgD; and IgE. In some preferred embodiments, the antibody is an IgG isotype. In other preferred embodiments, the antibody is an IgM isotype. The antibodies can be full-length (e.g., an IgG1, IgG2, IgG3, or IgG4 antibody) or can include only an antigen-binding portion (e.g., a Fab, F(ab')2, Fv or a single chain Fv fragment).

In preferred embodiments, the immunoglobulin is a recombinant antibody (e.g., a chimeric or a humanized antibody), a subunit, or an antigen binding fragment thereof (e.g., has a variable region, or at least a complementarity determining region (CDR)).

In some embodiments, the immunoglobulin is monovalent (e.g., includes one pair of heavy and light chains, or antigen binding portions thereof). In other embodiments, the immunoglobulin is a divalent (e.g., includes two pairs of heavy and light chains, or antigen binding portions thereof). In some embodiments, antigen/targeting antibodies are arranged in a variety of configurations as described above.

II. Fusion Constructs

In some embodiments, the present invention provides fusion constructs (e.g., fusion protein or nucleic acids encoding fusion proteins) comprising a MHC class II targeting entity or nucleic acid encoding the targeting entity fused to a molecule of interest or nucleic acid encoding the molecule of interest (e.g., antigen).

Figure 11B:
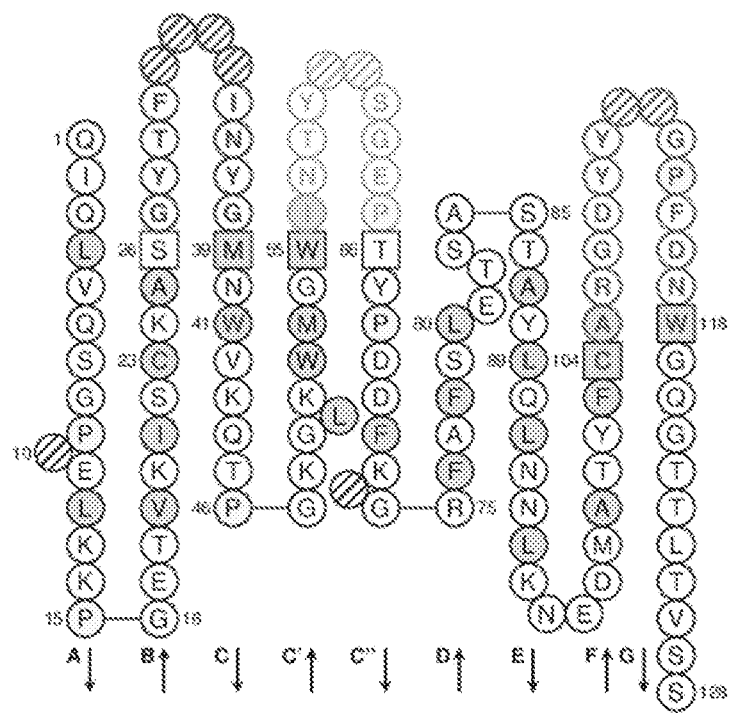
Figure 12B:
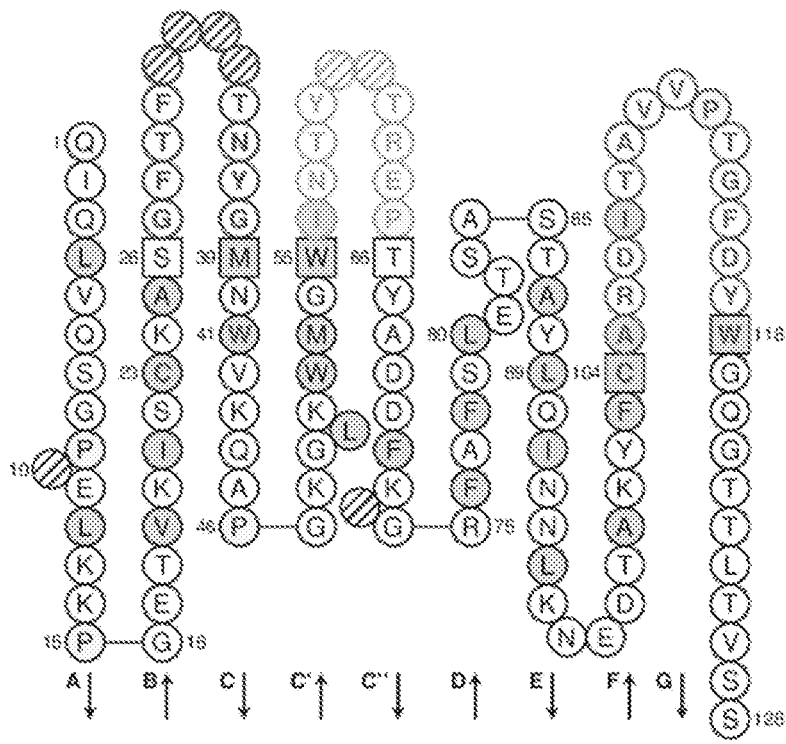

In some embodiments, the MHC class II targeting entity is an antigen binding protein (e.g., an immunoglobulin or fragment thereof, scFv, nanobody, etc.). In some particularly preferred embodiments, the MEW class II targeting entity comprises the amino acid sequences SEQ ID NOS: 4 (CDR 1), 5 (CDR 2) and 6 (CDR 3) determining the CDRs of the $V_L$ region, and the amino acid sequences SEQ ID NOS: 7 (CDR 1), 8 (CDR 2) and 9 (CDR 3) determining the CDRs of the $V_H$ region or an immunoglobulin, comprising: the amino acid sequences SEQ ID NOS: 11 (CDR 1), 12 (CDR 2) and 13 (CDR 3) determining the CDRs of the $V_L$ region, and the amino acid sequences SEQ ID NOS: 14 (CDR 1), 15 (CDR 2) and 16 (CDR 3) determining the CDRs of the $V_H$ region. Exemplary immunoglobulins are shown in FIGS. 11 and 12.

It will be understood that antigen binding proteins may be identified with reference to the nucleotide and/or amino acid sequence corresponding to the variable and/or complementarity determining regions ("CDRs") thereof. For instance, an exemplary antigen binding protein that is derived from, or is related to the antigen binding proteins described above may comprise a variable domain. The variable domains typically comprise one or more CDRs that in large part determine the binding specificity of the antigen binding protein. Antigen binding proteins of the present invention may be identified by analysis of the nucleotide sequences encoding the CDRs or variable regions. The antigen binding proteins of the present invention may also be identified by analysis of the amino acid sequences of (e.g., which may be encoded by the nucleotide sequences) of the CDRs or variable regions. Table 1 provides an identification of the CDRs of various antigen binding proteins of the present invention which are listed in column 1 of the table. In some embodiments, the present invention provides antigen binding proteins wherein one, two or all three of the CDRs of the antigen binding protein have at least 60%, 70%, 80%, 90% or 100% identity to the CDRs identified for each antigen binding protein. In other words, the present invention contemplates that variants of the listed CDRs are within the scope of the invention and that the CDRs may be altered by, for example, substitution, deletion, or addition mutations.

Also within the scope of the invention are natural or synthetic analogs, mutants, variants, alleles, homologs and orthologs (herein collectively referred to as "variants") of the antigen binding proteins of the invention as described herein. Generally, in such variants, one or more amino acid residues may have been replaced, deleted and/or added, compared to the exemplary sequences provided herein. Such substitutions, insertions or deletions may be made in one or more of the framework regions and/or in one or more of the CDRs. Variants, as used herein, are sequences wherein each or any framework region and each or any complementarity determining region shows at least 80% identity, preferably at least 85% identity, more preferably 90% identity, even more preferably 95% identity or, still even more preferably 99% identity with the corresponding region in the reference sequence (i.e., FR1_variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST. (See, e.g., Higgins & Sharp, CABIOS 5:151 (1989); Altschul S. F., W. Gish, W. Miller, E. W. Myers, D. J. Lipman. Basic local alignment search tool. J. Mol. Biol. 1990; 215:403-10.) Software for performing BLAST analyses is publicly available through the National Center for Biotechnology Information (on the worldwide web at ncbi.nlm.nih.gov/). Such variants of antigen binding proteins may be of particular advantage since they may have improved potency or other desired properties.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about two, about five, about ten, up to about twenty, up to about thirty or up to about fifty or more amino acids. A protein or a fragment thereof may contain more than one deletion.

An "insertion" or "addition" is that change in an amino acid or nucleotide sequences which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about one, about three, about five, about ten, up to about twenty, up to about thirty or up to about fifty or more amino acids. A protein or fragment thereof may contain more than one insertion.

A "substitution," as used herein, results from the replacement of one or more amino acids or nucleotides by different amino acids or nucleotides, respectively as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

By means of non-limiting examples, a substitution may, for example, be a conservative substitution (as described herein) and/or an amino acid residue may be replaced by another amino acid residue that naturally occurs at the same position in another $V_HH$ domain. Thus, any one or more substitutions, deletions or insertions, or any combination thereof, that either improve the properties of the antigen binding protein of the invention or that at least do not detract too much from the desired properties or from the balance or combination of desired properties of the antigen binding protein of the invention (i.e., to the extent that the antigen binding protein is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may, for example, involve introducing a limited number of possible substitutions and determining their influence on the properties of the antigen binding proteins thus obtained.

According to particularly preferred embodiments, variants of the antigen binding proteins of the present invention may have a substitution, deletion or insertion, of one, two or three amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3. More preferably, variants of the antigen binding proteins of the present invention may have a conservative substitution (as defined herein) of one, two or three amino acids in one, two or three of the CDRs, more specifically (i) in CDR1 or CDR2 or CDR3; (ii) in CDR1 and CDR2, or, in CDR1 and CDR3, or, in CDR2 and CDR3; (iii) in CDR1 and CDR2 and CDR3.

The term modified antigen binding protein is also intended to include antigen binding proteins, such as monoclonal antibodies, chimeric antibodies, and humanized antibodies which have been modified by, for example, deleting, adding, or substituting portions of the antibody. For example, an antibody can be modified by deleting the hinge region, thus generating a monovalent antibody. Any modification is within the scope of the invention so long as the antibody has at least one antigen binding region specific.

Chimeric mouse-human monoclonal antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 [each of which is herein incorporated by reference in its entirety]; Better et al., Science, 240:1041-1043 [1988]; Liu et al., Proc. Nat. Acad. Sci. USA, 84:3439-3443 [1987]; Liu et al., J. Immunol., 139:3521-3526 [1987]; Sun et al., Proc. Nat. Acad. Sci. USA, 84:214-218 [1987]; Nishimura et al., Canc. Res., 47:999-1005 [1987]; Wood et al., Nature, 314: 446-449 [1985]; and Shaw et al., J. Natl. Cancer Inst., 80:1553-1559 [1988]).

The chimeric antibody can be further humanized by replacing sequences of the Fv variable region that are not directly involved in antigen binding with equivalent sequences from human Fv variable regions. General reviews of humanized chimeric antibodies are provided by S. L. Morrison, Science, 229:1202-1207 (1985) and by Oi et al., Bio. Techniques, 4:214 (1986). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector.

Suitable humanized antibodies can alternatively be produced by CDR substitution (e.g., U.S. Pat. No. 5,225,539 (incorporated herein by reference in its entirety); Jones et al., Nature, 321:552-525 [1986]; Verhoeyan et al., Science, 239:1534 [1988]; and Beidler et al., J. Immunol., 141:4053 [1988]). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs; using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

In some embodiments, the monoclonal antibody is a murine antibody or a fragment thereof. In other preferred embodiments, the monoclonal antibody is a bovine antibody or a fragment thereof. For example, the murine antibody can be produced by a hybridoma that includes a B cell obtained from a transgenic mouse having a genome comprising a heavy chain transgene and a light chain transgene fused to an immortalized cell. The antibodies can be of various isotypes, including, but not limited to: IgG (e.g., IgG1, IgG2, IgG2a, IgG2b, IgG2c, IgG3, IgG4); IgM; IgA1; IgA2; IgAsec; IgD; and IgE. In some preferred embodiments, the antibody is an IgG isotype. In other preferred embodiments, the antibody is an IgM isotype. The antibodies can be full-length (e.g., an IgG1, IgG2, IgG3, or IgG4 antibody) or can include only an antigen-binding portion (e.g., a Fab, F(ab')$_2$, Fv or a single chain Fv fragment).

In preferred embodiments, the immunoglobulin is a recombinant antibody (e.g., a chimeric or a humanized antibody), a subunit, or an antigen binding fragment thereof (e.g., has a variable region, or at least a complementarity determining region (CDR)).

In some embodiments, the immunoglobulin is monovalent (e.g., includes one pair of heavy and light chains, or antigen binding portions thereof). In other embodiments, the immunoglobulin is a divalent (e.g., includes two pairs of heavy and light chains, or antigen binding portions thereof).

CDRs (complementarity-determining regions) are amino acid sequences from antibodies that are, at least in part, responsible for binding of an antibody to a specific target. It is understood by those of skill in the art that CDRs may be identified using any of several techniques and/or schemes. CDRs of the antigen binding proteins shown herein may be identified using any of these techniques. The antigen binding proteins have three CDR regions, each non-contiguous with the others (termed CDR1, CDR2, CDR3). The delineation of the FR and CDR sequences is often based on the IMGT unique numbering system for V-domains and V-like domains. (See, e.g., Lefranc M. P., C. Pommie, et al. (2003). "IMGT unique numbering for immunoglobulin and T cell receptor variable domains and Ig superfamily V-like domains." Developmental and Comparative Immunology 27(1): 55-77.) Alternatively, the delineation of the FR and CDR sequences can be done by using the Kabat numbering system as applied to V$_H$H domains from Camelids in the article of Riechmann and Muyldermans. (See, e.g., Riechmann and Muyldermans J. Immunol. Methods 2000; 240: 185-195.) As will be known by the person skilled in the art, the antigen binding proteins can in particular be characterized by the presence of one or more Camelidae hallmark residues in one or more of the framework sequences (according to Kabat numbering), as described, for example, in WO 08/020,079, on page 75, Table A-3, incorporated herein by reference).

A summary of various schemes, in part based on, for example, Kabat et al, "Sequences of Proteins of Immunological Interest," 5th Ed., Public Health Service, National Institutes of Health, Bethesda, Md., NIH publication No. 91-3242 (1991), and Al-Lazikani et al, "Standard conformations for the canonical structures of immunoglobulins," J. Mol. Biol. 273:927-948, 1997, is provided in Table 2 below:

TABLE 2

| CDR Loop* | Kabat | AbM | Chothia | Contact |
|---|---|---|---|---|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chotia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

*L = light chain; H = heavy chain

CDRs may also be identified by following a set of rules such as those set forth in Table 3 below (as described at http://www.bioinf.org.uk/abs/#cdrid):

TABLE 3

| CDR*/Feature | Typical Characteristic of Feature** |
|---|---|
| CDR-L1 | |
| Start | approximately residue 24 |
| Residues before | typically Cys |
| Residues after | typically Trp (e.g., Trp-Tyr-Gln, Trp-Leu-Gln, Trp-Phe-Gln, Trp-Tyr-Leu) |
| Length | 10 to 17 residues |
| CDR-L2 | |
| Start | typically 16 residues after the end of L1 |
| Residues before | typically Ile-Tyr, Val-Tyr, Ile-Lys, or Ile-Phe |
| Length | typically seven (7) residues |
| CDR-L3 | |
| Start | typically 33 residues after end of L2 |
| Residues before | typically Cys |
| Length | typically Phe-Gly-X-Gly |
| Residues after | 7 to 11 residues |
| CDR-H1 | |
| Start | Approximately residue 26 (typically four (4) residues after a Cys) (Chothia/AbM definition); Kabat definition starts 5 residues later |
| Residues before | typically Cys-X-X-X |
| Residues after | typically Trp (e.g., Trp-Val, Trp-Ile, Trp-Ala) |
| Length | 10 to 12 residues (AbM definition); Chothia definition excludes the last four (4) residues |
| CDR-H2 | |
| Start | typically 15 residues after the end of Kabat/AbM definition of CDR-H1 |
| Residues before | typically Leu-Glu-Trp-Ile-Gly |
| Residues after | typically Lys/Arg-Leu/Ile/Val/Phe/Thr/Ala-Thr/Ser/Ile/Ala |
| Length | Kabat definition 16 to 19 residues; AbM (and recent Chothia) definition 9 to 12 residues |
| CDR-H3 | |
| Start | typically 33 residues after end of CDR-H2 (typically two (2) residues following a Cys) |
| Residues before | typically Cys-X-X (typically Cys-Ala-Arg) |
| Residues after | typically Trp-Gly-X-Gly |
| Length | typically 3 to 25 residues |

*L = light chain; H = heavy chain;
**X = any amino acid

These systems for identifying CDRs are merely exemplary and others may be suitable, as would be understood by one of ordinary skill in the art. CDRs thus identified may be used to identify suitable antigen binding proteins. These systems may be used to identify the CDR region of an antigen binding protein so that the CDRs of the present invention may be used to replace existing CDRs in the antigen binding protein or inserted into an appropriate framework or variable region of the antigen binding protein. Such CDRs may also be combined with one another in any order and/or combination to form hybrid and/or fusion binding agents and/or inserted into the other heavy and/or light chain variable regions using standard techniques. The amino acid sequences of the antigen binding proteins, and/or any one or more fragments and/or derivatives thereof, may be encoded by any of several nucleic acid sequences. These nucleic acid sequences may also be used to identify and/or prepare (e.g., as nucleic acid molecules) suitable antigen binding proteins. For example, one of ordinary skill in the art may devise nucleotide sequences encoding any such amino acid sequences. Any of the nucleotide sequences and/or fragments and/or derivatives thereof, may be combined with one another in any order and/or combination to encode hybrid and/or fusion binding agents and/or inserted into the other nucleic acid sequences encoding light and/or heavy chain variable regions (and/or fragments and/or derivatives thereof).

In some embodiments, the molecule of interest is a protein (or nucleic acid encoding a protein) used therapeutically to induce immune responses that will aid or remedy disease progression (e.g., viral infection, autoimmune diseases, or cancer).

In some embodiments, the molecule of interest is a pathogen-derived antigen (e.g., a nucleic acid or a polypeptide encoding an antigen or antigens from a pathogen). Exemplary pathogenic organisms include, but are not limited to, bacteria, viruses, fungi and protozoa. In some preferred embodiments, the pathogen-derived antigen is influenza hemagglutinin (HA). In some particularly preferred embodiments, the HA is H1, H2, H3, H5, H7 or H9. In some preferred embodiments, antigens from other pathogenic organisms may also be used in the fusion of the present invention, including Ebola virus, Chikungunya, Lassa, Nipah, MERS, SARS, Nairovirus, and Rift Valley Fever virus.

Exemplary pathogens from which antigens may be obtained from include, but are not limited to, In some embodiments, the microorganism is *Bacillus*, including *Bacillus anthracis; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *Y. lamblia, Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium; B. anthracis, Y. pestis, Brucella* spp., *F. tularensis, B. mallei, B. pseudomallei, B. mallei, B. pseudomallei, C. botulinum, Salmonella* spp., SEB *V. cholerae* toxin B, *E. coli* O157:H7, *Listeria* spp., *Trichosporon beigelii, Rhodotorula species, Hansenula anomala, Enterobacter* sp., *Klebsiella* sp., *Listeria* sp., *Mycoplasma* ssp., *Francisella* spp., *Bartonella* spp., *Borrelia* spp., *Campylobacter* spp., *Chlamydia* spp., *Simkania* spp., *Ehrlichia* spp., *Enterococcus* spp., *Coccidioides* spp., *Bordetella* spp., *Coxiella* spp., *Ureaplasma* spp., *Trichomatis* spp., *Helicobacter* spp., *Legionella* spp., *Mycobacterium* spp., *Corynebacterium* spp., *Rhodococcus* spp., *Rickettsia* spp., *Arcanobacterium* spp., *Listeria* spp., *Treponema* spp., *Brucella* spp., *Campylobacter* spp., *Pasteurella* spp., *Pseudomonas* ssp., *Burkholderii* spp. and the like, orthomyxoviruses, (e.g. influenza virus), paramyxoviruses (e.g., respiratory syncytial virus, mumps virus, measles virus), adenoviruses, rhinoviruses (human and porcine), coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B, C and E), herpesviruses (e.g., Herpes simplex virus, HV-I and HV-II, varicella-zoster virus, cytomegalovirus, Epstein-Barr virus), rotaviruses, Norwalk viruses, hantavirus, arenavirus, rhabdovirus (e.g. rabies virus), retroviruses (including HIV-1, HIV-2, HTLV-I and -II), papovaviruses (e.g. papillomavirus), polyomaviruses, picornaviruses, Dengue virus, Filoviruses (e.g., Marburg and Ebola viruses), Hantavirus, Rift Valley virus, HHV-8, Human papillomavirus, Bovine leukemia virus, Influenza virus, Guanarito virus, Lassa virus, Measles virus, Rubella virus, Mumps virus, Chickenpox (Varicella virus), Monkey pox, Epstein Bahr virus, Parvovirus B19, Hantaan virus, Sin Nombre virus, Venezuelan equine encephalitis, Sabia virus, West Nile virus, Yellow Fever virus, and the like, causative agents of transmissible spongiform encephalopathies, Creutzfeldt-Jakob disease agent, variant Creutzfeldt-Jakob disease agent, *Candida* strains including *C. glabrata, C. albicans, C. krusei, C. lusitaniae* and *C. maltosa*, as well as species of *Aspergillus, Cryptococcus, Histoplasma, Coccidioides, Blastomyces*, and *Penicillium, Cryptcooccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi, Ancylostama, Strongylus, Trichostrongylus, Haemonchus, Ostertagia, Ascaris, Toxascaris, Uncinaria, Trichuris, Dirofilaria, Toxocara, Necator, Enterobius, Strongyloides* and *Wuchereria; Acanthamoeba* and other amoebae, *Cryptosporidium, Fasciola, Hartmanella, Acanthamoeba, Giardia lamblia, Isospora belli, Leishmania, Naegleria, Plasmodium* spp., *Pneumocystis carinii, Schistosoma* spp., *Toxoplasma gondii*, and *Trypanosoma* spp., among other viruses, bacteria, archaea, protozoa, fungi, and the like).

The fusion molecules described herein can further comprise antigens from mammalian targets, including but not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Clostridium botulinum toxin, Clostridium perfringens toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxinl, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta7, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bpi, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGGI, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R3Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSFIA (TNF R1CD120a, p55-60), TNFRSFIB (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1 BB CD137, ILA), TNFRSF21 (DR6), TNFRSF22 (DcTRAIL R2TNFRH2), TNFRST23 (DcTRAIL R1 TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TLIA/VEGI), TNFSF18 (GITR Ligand AITR Ligand, TL6), TNFSFIA (TNF-a Conectin, DIF, TNFSF2), TNFSFIB (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCRI, XCRI, XEDAR, XIAP, XPD, and receptors for hormones and growth factors.

One skilled in the art will appreciate that the aforementioned list of targets refers not only to specific proteins and biomolecules, but the biochemical pathway or pathways that comprise them. For example, reference to CTLA-4 as a target antigen implies that the ligands and receptors that make up the T cell co-stimulatory pathway, including CTLA-4, B7-1, B7-2, CD28, and any other undiscovered ligands or receptors that bind these proteins, are also targets. Thus target as used herein refers not only to a specific biomolecule, but the set of proteins that interact with said target and the members of the biochemical pathway to which said target belongs. One skilled in the art will further appreciate that any of the aforementioned target antigens, the ligands or receptors that bind them, or other members of their corresponding biochemical pathway, may be operably linked to the Fc variants of the present invention in order to generate an Fc fusion. Thus for example, an Fc fusion that targets EGFR could be constructed by operably linking an Fc variant to EGF, TGF-b, or any other ligand, discovered or undiscovered, that binds EGFR. Accordingly, an Fc variant of the present invention could be operably linked to EGFR in order to generate an Fc fusion that binds EGF, TGF-b, or any other ligand, discovered or undiscovered, that binds EGFR. Thus virtually any polypeptide, whether a ligand, receptor, or some other protein or protein domain, including but not limited to the aforementioned targets and the proteins that compose their corresponding biochemical pathways, may be operably linked to the Fc variants of the present invention to develop an Fc fusion.

The choice of suitable antigen depends on the desired application. In some embodiments, constructs described herein target pathogen antigens. For anti-cancer treatment it is desirable to have a target whose expression is restricted to the cancerous cells. Some targets that have proven especially amenable to antibody therapy are those with signaling functions. Other therapeutic antibodies exert their effects by blocking signaling of the receptor by inhibiting the binding between a receptor and its cognate ligand. Another mechanism of action of therapeutic antibodies is to cause receptor down regulation. Other antibodies do not work by signaling through their target antigen. In some cases, antibodies directed against infectious disease agents are used.

In one embodiment, the fusion proteins of the present invention are used for the treatment of autoimmune, inflammatory, or transplant indications. Target antigens and clinical products and candidates that are relevant for such diseases include but are not limited to anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, anti-TNF (TNF, TNFa, TNFa, TNF-alpha) antibodies such as CDP571, CDP870, D2E7, Infliximab, MAK-195F, and anti-VLA-4 antibodies such as Antegren.

In some embodiments, the HLAII-specific targeting moiety is inserted into a vaccine format where it is linked either directly or via a linker to the molecule of interest. In some embodiments, the HLAII-specific immunoglobulin is inserted into vaccine formats also comprising one or more multimerization units. The multimerization unit may comprise a dimerization unit securing bivalent display of the HLAII-targeted moiety as well as the molecules of interest; or it may comprise a trimerization domain securing trivalent display of the HLAII-targeted moiety and some molecules of interest. Furthermore, it may comprise any multimerization units aiming at multivalent display of molecules of interest, the HLAII-targeted moiety, or both.

The present invention is not limited to a particular configuration of MHCII targeting molecules and molecules of interest. For example, in some embodiments, the fusion protein comprises two HLAII-specific scFv linked via a dimerization unit to two molecules of interest. In some embodiments, the fusion protein comprises a HLAII-specific scFv linked directly, or via a linker, to a single molecule of interest. In some embodiments, the fusion protein comprises at least two distinct antigens. In some embodiments, the fusion protein comprises one or more multimerization domains that is intended to multimerize the HLAII-targeted moiety, and/or the molecules of interest. In some embodiments, the molecule of interest is an antigen derived from a pathogenic microorganism (e.g., influenza virus or ebola virus). In some embodiment, the molecule of interest comprises a protein (or DNA/RNA encoding a protein) that is designed to induce immune responses for therapeutic treatment or remedy of autoimmune diseases or cancer.

In some embodiments, the present invention provides bivalent homodimeric vaccines. For example, in some embodiments, the fusion proteins find use in vaccibody vaccines (See e.g., U.S. Pat. No. 8,932,693 B2, incorporated by reference herein in its entirety). The Vaccibody molecule comprises antigen coupled, via a dimerization unit derived from human IgG3 (hinge+CH3 domains), to targeting units. The targeting units may be different natural ligands or scFv derived from antibodies of various specificities. The present invention has been extensively tested as targeting unit in this vaccine format (See e.g., Examples 1 and 2).

In some embodiments, homodimeric vaccines are constructed by a number of different strategies. Some publications describe the use the CH2 and CH3 domains of IgG for dimerization of selected antigens (e.g., Soleimanpour et al, 2015, Appl Microbiol Biotechnol). In some embodiments, Fab-fragments are used for multimerization (e.g., Mayer et al, 2015, Int J Mol Sci), and some use coupling of antigen to full length antibodies that have been equipped with new V-regions (e.g., Caminschi et al, 2008, Blood; Bonifaz et al, 2002, J Exp Med). In all these instances, and in any other Ig-based vaccine format, the panHLAII-specificity of the present invention is inserted into the construct for improved induction of immune responses after vaccination.

In some embodiments, the targeting units described herein are used in bivalent heterodimeric vaccines. The bacterial ribonuclease bamase and its inhibitor barstar interact with high affinity. This interaction has been used to construct a dimerization unit that allows selective expression of four different fusion subunits (Spang et al, 2012, PLoS ONE). In some embodiments, the scFv against panHLAII is inserted into this format, or any other vaccine format based on dimerization units from natural proteins, for improved induction of immune responses after vaccination.

In some embodiments, the targeting units find use in monovalent vaccines. For example, in some embodiments, the scFv specific for panHLAII is coupled to an antigen, either directly, or via a linker. Previously, several constructs have been constructed in this manner with antigen coupled to a natural ligand (ex: Biragyn et al, 1999, Nat Biotechnol), or directly to a scFv (ex: Cao et al, 2013, BMC Immunology).

In some embodiments, multivalent vaccines comprising the scFv specific for panHLAII molecules linked to various forms of multimers are utilized.

In some embodiments, the panHLAII-specific scFv is coupled to antigen via a short linker, and the antigen is trimerized by a foldon domain (Jardine et al, 2015, Science).

In some embodiments, the scFvs described herein target human HLAII molecules. Antibodies represent a strong correlate of protection against many infectious diseases (e.g., influenza, ebola, zika, dengue virus, and many more), and the scFv specific for panHLAII-molecules is particularly useful in such applications. The targeting unit cross-reacts with mammalian MHCII molecules (species tested: horses, cows, pigs, ferrets, rhesus macaques, guinea pigs), so the panHLAII-specific targeting unit further finds use for veterinary vaccinations.

III. Uses

The fusion constructs described herein find use in a variety of applications (e.g., vaccination, treatment of autoimmune disease and allergies, and cancer immunotherapy).

In some embodiments, the present invention provides vaccine compositions comprising the fusion constructs (i.e., nucleic acids encoding a fusion, or the fusion protein itself) described herein.

In some preferred embodiments, the vaccines are nucleic acid vaccines such as DNA vaccines. In these embodiments, the DNA vaccine comprises DNA molecules encoding the fusion constructs above, alone or in association with other desired sequences. DNA vaccines, like peptide-based vaccines, are advantageous in being relatively easy and inexpensive to manufacture, and are not individualized for patients, as are dendritic cell-based vaccines. Unlike recombinant protein vaccines, in which the antigen is taken up by antigen presenting cells and expressed predominantly in the context of MHC class II, DNA in nucleic acid vaccines is taken up and expressed by antigen-presenting cells directly, leading to antigen presentation through both naturally processed MHC class I and II epitopes.

In some embodiments, DNA vaccines comprise nucleic acids encoding an fusion construct described herein in a vector suitable for expression of the nucleic acid. In some embodiments, the nucleic acid is expressed in an expression cassette. In particular embodiments, the expression cassette is a eukaryotic expression cassette. The term "eukaryotic expression cassette" refers to an expression cassette which allows for expression of the open reading frame in a eukaryotic cell. A eukaryotic expression cassette comprises regulatory sequences that are able to control the expression of an open reading frame in a eukaryotic cell, preferably a promoter and polyadenylation signal. Promoters and polyadenylation signals included in the recombinant DNA molecules are selected to be functional within the cells of the subject to be immunized. Examples of suitable promoters, especially for the production of a DNA vaccine for humans, include but are not limited to promoters from cytomegalovirus (CMV), such as the strong CMV immediate early promoter, Simian virus 40 (SV40), Mouse Mammary Tumor Virus (MMTV), Human Immunodeficiency Virus (HIV), such as the HIF Long Terminal Repeat (LTR) promoter, Moloney virus, Epstein Barr Virus (EBV), and from Rous Sarcoma Virus (RSV) as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals.

Other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

The present invention is not limited by the particular formulation of a vaccine composition. When the vaccine is a DNA vaccine, the vaccine may preferably be provided in saline or other physiologically acceptable solution or buffer. In some embodiments, the DNA is administered intramuscularly by needle injection into one or tissues. In some embodiments, an effective route is intramuscular injection into the hind leg quadriceps or tibialis anterior, followed by intradermal injection. These routes usually provoke strong, antigen-specific Th1-biased, humoral and cellular immune responses. In other embodiments, a gene gun is utilized. In these embodiments, the DNA vaccine described is above is coated onto particles, preferably gold particles. In still further embodiments, needle-free injection systems are utilized. These systems generally utilize a pressurized fluid or gas to deliver the DNA to a vaccination site. Suitable systems include those provided by Pharmajet (Golden, Colo.) and Bioject (Tualatin, Oreg.), among others.

The delivery method generally determines the dose required to raise an effective immune response. Saline injections require variable amounts of DNA, from 10 μg-1 mg, whereas gene gun deliveries require 100 to 1000 times. Generally, 0.2 μg-20 μg are required, although quantities as low as 16 ng have been reported. These quantities vary by species. Mice for example, require approximately 10 times less DNA than primates. Saline injections require more DNA because the DNA is delivered to the extracellular spaces of the target tissue (normally muscle), where it has to overcome physical barriers (such as the basal lamina and large amounts of connective tissue, to mention a few) before it is taken up by the cells, while gene gun deliveries bombard DNA directly into the cells, resulting in less "wastage".

Where the vaccine is a fusion protein, a vaccine composition of the present invention may comprise one or more different agents in addition to the fusion protein. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a vaccine composition comprising a fusion protein comprises an agent and/or co-factor that enhance the ability of the immunogen to induce an immune response (e.g., an adjuvant). In some preferred embodiments, the presence of one or more co-factors or agents reduces the amount of immunogen required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells. Most mature CD4+T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in preferred embodiments, the present invention provides a method of stimulating a Th2-type immune response in a subject comprising administering to a subject a fusion protein of the present invention. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Mont. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree *Quillaja Saponaria* Molina), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an *E. Coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising an immunogen of the present invention.

Additional examples of adjuvants that find use in the present invention include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising a fusion protein of the present invention, or, the adjuvant may be formulated with carriers, for example liposomes, or metallic salts (e.g., aluminium salts (e.g., aluminium hydroxide)) prior to combining with or co-administration with a composition.

In some embodiments, a composition comprising a fusion protein of the present invention comprises a single adjuvant. In other embodiments, a composition comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a fusion protein of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a fusion protein of the present invention) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the mucoadhesive.

In some embodiments, the fusion constructs are used in conjunction with appropriate salts and buffers to render delivery of the compositions to a subject. Buffers also are employed when the compositions are introduced into a patient. Aqueous compositions comprise an effective amount of composition dispersed in a pharmaceutically acceptable carrier or aqueous medium. Such compositions also are referred to as inocula.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with the vectors or cells of the present invention, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The compositions may also be administered parenterally or intraperitoneally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the fusion constructs in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Fusion constructs of the invention may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive fusion constructs by inhalation.

Ordinarily, an aqueous aerosol is made by formulating an aqueous solution or suspension of the fusion construct together with conventional pharmaceutically acceptable carriers and stabilizers. The carriers and stabilizers vary with the requirements of the particular fusion construct, but typically include nonionic surfactants (TWEENs, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver fusion constructs of the invention.

Aerosols containing fusion constructs for use according to the present invention are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the fusion construct and a suitable powder base such as lactose or starch.

Delivery of aerosols of the present invention using sonic nebulizers is advantageous because nebulizers minimize exposure of the agent to shear, which can result in degradation of the fusion construct.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the fusion constructs maybe formulated in oily solutions or as a gel. For administration of nasal aerosol, any suitable propellant may be used including compressed air, nitrogen, carbon dioxide, or a hydrocarbon based low boiling solvent.

Dosage forms for the topical (including buccal and sublingual) or transdermal administration of fusion constructs of the invention include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

EXPERIMENTAL

Example 1

Materials and Methods
Cells and Antibodies

Human embryonic kidney (HEK) 293E cells and NSO cells were purchased from American Type Culture Collection (ATCC, Manassas, Va., US). T18 is a human HLA-DR4 (DRA1, DRB1*0401)-restricted T cell clone specific for aa 40-48 of mouse Ig Cκ (25). The murine hybridoma producing the anti-HLAII mAb (HKB1, IgM)(26) was a kind gift from Dr. Steinar Funderud, Oslo University Hospital. The anti-HLA-DR (L243, IgG2a)(27) was purchased from ATCC. The use of human peripheral blood mononuclear cells (PBMC) was approved by the Norwegian Regional Committee for Medical and Health Research Ethics (REC, 2014/1505). The cells were purified from whole blood by LymphoPrep density gradient centrifugation (Nycomed, Oslo, Norway).

Construction of Vaccine Molecules mRNA was isolated from the hybridomas HKB1 and L243 by use of Dynabeads® mRNA DIRECT TM kit (Dynal, Oslo, Norway), and cDNA synthesized using cDNA Synthesis Kit (Amersham Biosciences, Oslo, Norway). The V(D)J of HKB1 and L243 heavy and light chain genes were PCR amplified from the cDNA with degenerate primers complimentary to the leader sequence of VL and VH, and IgM, IgG1 and Cκ. The PCR products for the light chain and heavy chain were ligated into individual pGEM®-T Easy vectors (Promega, Madison, Wis., USA). To obtain scFv specific for HKB1 and L243, PCR reactions were run to reamplify the VH and VL domains from the pGEM®-T Easy vectors with specific primers including linkers and restriction enzyme sites (BsmI/BsiWI) for subcloning. 5'VH HKB1/L243: ggc gga ggt ggc tct ggc ggt ggc gga tcg CAG ATC CAG TTG GTG CAG TCT (SEQ ID NO: 26) and 3'VH HKB-1/L243: ga c gtacg a ctc acc TGA GGA GAC TGT GAG AGT GG (SEQ ID NO: 27). Next, the various scFv were BsmI/BsiWI digested and cloned into the BsmI/BsiWI cassette of pLNOH2(28) or pUMVC(29) (kind gift from Bob Weinberg, Addgene plasmid #8449) expression vectors to generate vaccine constructs with specificities for NIP, pan anti-HLAII, and anti-DR. The vaccine constructs were equipped with antigenic units by subcloning either the scFv-like homodimer CκCκ, HA from influenza A/Puerto Rico/8/1934 (H1N1) (PR8), or HA from influenza A/California/07/2009 (H1N1) (Cal07)(23) on SfiI sites.

Western Blot

Vaccine proteins containing the scFv CκCκ as antigen, affinity purified (187.1 mAb column) from supernatants of stably transfected NSO cells, were run on a Novex 4-12% Tris-Glycine gel (Invitrogen, Life Technologies, CA, US) together with a Seegreen Plus2 Prestained Standard (LC5925, Invitrogen, Life Technologies, CA, US), blotted (Immun-Blot PVDF membrane, 162-0177, BioRad, CA, US) and incubated with biotinylated HP6017 (anti-human IgG CH3) (BioLegend, Calif., US) and Streptavidin-HRP (RPN1231V, GE Healthcare, Buckinghamshire, UK). The membrane was developed with the ECL Western Blotting analysis system (RPN2109, GE Healthcare, Buckinghamshire, UK) and analyzed on a Kodak Image station 200R (LabX, Canada) with Molecular Imaging Software v 4.0.5. One µg of DNA plasmids encoding vaccine constructs with HA as antigen were transiently transfected into 293E-cells ($1 \times 10^5$/well) by addition of Lipofectamin2000 (11668-019, Invitrogen, Life Technologies, CA, US). Supernatants were collected after 48 hours, and Western blot performed as described above. Proteins were detected with biotinylated H36-4-52 anti-HA mAb (kind gift from Siegfried Weiss, Braunschweig)(30), and developed as described above.

Sandwich ELISA

ELISA plates (Costar 3590, Sigma-Aldrich, Mo., US) were coated with either 1 µg/ml of mAb 187.1 (anti-mouse Cκ)(31), MCA878 (anti-human CH3) (AbD Serotec, Calif., US), or NIP-BSA, blocked, and incubated with supernatants from transiently transfected 293E-cells (as above). Next, plates were incubated (1p g/ml) with either biotinylated 187.1, or HP6017 (BioLegend, Calif., US), or H36-4-52, and Streptavidin alkaline phosphatase (1:5000) (GE Healthcare, Buckinghamshire, UK). Plates were developed using Phosphatase substrate (P4744-10G, Sigma Aldrich, Mo., US) dissolved in substrate buffer, and read with a Tecan reader (Tecan, Switzerland) using the Magellan v5.03 program.

Flow Cytometry

Vaccine protein-staining of PBMC: Freshly isolated human PBMC were stained sequentially with purified vaccine proteins, biotinylated HP6017 and streptavidin-APC (BD Pharmingen, Calif., US). Cells were run on a BD FACScalibur system (BD Biosciences, N.J., US) and analyzed by FlowJo software (Version 7.6) (FlowJo, Oreg., US).

Vaccine protein-staining of cells from DQ2 transgene mice: Splenocytes from 3 DQ2 transgenic mice (32) were FcγR-blocked by incubation with 30% heat aggregated rat serum and 0.1 mg/ml 2.4G2 mAb (Fisher Scientific, MA, US), and stained sequentially with vaccine proteins (10 µg/ml), biotinylated HP6017 (1:2000) (042M4810, Sigma, Mo., US) and Strep-PE (2 µg/ml) (554061, BD Pharmingen, Calif., US). The staining solution also contained either FITC-conjugated mAb against CD19 (4 µg/ml) (35-0193, 9500, TONBO, Calif., US), PerCP-Cy5.5 conjugated mAb against CD11b (3 µg/ml) (66-0112-U100, TONBO, Calif., US), or APC-conjugated mAb against CD11c (20-0114-U100, TONBO, Calif., US). Samples were run on LSRII (Becton Dickinson, N.J., US), and data analyzed as above.

Vaccine protein-staining of cells from larger animals: Blood collected from horses, cows, sheep, ferrets and pigs (n=3 for all species) on EDTA were added to Lympholyte (CL5120, Cedarlane Labs, Canada) (1:1), and centrifuged for 40 min at 1500 rpm. The lymphocyte layer was collected, washed with PBS, and plated out in 96-well plates ($1 \times 10^6$ cells/well). Cells were blocked as above, and stained sequentially with vaccine proteins (10 µg/ml), biotinylated mAb against HA (H36-4-52), and APC-conjugated Streptavidin (554067, BD Biosciences, N.J., US). Samples were run on LSRII, and data analyzed with the FlowJo software (Version 10.0.5). For staining of cells from ferrets, PE-conjugated mAbs against CD11b (clone M1/70) (553311, BD Pharmingen, Calif., US) was also included in the staining solution. For staining of cells from pigs, the vaccine proteins were detected with PE-conjugated mAbs against human IgG (2043-09, SouthernBiotech, Ala., US). FITC-conjugated mAb against CD3E (559582, BD Biosciences, N.J., US), and mAb against CD11R3 (MCA2309, AbD serotec, CA, US) [detected with APC-conjugated mAb against IgG1 (550874, BD Pharmingen, Calif., US)] were included in the staining.

T Cell Proliferation Assays

APC were freshly isolated from PBMC ($7 \times 10^4$/w) of HLA-DR4 (DRA1, DRB1*0401) donors. Experiments were approved by the Norwegian Regional Committee for Medical and Health Research Ethics (REC, 2014/1505). Irradiated APC (20 Gy) and mouse Cκ40-48-specific, DR4-restricted human CD4+ T cells (4×10⁴/w)(25) were cultured in 96-well plates with titrated amounts of the various bivalent vaccines expressing CκCκ. After 48 h, the cultures were pulsed for 16-24 h with 1 µCi [3H]Thymidine, harvested, and [3H]Thymidine incorporated into DNA of proliferating cells was measured using a TopCount NXT Scintillation counter (Packard, Meriden, Conn., US).

Specificity of Vaccine Proteins and HKB1 mAb for HLA Class II

One µg of vaccine proteins expressing CκCκ (purified on column with 187.1 mAb linked to Sepharose) (GE Healthcare, Buckinghamshire, UK) were mixed with HLAII-coated xMAP microbeads (LS2A01, One Lambda, Calif., US) in 96-well plates, and incubated for 30 min at 22oC. Next, plates were washed three times, and samples incubated with PE-conjugated antibodies directed against the CH3-domain dimerization unit (409304, BioLegend, Calif., US) for 30 min at 22° C. Samples containing HKB1 were detected with PE-conjugated anti-mouse IgM (553517, BD Pharmingen, Calif., US). Plates were washed twice, and samples resuspended in PBS before being read on a Luminex 100 flow analyzer (Luminex, Tex., US) and analyzed with the HLA-Visual software (One Lambda, Calif., US). The obtained HLA reactivity profile was then used to evaluate shared regions of the otherwise polymorphic HLA β-chains. Briefly, the complete HLA directory was downloaded (http://www.ebi.ac.uk/ipd/imgt/hla/), aligned with ClustalX2.1(33), and manually edited and annotated in GenDoc (34) to identify the likely HKB epitope. Representative PDB entries were contoured by APBS (35), and visualized using PyMOL Molecular Graphics System (Schrödinger, LLC).

Animals

Six to eight week-old BALB/c and DQ2 transgene mice (32) (on a BALB/c background) were used. Mice were housed under minimal disease conditions at Oslo University Hospital, Oslo, Norway. Six- to eight week old pigs (Noroc) of both sexes were used (Noroc: 50% Norwegian landgris, 25% Norwegian Yorkshire and 25% Duroc). Weights at the start of the experiments ranged from 16-30 kg, whereas weights at the termination of experiments ranged from 34-48 kg. Pigs were housed at the Animal Production Experimental Centre, Norwegian University of Life Science, As, Norway. Experiments in mice and pigs were approved by the National Committee for Animal Experiments (Oslo, Norway). Ferret yearlings (female and male) were used, with weights ranging from 2, 3-7 kg. Ferrets were housed at the Laboratory Animal Facility, University of Copenhagen, Denmark. Experiments in ferrets were approved by the Danish Society for the Protection of Laboratory Animals (Copenhagen, Denmark).

Virus

Influenza A/Puerto Rico/8/1934 (H1N1) (PR8) was kindly provided by Dr. Anna Germundsson, The National Veterinary Institute, Norway. The virus was propagated by an inoculation into the allantoic cavity of 10-day-old embryonated chicken eggs. Allantoic fluid was harvested, confirmed negative for bacterial contaminations, and TCID50 determined.

Vaccination and Viral Challenge

Mice: Mice were anaesthetized by s.c. injection of Hypnorm/Dormicum (0.05 ml working solution/10 g), and vaccinated as previously described (23). Briefly, 25 µl vaccine solution (0.5 mg/ml DNA) was injected intradermally (i.d.) on each flank of the mouse, immediately followed by skin electroporation (EP) with DermaVax (Cellectis, Paris, France). For viral challenge, LD50 was determined as previously described (23), and anaesthetized mice were intranasally infected with 5×LD50 of PR8 (2.0×10⁴TCID) in 20 µl (10 µl per nostril). Mice were monitored for weight loss (n=6/group), with an endpoint of 20% weight reduction, as required by the National Committee for Animal Experiments.

Ferrets: Ferrets were immunized i.d. with 100 µg DNA (pLNOH2-vector) in total, delivered by two separate injections of 100 µl (0.5 mg/ml DNA) at each side of the lower back region. Injection was immediately followed by skin electroporation (DermaVax, Cellectis, Paris, France).

Pigs: Pigs were DNA (pUMVC-vector) immunized either by i.d. needle injection followed by skin electroporation (DermaVax, Cellectis, Paris, France), or by i.d. jet delivery (Tropis, PharmaJet, Del., US).

Serum ELISA

Sera were isolated from blood by two successive centrifugations for 5' at 13 000 rpm. 96-well plates were coated with inactivated PR8 (Charles River, Mass., US) (1:1600 in PBS) or Pandemrix (antigen suspension with A/California/7/2009 (H1N1) v-like strain (X-179A), Glaxo Smith Kline) (1:100 in PBS), blocked with 0.1% BSA in PBS, and incubated overnight at 4° C. with titrated amounts of sera. Antibodies in mouse sera were detected with biotinylated anti-IgG (A2429, Sigma Aldrich, Mo., US), anti-IgG1a (553599, BD Pharmingen, Calif., US), or anti-IgG2aa (553502, BD Pharmingen, Calif., US), followed by Streptavidin alkaline phosphatase (GE Healthcare, Buckinghamshire, UK) and development with Phosphatase substrate (P4744-10G, Sigma Aldrich, Mo., US) dissolved in substrate buffer. The plates were read as above. Titers are given, defined as the last serum dilution giving an absorbance above background (mean absorbance for NaCl-vaccinated mice plus five times SEM). In ferrets and pigs, HA-specific IgG antibodies in sera were detected with alkaline phosphatase conjugated anti-ferret IgG (LS-C61240, LSBio, WA, US) and biotinylated anti-pig IgG (ab112747, Abcam, Cambridge, UK), respectively. Plates were developed and analysed as above.

Microneutralization Assay for Influenza Virus-Specific Antibodies

The microneutralization assay was performed as previously described (23). Briefly, sera were treated with RDE (II) (Denka Seiken, Tokyo, Japan), and twofold duplicate dilutions set up in triplicates. Fifty µl of 100×TCID50 virus (PR8 or Cal07) was added to each well, and plates incubated for 2 h at 370 C in a 5% CO2 humidified atmosphere. MDCK cells (2×10⁵) were added to each well, and plates incubated for 20 hours at 370 C and 5% C02. Monolayers were washed with PBS and fixed in cold 80% acetone for 10 min, and viral proteins detected by an ELISA using biotinylated mAb against the influenza nucleoprotein (HB65, ATCC, VA, US) and Streptavidin-alkaline phosphatase (GE Healthcare, Buckinghamshire, UK). Plates were read as described above.

Statistical Analyses

Statistical analyses were performed using one way Anova and Bonferroni's multiple comparison test with the Graphpad Prism software (GraphPad Software Inc. version 5).

Results:

Cloning of scFv Targeting Units with Specificity for Human HLAII Molecules

We have previously described efficient immune responses in mice elicited by a DNA vaccine format that encodes bivalent homodimers with N-terminal scFv targeting units specific for mouse MHCII molecules, a human IgG3-derived dimerization unit (shortened hinge+CH3), and with C-terminal antigenic units (17,23) (FIG. 1a). In order to test the efficacy of the vaccine format in larger animals and humans, we have here developed novel scFv targeting units directed against human HLAII molecules. The scFvs were derived from two different anti-HLAII specific mAb. The first mAb, L243 (mouse IgG2a), is specific for HLA-DR molecules (27,36). The second mAb, HKB-1 (mouse IgM), reacts more generally with HLAII molecules and is denoted pan(p)HLAII-specific (26). The V regions of the two mAb were cloned from B cell hybridomas, sequenced, scFv were constructed and inserted into cassette vectors (17) that already contained the dimerization unit, and an antigenic unit [either two mouse Cκ domains linked in a scFv-like format (37) or influenza HA (23)]. The resulting HLAII-targeted vaccines are designated αHLADR-CκCκ, αHLADR-HA, αpHLAII-CκCκ and αpHLAII-HA, respectively. As non-targeted controls, we also prepared a vaccine where the HLAII-specific targeting unit was replaced with a scFv specific for the hapten NIP (αNIP-CκCκ/αNIP-HA) (17,23). In addition, a plasmid expressing truncated HA antigens alone was used (the cytosolic tail of HA and part of the transmembrane region were removed to prevent retention in the cell membrane of transfected cells)(23).

Vaccine proteins secreted by cells transiently transfected with the vaccine encoding plasmids had expected sizes and reactivity with mAbs, as evaluated by ELISAs (FIG. 1b) and Western blotting (FIG. 1c). Further, HLAII-targeted vaccine proteins bound all CD19+ cells, about 37-47% of CD11c+, and 5-6% of CD11b+ cells among human PBMC (FIG. 1d). The non-targeted control, αNIP-CκCκ, failed to significantly bind any of the cell populations, although some unspecific binding was observed.

Specificity of Vaccine Proteins for Human HLAII Molecules

Figure 2A:
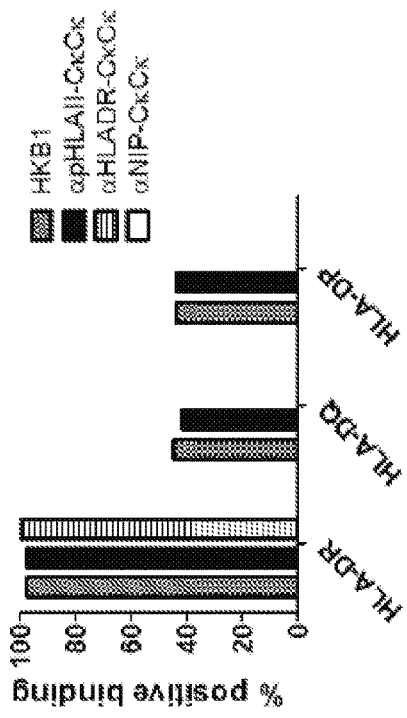
FIG. 2A-C. Specificity of vaccine proteins for HLA class II molecules (a) The indicated vaccine proteins and IgM mAb from the hybridoma HKB1 (donor of scFv for anti-panHLAII vaccine proteins) were assayed for binding to 91 beads coated with either HLA-DR (35 different types), HLA-DQ (29 types) or HLA-DP (27 types) molecules. Shown is the percentage of binding to each series of HLA-II molecules. Information on specific beads employed, and binding, is provided in 13. (b) Sequence alignment of β1-domains with the critical residue 58 highlighted in orange of the HLAII β-chain. Only selected sequences of vaccine interacting and non-interacting (residue 1 highlighted red) HLAs are shown. The relevant HLA sequences were downloaded from IMGT/HLA database, aligned using ClustalX and annotated using GenDoc. (c) Structural and topological comparison of the postulated HKB1 epitope centered on the critical residue position 58 of the β-chain. The solvent exposed surface electrostatic potentials were generated using APBS and contoured onto the molecular surfaces using Pymol. PDB ID codes: 1V9S (DQB1*02:01), 2NNA (DQB1*03:02), 2IAN (DRB1*01:01) and 3LQZ (DPB1*02:01).

The human leukocyte antigen class II (HLAII) loci are among the most polymorphic genes described in the human genome, with some HLAII genes having hundreds of identified alleles (38). We therefore assessed the novel vaccine proteins for their ability to bind 91 different HLAII molecules displayed on the surface of xMAP microbeads. αpHLAII-CκCκ bound 57/91 of the HLAII molecules tested (FIGS. 2a and 13), including all but two HLA-DR molecules (33/35). Binding to HLA-DQ (12/29) and -DP (12/27) alleic variants was less frequent (39). As expected, αHLADR-CκCκ bound all HLA-DR molecules tested (35/35), but none of the HLA-DQ and -DP molecules. The negative control, αNIP-CκCκ failed to bind any HLAII molecules at all. The binding profile of αpHLAII-CκCκ was compared to IgM mAb HKB1, from which the scFv in the targeting units of αpHLAII-CκCκ were derived (26). The binding profiles of the HKB1 IgM and the vaccine proteins were overlapping, except that the original antibody weakly bound one more HLA-DQ molecule than did the vaccine protein (FIG. 13).

Figure 2B:
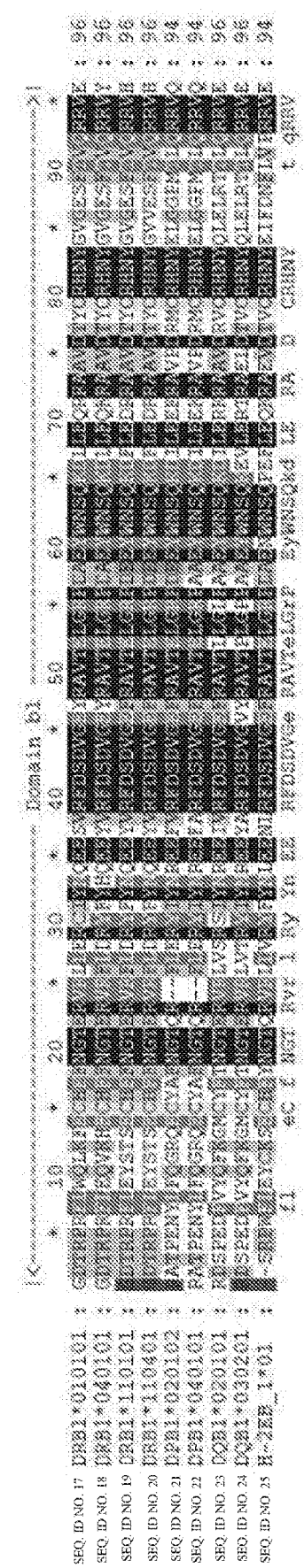
Figure 2C:
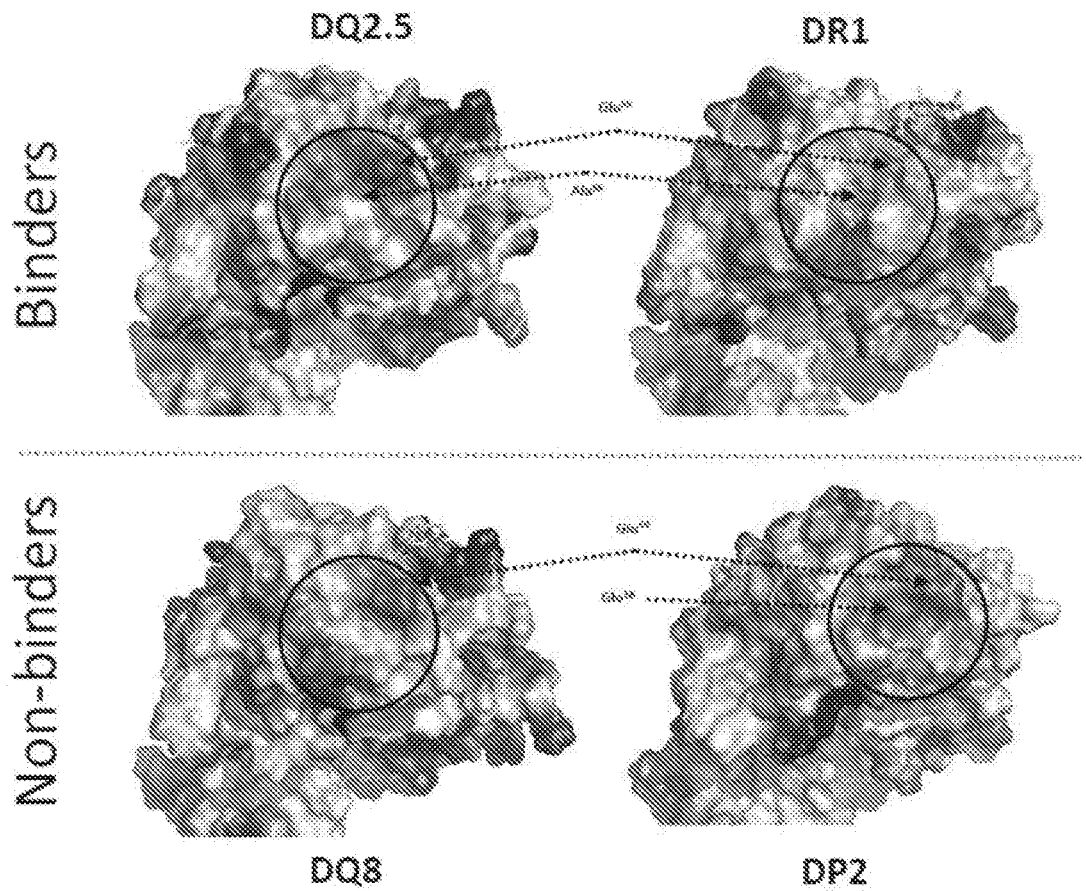

Given the ability of αpHLAII-CκCκ to bind members of all three series of HLAII molecules, a hitherto unappreciated shared structural feature between DP, DR and DP may comprise the binding epitope. Most of the genetic variation in HLAII molecules is located to the more distal parts of the ectodomains, thereby affecting the unique peptide binding properties of these scaffold molecules. An exception is the monomorphic α-chain of HLA-DR, with only one functional allele (40). The inability to bind all HLA-DR molecules made us exclude the monomorphic α-chain from the analysis, and rather focus on the β-chain. Here, a global alignment of the IMGT/HLA database entries (PMID: 25414341) readily singled out a small region in the DR β1-domain that was unique for the two non-reactive DRB1*11:01 DRB1*11:04 alleles. The key feature of this region is an Ala to Glu substitution in the otherwise conserved position of the β-chain. This feature was also shared with the non-reactive DP1*02:01 chain, alluding to the incompatibility with a Glu in position 58 to allow for HKB1 binding (FIG. 2b). Moreover, a complex epitope architecture is likely as Glu58 is not shared with the non-reactive HLA-DQ8 (DQB1*03:02), or the murine I-Ed (H-2EB*01: 01) that rather differ in neighbouring residues (FIG. 2c).

Figure 3:
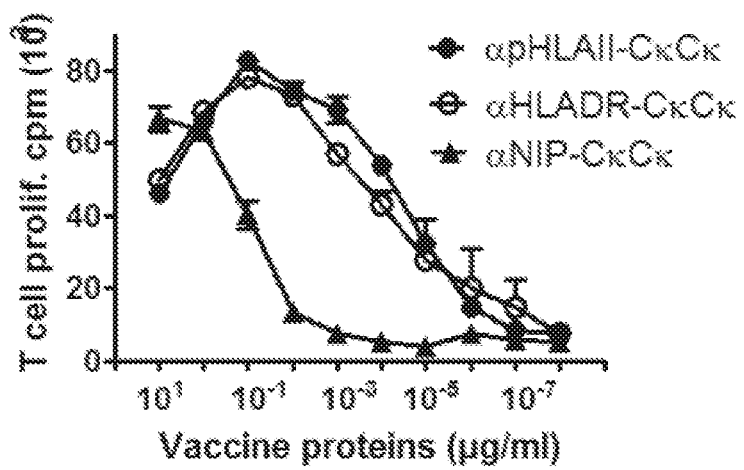
FIG. 3. HLAII-specific vaccine proteins enhance proliferation of antigen-specific CD4+ T cells. Irradiated human PBMC [HLA-DR4+ (DRA1, B1*0401)] were incubated with cloned mouse Cκ-specific DR4-restricted CD4+ T cells in the presence of titrated amounts of various affinity purified vaccine proteins expressing Cκ antigen in a CκCκ scFv format. The cultures were pulsed with [3H]Thymidine, and incorporation into DNA assessed as an indicator of T cell proliferation.

Vaccine Proteins that Target Antigen to HLAII Enhance Proliferation of Human T Cells The two Cκ domains paired in a scFv-like format in the antigenic unit contain an immunogenic T cell epitope (aa40-48) for which we have previously established a DR4-restricted (DRA1/DRB1*0401) human CD4+ T cell clone (37,41). We could therefore test in vitro whether the different vaccine constructs could efficiently stimulate Cx-specific human CD4+ T cells (25). Irradiated PBMC from DR4+ donors were pulsed with titrated amounts of vaccine proteins, and CD4+ T cell proliferation assessed. Strikingly, αHLAII-CκCκ and αHLADR-CκCκ were 1,000-10,000 fold more efficient at stimulating the Cx-specific T cells as compared to αNIP-CκCκ (FIG. 3).

Figure 4:
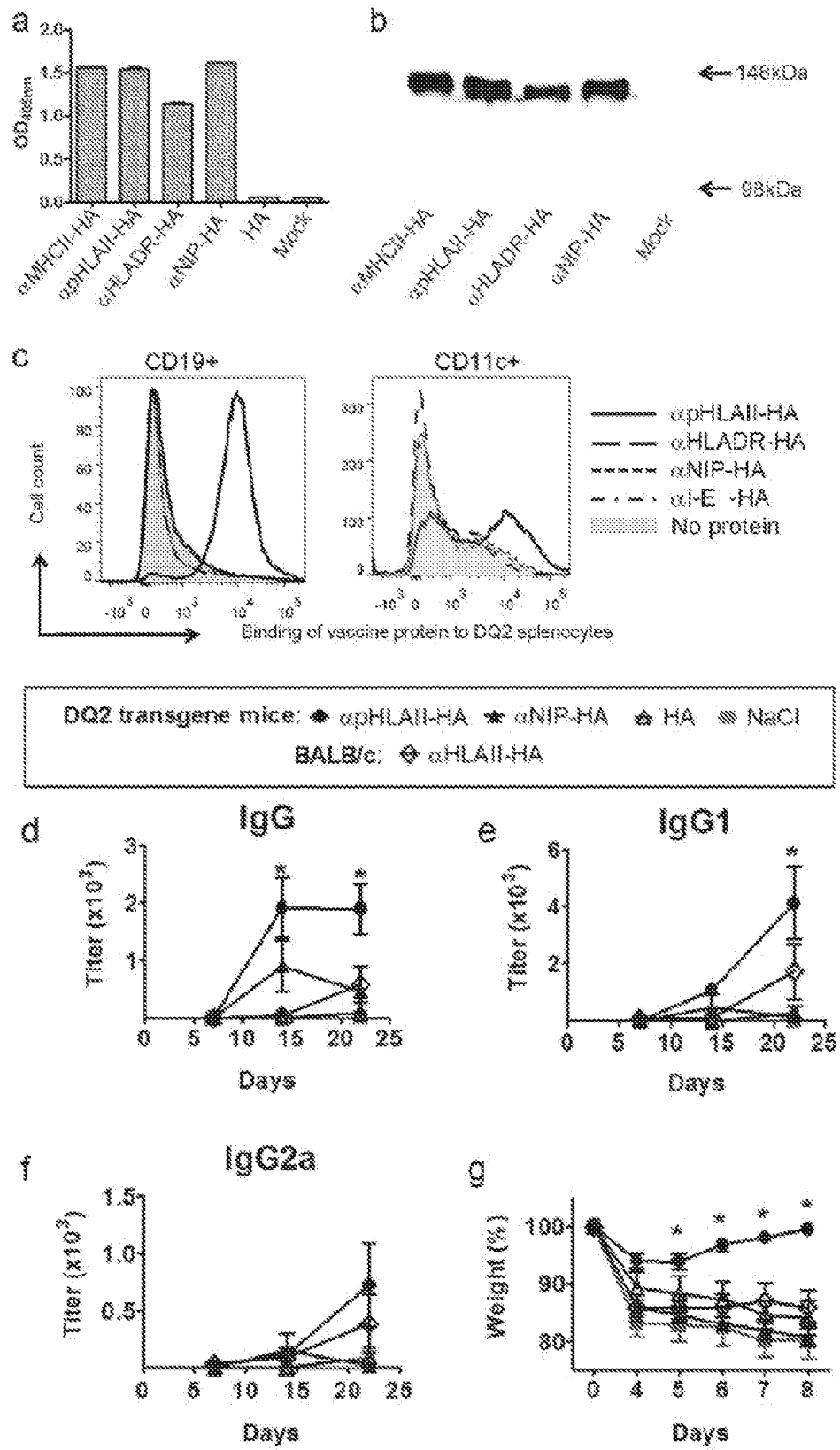
FIG. 4A-G. DNA vaccination with αpHLAII-HA confers protection against influenza challenge in DQ2-transgenic mice. (a) Supernatants from 293E cells transiently transfected with DNA expressing the indicated vaccine proteins were examined for binding to mAb against the dimerization unit (MCA878) in Sandwich ELISA, followed by detection with biotinylated mAb (H36-4-52) directed against HA in the antigenic unit. (b) Western blot of supernatants from transfected 293E cells, detected with anti-HA mAb specific for PR8 HA expressed in the vaccine proteins. Constructs are indicated below lanes, MW by arrows. (c) Binding of indicated vaccine proteins to splenocytes from DQ2-transgenic mice on a BALB/c background. (d-g) Mice were vaccinated once with 25 μg of the indicated DNA plasmids i.d. combined with electroporation (EP). Serum obtained on days 7, 14 and 21 were tested for presence of (d) IgG, (e) IgG1 and (f) IgG2a anti-HA antibodies in ELISA (g) At day 22, mice were challenged i.n. with a lethal dose of influenza PR8 and monitored for weight. In d,e,g, mean±SEM is given (n=6/group), *indicates $p<0.05$ for αpHLAII-HA as compared to all other controls (two-way Anova and Bonferroni post test).

Targeted DNA Vaccine Induce Protection Against Challenge with Influenza Virus in DQ2-Transgene Mice Vaccine plasmids encoding HA and targeting units against pHLAII and HLA-DR (αpHLAII-HA and αHLADR-HA), or non-targeted controls (αNIP-HA and HA alone), were transiently transfected into 293E cells. The secreted vaccine proteins displayed the expected sizes and reactivity with mAbs, as evaluated by ELISAs (FIG. 4a) and Western blotting (FIG. 4b). In accordance with results from the microbead assay (13), αpHLAII-targeted vaccine proteins bound cells from DQ2 transgenic mice (DQA1*05:01/ DQB1*02:01). Consistent with results from human PBMC, the vaccine proteins bound most CD19+ cells and a substantial fraction of CD11c+ splenocytes from DQ2-transgene mice, while αHLADR-HA and αNIP-HA failed to bind (FIG. 4c).

Next, DQ2 transgenic mice were DNA-vaccinated once intradermally (i.d.), immediately followed by skin electroporation to enhance cellular plasmid uptake. A single vaccination with αpHLAII-HA significantly increased the levels of anti HA IgG in sera, compared to the non-targeted controls (αHLADR-HA, αNIP-HA, HA) (FIG. 4d). The strong increase in antibody levels was observed already 14 days after a single DNA immunization, and was particularly pronounced for IgG1 (FIG. 4e), although IgG2a was also clearly increased (FIG. 4f).

Figure 14:
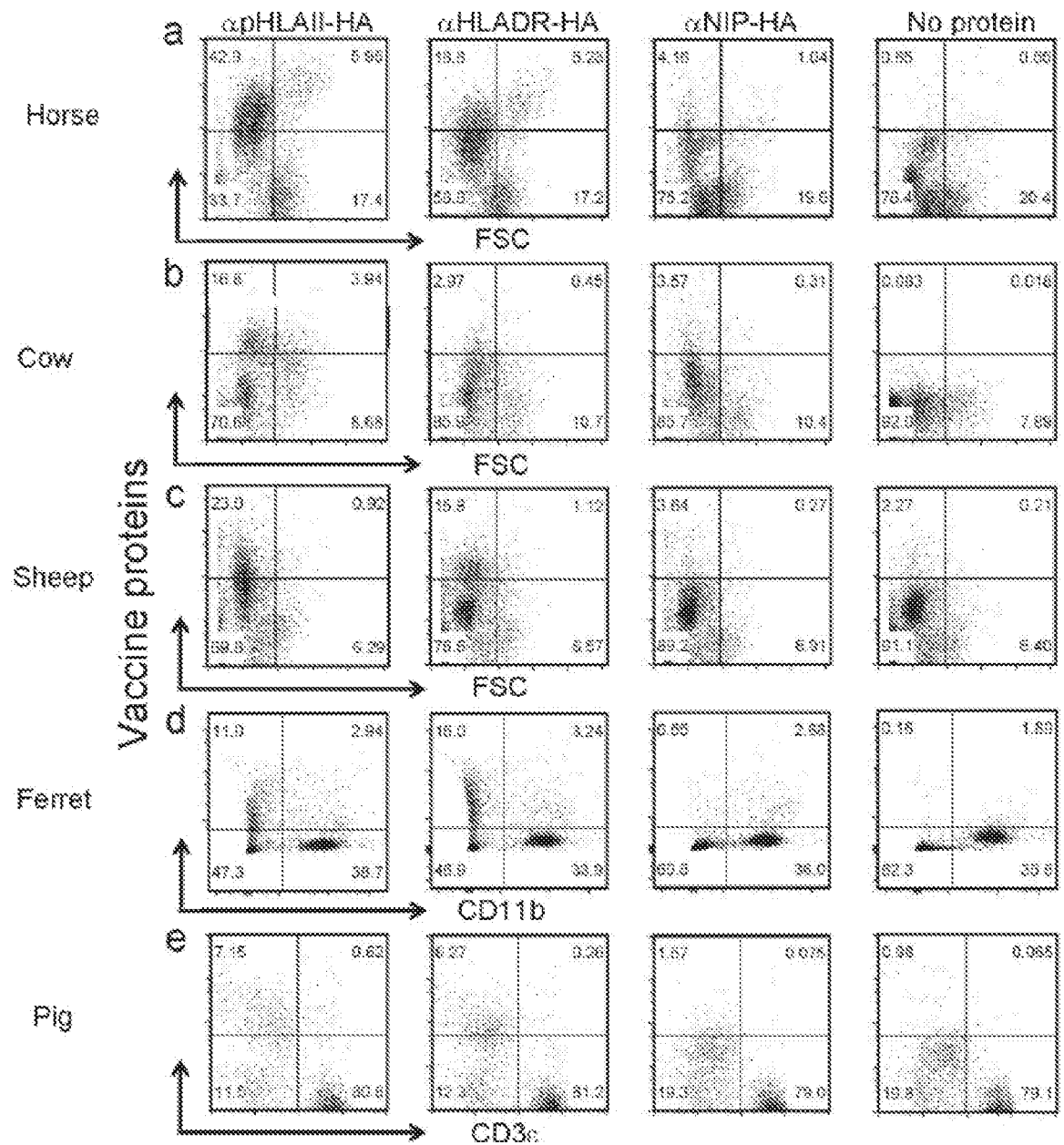
FIG. 14A-E. αpHLAII-HA and αHLADR-HA binds PBMC populations from a number of large animals. (a-e) The indicated vaccine proteins were examined for specific binding to PBMCs from horses (a), cows (b), sheep (c), ferrets (d), and pigs (e). From each specie, staining was performed with PBMC from 3 different individuals, repre-

At day 22 after vaccination, the mice were intra-nasally inoculated with a lethal dose of influenza virus (PR8). Weight monitoring demonstrated that DQ2-transgenic mice vaccinated with αpHLAII-HA were protected against influenza (FIG. 4g). In contrast, DQ2-transgenic mice vaccinated with αNIP-HA or HA alone succumbed to the infection. Protection required expression of DQ2 since nontransgenic BALB/c mice vaccinated with αpHLAII-HA were not protected against an influenza virus challenge. These results demonstrate that the pan HLA-specific HA DNA flu vaccine elicited a protection against viral infection that was contingent upon targeting to HLAII molecules.

αHLAII-Targeted Vaccines Bind MHCII Molecules Expressed in Several Larger Mammals Since the αpHLAII- and αHLADR-targeted vaccine proteins bound a number of different human HLAII molecules, we tested if the vaccine proteins could cross-react with MHCII molecules of larger animals. The αpHLAII-HA bound PBMC from horses, cows, sheep, ferrets and pigs (FIGS. 5*a-b* and 14), whereas αHLADR-HA bound the same species except cows (FIG. 14). The vaccine proteins failed to bind rabbit PBMCs and mouse splenocytes (not shown). A caveat is that a limited number of animals of each species were tested (n=3/specie), therefore, given the polymorphic nature of MHCII molecules, no conclusion about frequencies of binding can be made. In any event, the vaccine proteins are likely to bind a region of the of MHCII molecules that appears conserved between several larger mammals.

Figure 5:
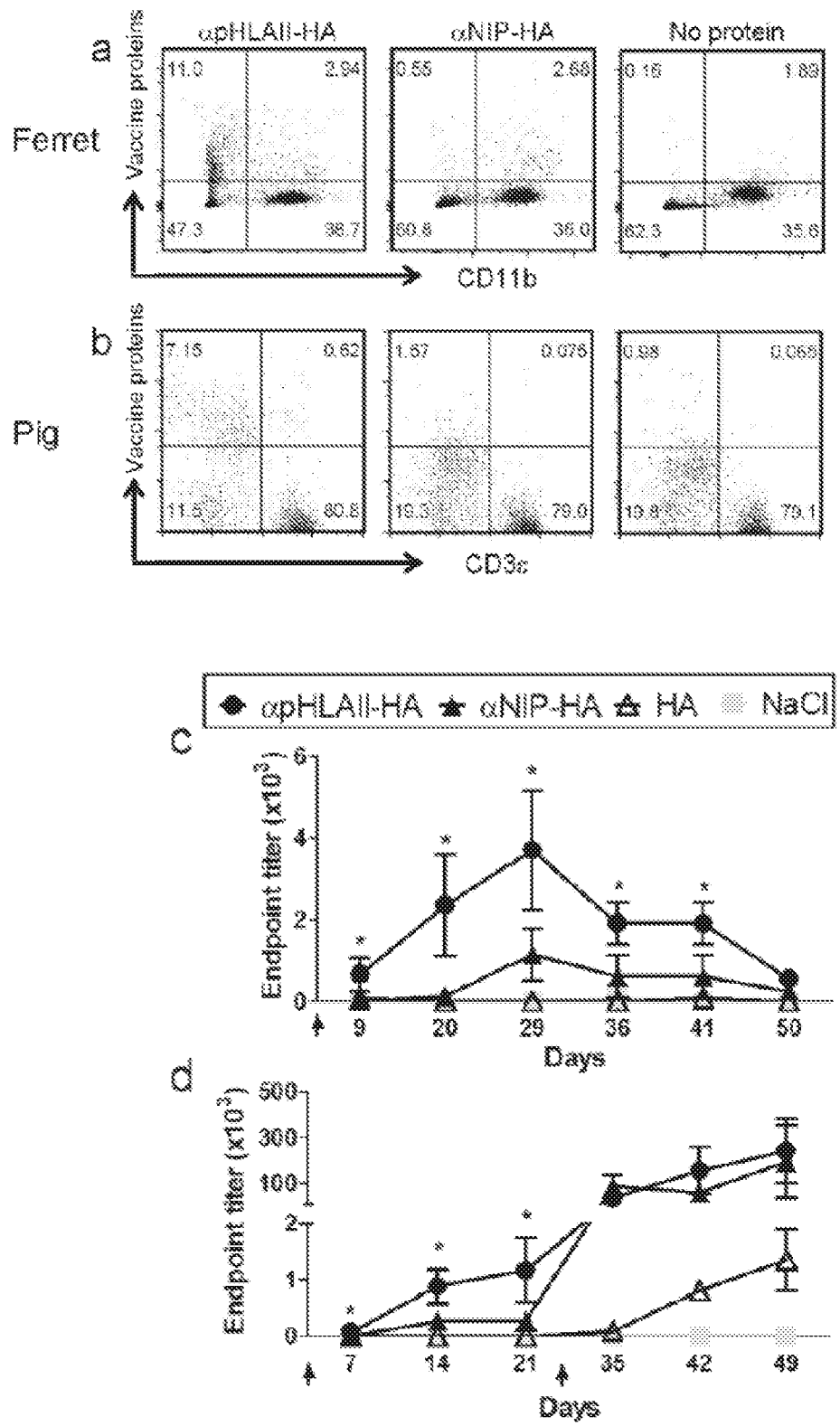
FIG. 5A-E. αpHLAII-HA DNA vaccine increases immune responses in ferrets and pigs. (a, b) The indicated vaccine proteins were examined for specific binding to PBMCs from ferrets (a) and pigs (b). Selection gates for live cells were used on ferret PBMC, whereas an additional gate with CD11R− cells was used for pig PBMCs. Representative images are shown (n=3, both species). (c) Ferrets were immunized once on day 0 with 100 μg DNA i.d./EP. Vaccine constructs are indicated, HA was from A/California/07/2009 (H1N1) (Cal07). Serum samples were tested for IgG against inactivated Cal07 influenza in ELISA (mean±SEM, n=6/group) (*$p<0.05$, two-way Anova). (d) Norwegian farm pigs were immunized on day 0 and boosted on day 21 with 400 μg DNA i.d./EP. Vaccine constructs are indicated, with plasmids encoding HA from Cal07. Sera were assayed for IgG in ELISA (mean+/−SEM, n=6/group) (*$p<0.05$, two-way Anova). (e) Sera harvested at day 21 after first immunization of pigs were assayed in microneutralization assay against influenza Cal07 (mean+/−SEM, n=6/group) (*$p<0.05$, two-way Anova).
Figure 5E:
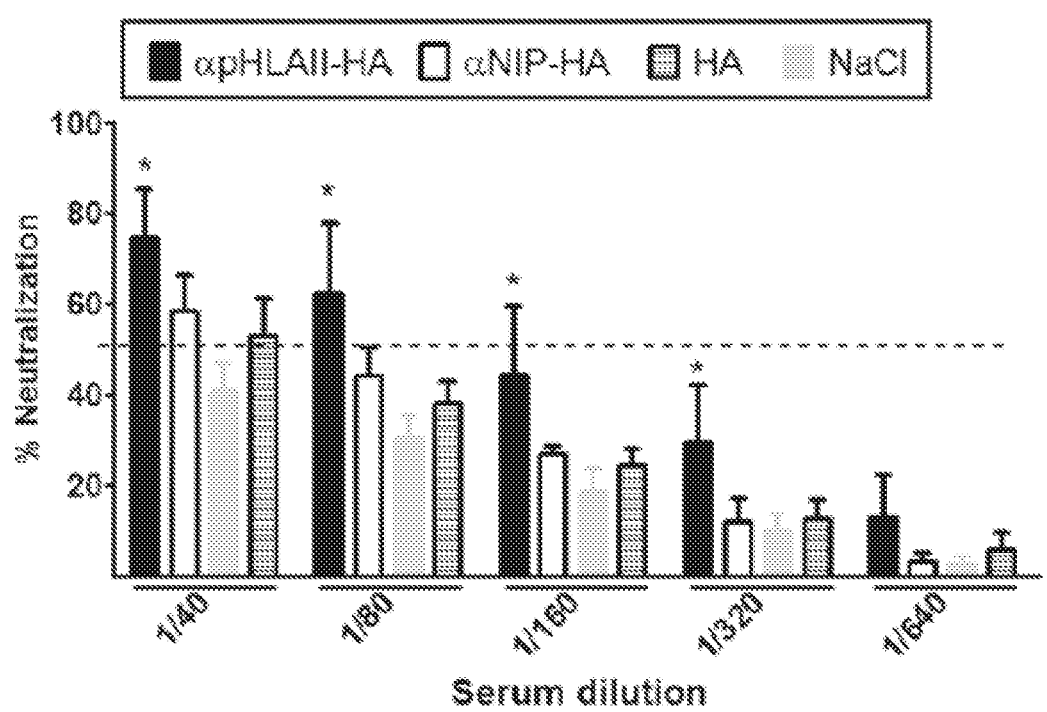
Figure 6:
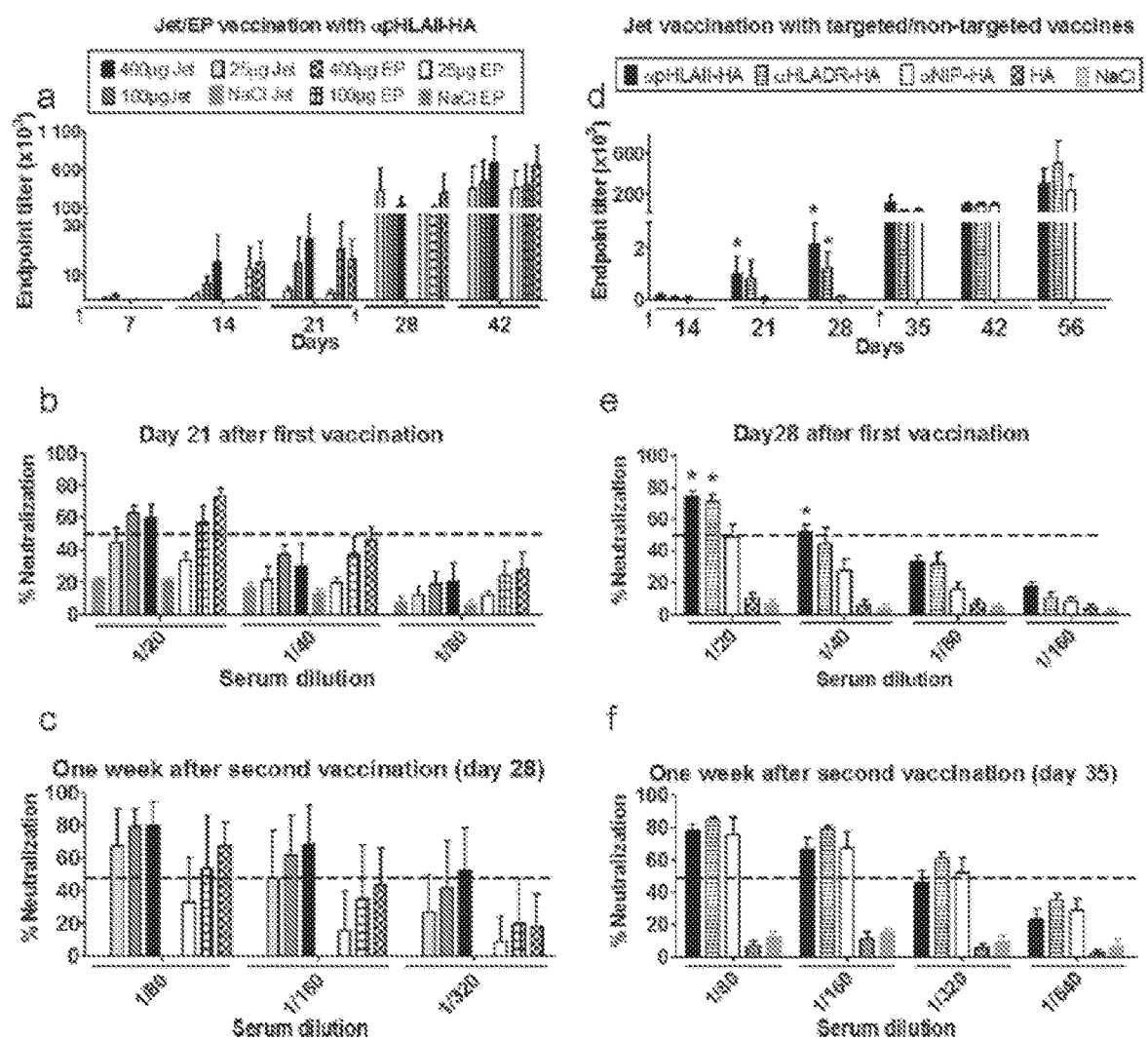
FIG. 6A-F. Painless Jet delivery of DNA vaccine in pigs with maintenance of efficiency and targeting effect (a) Norwegian farm pigs were immunized twice (days 0 and 28,) with indicated amounts of αHLAII-HA (encoding HA from influenza A/PR/8/1934 (H1N1) (PR8)). Vaccination was performed either with DNA delivered i.d./EP, or by needle-free Jet delivery (Jet). Sera were harvested at the indicated time points, and assayed for IgG against inactivated influenza PR8 by ELISA. (b, c) Sera of experiment (a) collected either 21 days after the first vaccination (b), or 1 week after the second vaccination (c), were assayed in micro-neutralization assays against influenza PR8. The dotted lines indicate threshold for positive neutralization. In a-c, n=6/group, mean+/−SEM. (d) Norwegian farm pigs were immunized twice (days 0 and 28,) with 75 μg DNA i.d. by Jet delivery. The indicated constructs expressed HA from PR8 influenza. Sera obtained at the indicated time points were tested for IgG Abs binding HA (PR8). (e, f) Sera of (d) were collected either 28 days after a single vaccination (e), or 1 week after the second vaccination (f), and assayed in micro-neutralization assays against influenza PR8. The dotted lines indicate threshold for positive neutralization. In d-f, n=6/group, mean+/−SEM, *$p<0.05$, two-way Anova.
Figure 9:
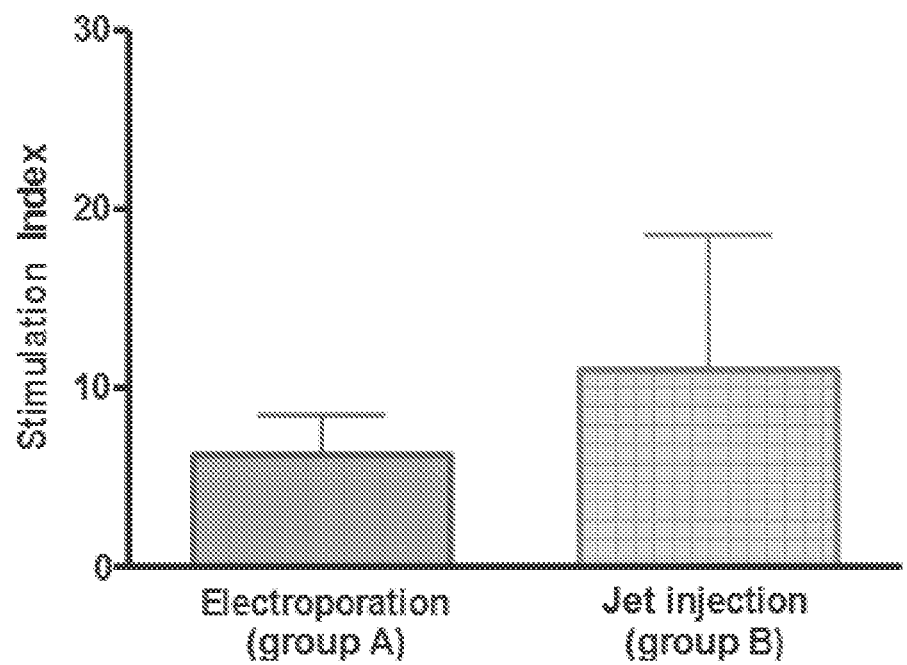
FIG. 9. Antigen specific proliferation following ZEBOV GP stimulation in guinea pig PBMCs. Two groups of six female Hartley guinea pigs each were immunized twice at a three-week interval with αHLAII-GP, via either electroporation (group A) or needle-free jet injection (group B). ZEBOV GP-specific PBMC responses were detected using a 3H-thymidine based cell proliferation assay, following 96 h stimulation with ZEBOV GP. Results are presented as individual Stimulation Indices, indicating the fold change in corrected counts per minute (CCPM) of GP stimulated cells compared to stimulation with medium alone. Samples with CCPM<6000 in ConA-stimulated wells were excluded from analysis. Two tailed t-tests were performed to determine statistical significance between groups at different time points (no significance detected).

Strong Antibody Responses Induced after MHCII-Targeted DNA Vaccination of Ferrets and Pigs Given the staining results, ferrets were DNA-immunized once with 100 μg of plasmids encoding αpHLAII-HA or non-targeted controls (αNIP-HA and HA) (FIG. 5*c*). The DNA was injected i.d., immediately followed by skin electroporation to increase DNA uptake. Ferrets immunized with αpHLAII-HA had serum IgG levels that were significantly increased above that of the control groups (FIG. 5*c*). The elevated antibody levels were evident from day 9, increased until day 29, and then gradually declined.

The weight of a ferret typically is 2-7 kg. In order to assess the vaccine efficacy in animals approaching human sizes, vaccinations were performed in Norwegian farm pigs. Vaccines for DNA immunization of pigs were prepared in the pUMVC vector (29). Similar to ferrets, pigs were in a first experiment immunized with DNA by i.d. injection, immediately followed by skin electroporation. A single DNA immunization with 400 μg αpHLAII-HA was found to significantly increase levels of IgG, as compared to non-targeted controls (αNIP-HA and HA) (FIG. 5*d*). The increase was evident already at day 7, and continued to increase over the next two weeks. Pigs received a second immunization with DNA/electroporation 3 weeks after the first vaccination. The boost greatly enhanced IgG levels in sera. While the first immunization with αNIP-HA failed to induce significant levels of antibodies in sera, the second vaccination increased antibody responses. By contrast, the second immunization did not increase antibody responses to a similar extent in pigs receiving HA alone. Thus, it seems that the bivalent structure of the targeted vaccine positively contributes to the observed immune responses. Importantly, the first immunization with αpHLAII-HA was found to be sufficient for induction of neutralizing antibodies (FIG. 5*e*), which would indicate induction of protective immunity even at this early stage.

Comparison of Electroporation and Jet Delivery after DNA Vaccination in Pigs

The device (Dermavax, Cellectis) which we used for skin electroporation is approved for human use, and represents a well-tolerated system for human vaccination. However, a drawback is that DNA needs to be injected i.d. with a needle and syringe prior to electroporation, and as such presents an obstacle to prophylactic mass vaccination. Thus, we decided to also explore jet delivery of DNA. By jet delivery, drugs are propelled into the skin by high pressure with a handheld mechanical device (42), and the procedure is essentially pain-free.

Pigs were immunized with titrated amounts of αHLAII-HA plasmids, delivered either by jet delivery (Tropis, PharmaJet) or i.d. injection/electroporation (Dermavax, Cellectis). The plasmids were suspended in a 100 μl volume with NaCl. Animals were boosted 3 weeks after the first injection with the same amount of DNA/method, and immune responses monitored by longitudinal measurements of anti-HA IgG in sera (FIG. 6*a*). Results showed that a single vaccination with 100 μg of αpHLAII-HA induced high levels of antibodies after a single vaccination, and that there were no significant magnitudal differences between jet delivery and injection/electroporation. There was a tendency that responses after jet delivery were slightly higher, but the difference was not significant. This tendency also held true after the second vaccination, but both delivery methods greatly enhanced the induced antibody responses. Interestingly, delivery of 25 μg αpHLAII-HA was found sufficient for induction of high antibody levels when delivered twice. These results indicated that in large animals there may be an important dose sparing effect associated with targeting of antigen to MHCII molecules, and that painless and needle-free jet delivery of plasmids may substitute for needle-dependent injection of DNA and electroporation. Both these effects may be of particular importance in the developing world. Firstly, because the dose sparing effect indicates that sufficient amounts of vaccines could be available for the population at large, and, secondly, by allowing for simple, hygenic and painfree vaccine delivery.

MHCII-Targeting Reduces the Amount of DNA Needed for Efficient Vaccination of Pigs Both for EP and jet delivery, there was no significant difference in antibody levels elicited by either 400 μg or 100 μg of DNA. A single delivery of 25 μg DNA resulted in smaller but detectable IgG levels, and the boost increased the anti-HA Ab levels to levels similar to that obtained with either 100 μg or 400 μg of DNA. A more qualitative assessment of the induced antibodies by micro-neutralization assays demonstrated that a single immunization with 100 μg or 400 μg αHLAII-HA (but not 25 μg) was sufficient for induction of neutralizing antibodies (FIG. 6*b*). In correspondence with results from the ELISA assay, titers of neutralizing Abs were enhanced after the boost, and even 25 μg of plasmids encoding αHLAII-HA sufficed for induction of neutralizing antibodies (FIG. 6*c*).

Since the above experiment did not contain non-targeted controls, we did a new experiments where targeted DNA vaccines (upHLAII-HA and αHLADR-HA) were compared with non-targeted vaccines (αNIP-HA and HA alone), employing jet delivery. A single immunization with 75 μg DNA of either αpHLAII-HA or αHLADR-HA significantly enhanced IgG levels above that observed for the non-targeted controls, as detected by ELISA (FIG. 6*d*). A second vaccination on day 28 further boosted responses. Where vaccination with HA alone again failed to significantly improve responses after vaccination, αNIP-HA induced high levels after the second vaccination. This result points towards an added effect from bivalently displayed antigens.

The results obtained with ELISA were corroborated by measurements of neutralizing antibodies in sera after both the first and the second immunization (FIG. 6*e-f*). Importantly, a single vaccination with αpHLAII-HA or αHLADR-HA was sufficient for induction of protective levels of antibodies. The observed differences between MHCII-targeting and the non-targeted controls are consistent with previous observations in mice (23), and indicate that the bivalent vaccine structure in itself enhances immune response, as compared to vaccinations with antigen alone. Moreover, and importantly, these results indicate that a DNA encoded MHCII-targeted vaccine protein can induce clinically relevant antibody responses in 16-30 kg animals, with relatively low amounts (75 μg) and volumes (100 μl) of DNA, even after a single immunization.

Discussion:

DNA vaccination is generally hampered by low immunogenicity, and several injections of large DNA doses are typically required for induction of protective immune responses in larger animals. Here, we have demonstrated that DNA vaccines encoding bivalent fusion proteins that target antigen to MHCII molecules on APC, enhances antibody responses in larger animals such as ferrets and pigs; a single immunization was shown sufficient for induction of antibodies with responses reaching the protective threshold for neutralizing antibodies (FIG. 6e). This may be of great importance if attempting to control an emerging influenza pandemic or other disease outbreak. Antibodies represent a strong correlate of protection against many infectious diseases, and the early antibody formation seen after MHCII-targeting could be useful in many disease scenarios.

While a single immunization with αpHLAII-HA or αHLADR-HA could induce protective levels of antibodies in sera, the efficacy of the non-targeted control, αNIP-HA, was dependent on two successive vaccinations. We also included HA alone as an additional non-targeted control in several experiments. Our data indicated that vaccination with HA alone for protective efficacy would require multiple rounds of immunization, higher DNA doses per round, or the inclusion of an adjuvant. Thus, it seems that the bivalent presentation of antigen, as conferred by the dimerization unit of our vaccine format, in itself may add to the observed immunogenicity. This effect is best explained by the bivalent antigen display allowing some cross-linking of B cell receptors, even in the absence of MHCII-targeting. Nevertheless, our data clearly points to the effect of MHCII-targeting as the decisive factor for strong induction of immune responses, but where antigenic bivalency may confer some improvement of antigen immunogenicity.

It has been suggested that the increased antibody responses observed after MHCII-targeting of antigen may be mediated by vaccine proteins bridging a synapse between APC and B cells (24,45). In such an event, the antigen could bind to B cell receptors (BCR) while the targeting unit secured interaction with the APC, allowing for efficient endocytosis of vaccine antigens and presentation on MHC class II molecules. Thus, in conjunction with T cell help, this can cause efficient stimulation of B cells and increased antibody responses. In the present work, we have not investigated the contribution of T cell responses to formation of immunity. However, we have previously demonstrated in mice that T cells are necessary for formation of antibody responses, and that they can contribute protection in the absence of antibodies (23).

A key feature for a vaccine that is designed to bind human HLAII molecules, is that it efficiently can bind most, if not all, HLAII alleles that are found in the human population. The three most common HLAII alleles are DR2b (DRB1*15:01), DQ2.5 (DQA1*05:01/DQB1*02:01) and DP4.1 (DPA1*01:03/DPB1*04:01), of which the latter is expressed in about 70% of Caucasians. Importantly, there is good correlation between the binding profiles of the HLAII- and HLADR-targeted vaccines, and HLA II prevalence in the human population. αHLADR-CκCκ bound all HLA DR molecules tested (13), whereas αHLAII-CκCκ bound all but two HLA DR molecules (DR1104 and DR1101). DR1104 has a frequency of 0,01780 in the population, and is almost exclusively found in the region around South-Eastern Europe, whereas DRB1*11:01 has a frequency of 0,05945 and typically will be found in Southern Africa or Western Asia (46). However, individuals with these alleles will also display HLA-DQ and HLA-DP molecules that are very likely to be bound by UHLAII-CκCκ (ex. DP0101 or DP0401). In conclusion, the binding profiles of the pHLAII- and HLADR-targeted vaccines indicates that these vaccines find use for vaccinations of the human population.

Previously, we have delivered DNA by intradermal injection immediately followed by skin electroporation to enhance cellular DNA uptake (47,48). While this procedure is approved for use in humans, and typically by vaccines described as "well tolerable", it represents a barrier towards prophylactic immunization of humans. On this background, we compared vaccine delivery by skin injection/electroporation to jet delivery in pigs. Intradermal jet delivery is a pain and needle free delivery method. Results showed that the two methods of delivery can induce similar immune responses in pigs, with a slight improvement in favor of jet delivery. Thus, we have shown that targeting of antigen to human HLAII molecules is a feasible strategy, both in terms of increased immunogenicity conferred by targeting of antigen to MHCII-molecules, and rational vaccine delivery.

Example 2

Based on the rapid spread and devastating impact of the recent Zaire ebola virus (ZEBOV) outbreak, vaccination is considered to be a crucial control measure against future occurrences of this hemorrhagic disease. Humoral immune responses have been shown to be important for vaccine-mediated protection (51), though it is understood that cell-mediated immunity may also play a role, either directly (53) or indirectly by facilitating long-lived protection against viral infection (49). The DNA vaccine platform offers several benefits concerning EBOV vaccination, including the strong induction of CD4+ T cells (52) and the potential to offer a safe priming option to be used in combination with other vaccine platforms (50). DNA vaccines based on the glycoprotein (GP) of EBOV and Marburg virus were recently demonstrated to be safe as well as induce some humoral immune responses following three vaccinations in Ugandan participants; however, no GP-specific antibodies were detected in approximately half of the participants in this phase 1b clinical trial (50). Here, we tested the immunogenicity of a Vaccibody vaccine construct based on ZEBOV-GP administered intramuscularly by electroporation or needle-free jet injection in guinea pigs. We found that regardless of administration method, the Vaccibody ZEBOV-GP construct induced GP-specific IgG and IgA serum antibody responses already two weeks after one immunization in guinea pigs, and that these levels remained high at least six weeks after the second vaccination. Although the neutralizing capability of these antibodies remains to be determined, the speed and duration of this antibody response is encouraging. Furthermore, GP-specific T cell proliferation was detected at 10 weeks following the second vaccination in both groups. Taken together, the Vaccibody ZEBOV-GP construct is a promising vaccine candidate against ZEBOV infection with potential to be administered under field conditions using a needle-free jet injector.

Methods

Animals

Twelve four to six week old female outbred Hartley guinea pigs purchased from Harlan Laboratories (Horst, Netherlands) were randomly divided into two groups of six guinea pigs each and housed in pairs at the Laboratory for Experimental Biomedicine (University of Gothenburg, Sweden). All animals were given free access to pellets and water containing Vitamin C, as well as received daily treats including crisp bread, lettuce, and carrots.

Immunizations

Before vaccination, guinea pigs were anesthetized with isofluorane (Abbott Laboratories Ltd, England) through a face mask according to standard protocols. Animals were immunized with αHLAII-GP twice at a three weeks interval, using either electroporation (group A) or the PharmaJet Stratis® needle free jet injector (PharmaJet, USA; group B). All animals were immunized in the quadriceps muscle of each leg and monitored for local inflammation for three days following each immunization.

Sample Collection

Blood samples for serum isolation were collected from the saphenous veins of all animals at six time points: day 0 (before first immunization), day 14, day 21 (before second immunization), day 28, day 50, and day 63, and day 88 (before euthanization). Sera were isolated using a standard double centrifugation protocol and stored at −20° C. until use. Blood samples for peripheral blood mononuclear cells (PBMCs) were collected on D91 by cardiac puncture of anesthetized animals.

Saliva samples were collected from all animals at D14, D21, and D91 using Weck-Cel® eye spears (Beaver-Visitec International, USA). Briefly, 200 μl of saliva isolation buffer, consisting of 1.5 g NaCl and 10 mg aprotinin in 100 ml PBS, was pipetted onto the cellulose acetate filter of 0.22 μm Corning® CoStar® Spin-X® centrifuge filter tubes. Eye spears were either placed in the guinea pig mouth and held in place for 10 seconds (D14) or the guinea pig mouths were swabbed briefly while animals were under anesthesia (D21, D91), then immediately placed into SIB and stored on ice. Samples were centrifuged at +4° C. for 15 min at 5000×g, the spears and filters removed, and stored at −20° C. until use.

Lung supernatants were obtained from saponin-treated lung tissue samples. Briefly, following euthanization lungs were perfused with PBS, then removed from each animal and placed in 5.6 ml inhibition buffer and stored on ice. BSA (1%) was added to each lung before storage at −20° C. Saponin (10%) was added to each tube and the lungs were stored overnight at +4° C. The next day, the supernatants from all samples were relocated to 10 ml tubes, centrifuged at 4400×g for 10 min, and the supernatant stored at −20° C. until use.

GP Specific IgG Antibody Assessment

An in-house CHO cell-generated His-tagged GP of ZEBOV was used to develop an in house GP specific ELISA. Sera collected at different time points after first and second immunization were subjected individually to the GP-specific ELISA to determine specific IgG antibody titers to ZEBOV-GP. Briefly, 96-well Maxisorp ELISA plates (Nunc, Denmark) were coated overnight at +4° C. with 1 μg/ml EBOV-GP, then incubated for 60 min at room temperature with 1% BSA+PBS-Tween following a PBS wash. The plates were washed with PBS-Tween, incubated for 90 min at room temperature with seven three-fold dilutions of guinea pig sera (1:10 to 1:7290) in blocking buffer, then washed before a final incubation with HRP-conjugated secondary antibody (goat-anti guinea pig IgG, 1:6000 dilution) for 90 min at room temperature. Results were visualized using TMB peridoxase substrate (KPL, USA), stopped with 1M H2SO4, and absorbance measured at 450 nm. Results are expressed as log 10-transformed antibody titers, calculated by linear regression to the negative cut off, defined as the average OD value of blank wells plus 3 times the standard deviation of those blank wells.

GP-Specific IgA Antibody Assessment

An in house CHO cell generated His tagged ZEBOV GP was used to develop an in house GP specific ELISA. Sera, saliva, or lung supernatants collected at different time points were subjected individually to the GP specific ELISA to determine specific IgA antibody titers to ZEBOV GP. Briefly, 96 well Maxisorp ELISA plates (Nunc, Denmark) were coated overnight at +4° C. with 1 μg/ml ZEBOV GP, then incubated for 4 h at room temperature with 5% skim milk in PBS Tween following a PBS wash. The plates were washed with PBS Tween, incubated for 2 h min at room temperature with 4 6 three fold dilutions of guinea pig sera, saliva, or lung supernatants (1:10 to 1:2430; 1:5 to 1:135; and 1:5 to 1:1215, respectively) in blocking buffer, then washed before a final incubation with HRP conjugated goat anti guinea pig IgA (1:4000 dilution; AbDSerotec, UK) for 90 min at room temperature. Results were visualized using TMB peridoxase substrate (KPL, USA), stopped with 1M H2SO4, and absorbance measured at 450 nm. Results are expressed as log 10 transformed antibody titers, calculated by linear regression to the OD value of the previously defined negative cut off.

ZEBOV GP Specific PBMC Proliferation Analysis

Blood samples for PBMC isolation was collected using a 10 ml syringe into individual 50 ml tubes containing heparin, then immediately diluted 1:1 with room temperature PBS. PBMCs were isolated by FICOLL Paque gradient and washed twice in PBS before diluting in complete Iscove's medium (Life Technologies, USA) including 10% fetal bovine serum and 1% each of R mercaptoethanol, L glutamine, and gentamicin. Cells were counted, plated in flat bottomed 96 well plates at 200,000 cells/well, and stimulated in triplicate with either 4 μg/well ZEBOV GP, 5 μg/well Concavalin A (ConA), or medium alone. Plates were incubated at 37° C. with 5% C02 for 96 h, then 60 μl of supernatant removed per well and 20 μl of thymidine, diluted 1:20 in complete Iscove's medium, was added to each well and incubated for an additional 7 h at 37° C. Cells were harvested using a Cell Harvester (Tomtec, USA) and counted using a MicroBeta plate counter (Perkin Elmer, USA) according to standard protocols. Stimulation indices indicating fold changes of PBMC proliferation compared to medium alone, were determined by dividing the average corrected count per minute (CCPM) of GP or ConA stimulated wells by that of wells containing no stimulant. Only samples with an average CCPM greater than 6000 in ConA stimulated wells were included in GP specific PBMC proliferation analyses.

Statistics

Two-way ANOVA tests or two tailed t tests were performed among groups at the different time points or between groups at the same time point, using Prism 6.0 (GraphPad, USA), to determine statistical significance based on a p value less than 0.05.

Results

Figures 7, 8:
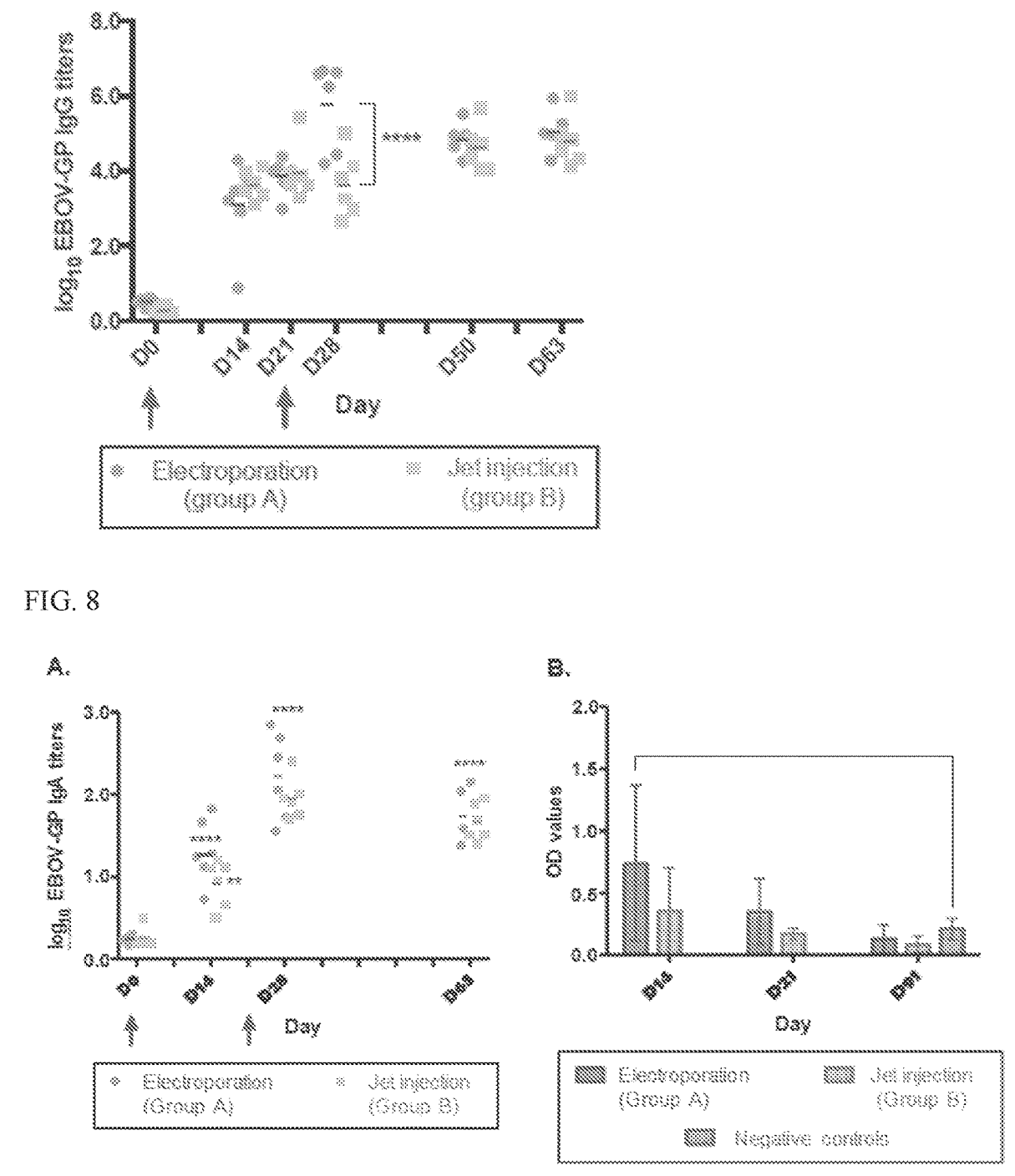

HLAII-targeted GP construct elicits strong ZEBOV GP specific IgG serum antibody responses by both electroporation and jet injection ZEBOV GP specific IgG antibody responses were detected in the sera of 5/6 immunized animals in group A and 6/6 immunized animals in group B two weeks after the first immunization (day 14, FIG. 7). One week following the second immunization, specific antibodies were detected in the sera of all immunized guinea pigs at levels that were significantly higher in group A compared to group B. However, by day 50, no significant differences were observed between groups and antibody levels remained elevated at least through day 63 (last time point tested), at approximately 5 log 10 titer for both groups.

HLAII-Targeted GP Construct Induces Long Lasting ZEBOV GP Specific Systemic, but not Mucosal, IgA Antibody Responses by Both Electroporation and Jet Injection Sera, saliva, and lung supernatants from all vaccinated animals were collected and subjected to an in house ELISA, to determine systemic (serum) or mucosal (saliva, lung supernatants) IgA antibody responses following vaccination with the HLAII-targeted GP construct. IgA antibody responses in serum increased in all vaccinated individuals at two weeks after the first vaccination (day 14, FIG. 8A) and continued to increase one week after the second vaccination in both groups at levels that were statistically significant compared to day 0 ($p<0.0001$ for both groups). These GP specific antibody titers peaked at day 28 at approximately 2 log 10 titer. At five weeks following the second vaccination (day 63), levels had decreased compared to day 28, but remained statistically significant compared to day 0 ($p<0.001$) in both groups.

ZEBOV GP specific IgA antibodies were also detected at low levels in saliva samples collected from vaccinated guinea pigs (FIG. 2B), but not in lung supernatants (data not shown). These levels were highest at two weeks after first vaccination (day 14) and were significant in the electroporation group compared to negative controls at this time point ($p<0.01$), but decreased before second vaccination and remained at similar levels to the negative controls at the end of the study (day 91).

HLAII-Targeted GP Construct Stimulates Specific PBMC Proliferation by Both Electroporation and Jet Injection PBMCs isolated from vaccinated guinea pigs were stimulated for 96 h with ZEBOV GP and their proliferation measured using a 3H thymidine based assay in comparison with medium alone. Both groups of vaccinated animals showed a marked increase in PBMC proliferation following GP stimulation, which averaged 6 fold and 11 fold higher than medium alone in the electroporation and jet injection groups, respectively. Two of 6 individuals in the electroporation group and 3/6 in the jet injection group were excluded from analyses based on low relative proliferation following ConA stimulation, and therefore a small number of animals were included in the analysis. However, the same relative pattern of GP specific proliferation (higher in the jet injection group than the electroporation group) is shown with all data points included. Therefore, although these results were not statistically significant, they suggest that the jet injection method may induce greater PBMC proliferation following GP specific stimulation compared to the electroporation administration.

CONCLUSIONS

The rapid yet long lasting IgG antibody responses induced by either administration method of this novel vaccine construct are encouraging, especially with the critical importance of a GP specific humoral response against ZEBOV infection. However, the functionality of these antibody responses remains to be determined.

Although high levels of IgA antibodies were not detected in saliva, our results indicate that some antibodies were detected in some individuals following intramuscular vaccination of the construct.

Cell mediated immune responses, as measured by GP specific PBMC proliferation, were detected at 10 weeks following the second vaccination and were higher in the jet injection group, albeit not significantly.

Although the primary focus for vaccine induced protection against EBOV infection is a strong humoral immune response, other studies have shown that cell mediated immunity may also play a role either directly or indirectly (53, 49). Therefore, the results presented herein are relevant, and important, in the context of generating novel EBOV vaccine candidates.

REFERENCES

1. Koff, W. C., D. R. Burton, P. R. Johnson, B. D. Walker, C. R. King, G. J. Nabel, R. Ahmed, M. K. Bhan, and S. A. Plotkin. 2013. Accelerating next-generation vaccine development for global disease prevention. Science 340: 1232910.
2. Bergman, P. J., M. A. Camps-Palau, J. A. McKnight, N. F. Leibman, D. M. Craft, C. Leung, J. Liao, I. Riviere, M. Sadelain, A. E. Hohenhaus, P. Gregor, A. N. Houghton, M. A. Perales, and J. D. Wolchok. 2006. Development of a xenogeneic DNA vaccine program for canine malignant melanoma at the Animal Medical Center. Vaccine 24: 4582-4585.
3. Davis, B. S., G. J. Chang, B. Cropp, J. T. Roehrig, D. A. Martin, C. J. Mitchell, R. Bowen, and M. L. Bunning. 2001. West Nile virus recombinant DNA vaccine protects mouse and horse from virus challenge and expresses in vitro a noninfectious recombinant antigen that can be used in enzyme-linked immunosorbent assays. J. Virol. 75: 4040-4047.
4. Kawamura, H., and J. A. Berzofsky. 1986. Enhancement of antigenic potency in vitro and immunogenicity in vivo by coupling the antigen to anti-immunoglobulin. J. Immunol. 136: 58-65.
5. Carayanniotis, G., and B. H. Barber. 1987. Adjuvant-free IgG responses induced with antigen coupled to antibodies against class II MHC. Nature 327: 59-61.
6. Snider, D. P., and D. M. Segal. 1987. Targeted antigen presentation using crosslinked antibody heteroaggregates. J. Immunol. 139: 1609-1616.
7. Baier, G., G. Baier-Bitterlich, D. J. Looney, and A. Altman. 1995. Immunogenic targeting of recombinant peptide vaccines to human antigen-presenting cells by chimeric anti-HLA-DR and anti-surface immunoglobulin D antibody Fab fragments in vitro. J. Virol. 69: 2357-2365.
8. Biragyn, A., K. Tani, M. C. Grimm, S. Weeks, and L. W. Kwak. 1999. Genetic fusion of chemokines to a self tumor antigen induces protective, T-cell dependent antitumor immunity. Nat. Biotechnol. 17: 253-258.
9. Bonifaz, L., D. Bonnyay, K. Mahnke, M. Rivera, M. C. Nussenzweig, and R. M. Steinman. 2002. Efficient targeting of protein antigen to the dendritic cell receptor DEC-205 in the steady state leads to antigen presentation on major histocompatibility complex class I products and peripheral CD8+ T cell tolerance. J. Exp. Med. 196: 1627-1638.
10. Lunde, E., L. A. Munthe, A. Vabo, I. Sandlie, and B. Bogen. 1999. Antibodies engineered with IgD specificity efficiently deliver integrated T-cell epitopes for antigen presentation by B cells. Nat. Biotechnol. 17: 670-675.
11. Caminschi, I., A. I. Proietto, F. Ahmet, S. Kitsoulis, T. J. Shin, J. C. Lo, A. Rizzitelli, L. Wu, D. Vremec, S. L. van Dommelen, I. K. Campbell, E. Maraskovsky, H. Braley, G. M. Davey, P. Mottram, d. van, V, K. Jensen, A. M. Lew, M. D. Wright, W. R. Heath, K. Shortman, and M. H.

Lahoud. 2008. The dendritic cell subtype-restricted C-type lectin Clec9A is a target for vaccine enhancement. Blood 112: 3264-3273.
12. Charalambous, A., M. Oks, G. Nchinda, S. Yamazaki, and R. M. Steinman. 2006. Dendritic cell targeting of survivin protein in a xenogeneic form elicits strong CD4+ T cell immunity to mouse survivin. J. Immunol. 177: 8410-8421.
13. Estrada, A., M. R. McDermott, B. J. Underdown, and D. P. Snider. 1995. Intestinal immunization of mice with antigen conjugated to anti-MHC class II antibodies. Vaccine 13: 901-907.
14. Mjaaland, S., and S. Fossum. 1990. Modulation of immune responses with monoclonal antibodies. I. Effects on regional lymph node morphology and on anti-hapten responses to haptenized monoclonal antibodies. Eur. J. Immunol. 20: 1457-1461.
15. Skea, D. L., A. R. Douglas, J. J. Skehel, and B. H. Barber. 1993. The immunotargeting approach to adjuvant-independent immunization with influenza haemagglutinin. Vaccine 11: 994-1002.
16. Lees, A., S. C. Morris, G. Thyphronitis, J. M. Holmes, J. K. Inman, and F. D. Finkelman. 1990. Rapid stimulation of large specific antibody responses with conjugates of antigen and anti-IgD antibody. J. Immunol. 145: 3594-3600.
17. Fredriksen, A. B., I. Sandlie, and B. Bogen. 2006. DNA vaccines increase immunogenicity of idiotypic tumor antigen by targeting novel fusion proteins to antigen-presenting cells. Mol. Ther. 13: 776-785.
18. Schjetne, K. W., A. B. Fredriksen, and B. Bogen. 2007. Delivery of antigen to CD40 induces protective immune responses against tumors. J. Immunol. 178: 4169-4176.
19. Fossum, E., G. Grodeland, D. Terhorst, A. A. Tveita, E. Vikse, S. Mjaaland, S. Henri, B. Malissen, and B. Bogen. 2015. Vaccine molecules targeting Xcr1 on cross-presenting DCs induce protective CD8(+) T-cell responses against influenza virus. Eur. J. Immunol. 45: 624-635.
20. Fredriksen, A. B., and B. Bogen. 2007. Chemokine-idiotype fusion DNA vaccines are potentiated by bivalency and xenogeneic sequences. Blood 110: 1797-1805.
21. Grodeland, G., E. Fossum, and B. Bogen. 2015. Polarizing T and B Cell Responses by APC-Targeted Subunit Vaccines. Front Immunol. 6: 367.
22. Grodeland, G., S. Mjaaland, G. Tunheim, A. B. Fredriksen, and B. Bogen. 2013. The specificity of targeted vaccines for APC surface molecules influences the immune response phenotype. PLoS. One. 8: e80008.
23. Grodeland, G., S. Mjaaland, K. H. Roux, A. B. Fredriksen, and B. Bogen. 2013. DNA vaccine that targets hemagglutinin to MHC class II molecules rapidly induces antibody-mediated protection against influenza. J. Immunol. 191: 3221-3231.
24. Grodeland, G., and B. Bogen. 2015. Efficient vaccine against pandemic influenza: combining DNA vaccination and targeted delivery to MHC class II molecules. Expert. Rev. Vaccines. 14: 805-814.
25. Schjetne, K. W., K. M. Thompson, T. Aarvak, B. Fleckenstein, L. M. Sollid, and B. Bogen. 2002. A mouse C kappa-specific T cell clone indicates that DC-SIGN is an efficient target for antibody-mediated delivery of T cell epitopes for MHC class II presentation. Int. Immunol. 14: 1423-1430.
26. Holte, H., H. K. Blomhoff, K. Beiske, S. Funderud, P. Torjesen, G. Gaudernack, T. Stokke, and E. B. Smeland. 1989. Intracellular events associated with inhibition of B cell activation by monoclonal antibodies to HLA class II antigens. Eur. J. Immunol. 19: 1221-1225.
27. Lampson, L. A., and R. Levy. 1980. Two populations of Ia-like molecules on a human B cell line. J. Immunol. 125: 293-299.
28. Norderhaug, L., T. Olafsen, T. E. Michaelsen, and I. Sandlie. 1997. Versatile vectors for transient and stable expression of recombinant antibody molecules in mammalian cells. J. Immunol. Methods 204: 77-87.
29. Stewart, S. A., D. M. Dykxhoorn, D. Palliser, H. Mizuno, E. Y. Yu, D. S. An, D. M. Sabatini, I. S. Chen, W. C. Hahn, P. A. Sharp, R. A. Weinberg, and C. D. Novina. 2003. Lentivirus-delivered stable gene silencing by RNAi in primary cells. RNA. 9: 493-501.
30. Staudt, L. M., and W. Gerhard. 1983. Generation of antibody diversity in the immune response of BALB/c mice to influenza virus hemagglutinin. I. Significant variation in repertoire expression between individual mice. J. Exp. Med. 157: 687-704.
31. Yelton, D. E., C. Desaymard, and M. D. Scharff 1981. Use of monoclonal anti-mouse immunoglobulin to detect mouse antibodies. Hybridoma 1: 5-11.
32. Du Pre, M. F., A. E. Kozijn, L. A. van Berkel, M. N. ter Borg, D. Lindenbergh-Kortleve, L. T. Jensen, Y. Kooy-Winkelaar, F. Koning, L. Boon, E. E. Nieuwenhuis, L. M. Sollid, L. Fugger, and J. N. Samsom. 2011. Tolerance to ingested deamidated gliadin in mice is maintained by splenic, type 1 regulatory T cells. Gastroenterology 141: 610-20, 620.
33. Larkin, M. A., G. Blackshields, N. P. Brown, R. Chenna, P. A. McGettigan, H. McWilliam, F. Valentin, I. M. Wallace, A. Wilm, R. Lopez, J. D. Thompson, T. J. Gibson, and D. G. Higgins. 2007. Clustal W and Clustal X version 2.0. Bioinformatics. 23: 2947-2948.
34. Nicholas, K. B., H. B. Jr. Nicholas, and D. W. II. Deerfield. 1997. GeneDoc: analysis and visualization of genetic variation. EMBNEW News 4.
35. Baker, N. A., D. Sept, S. Joseph, M. J. Holst, and J. A. McCammon. 2001. Electrostatics of nanosystems: application to microtubules and the ribosome. Proc. Natl. Acad. Sci. U. S. A 98: 10037-10041.
36. Nepom, B. S., G. T. Nepom, M. Coleman, and W. W. Kwok. 1996. Critical contribution of beta chain residue 57 in peptide binding ability of both HLA-DR and -DQ molecules. Proc. Natl. Acad. Sci. U. S. A 93: 7202-7206.
37. Tunheim, G., K. M. Thompson, A. B. Fredriksen, T. Espevik, K. W. Schjetne, and B. Bogen. 2007. Human receptors of innate immunity (CD14, TLR2) are promising targets for novel recombinant immunoglobulin-based vaccine candidates. Vaccine 25: 4723-4734.
38. Robinson, J., J. A. Halliwell, J. D. Hayhurst, P. Flicek, P. Parham, and S. G. Marsh. 2015. The IPD and IMGT/HLA database: allele variant databases. Nucleic Acids Res. 43: D423-D431.
39. Maiers, M., L. Gragert, and W. Klitz. 2007. High-resolution HLA alleles and haplotypes in the United States population. Hum. Immunol. 68: 779-788.
40. Silver, J., and S. Ferrone. 1979. Structural polymorphism of human DR antigens. Nature 279: 436-437.
41. Schjetne, K. W., K. M. Thompson, N. Nilsen, T. H. Flo, B. Fleckenstein, J. G. Iversen, T. Espevik, and B. Bogen. 2003. Cutting edge: link between innate and adaptive immunity: Toll-like receptor 2 internalizes antigen for presentation to CD4+ T cells and could be an efficient vaccine target. J. Immunol. 171: 32-36.
42. Logomasini, M. A., R. R. Stout, and R. Marcinkoski. 2013. Jet injection devices for the needle-free administration of compounds, vaccines, and other agents. Int. J. Pharm. Compd 17: 270-280.
43. Butler, J. E., J. Sun, N. Wertz, and M. Sinkora. 2006. Antibody repertoire development in swine. Dev. Comp Immunol. 30: 199-221.
44. Kacskovics, I., J. Sun, and J. E. Butler. 1994. Five putative subclasses of swine IgG identified from the cDNA sequences of a single animal. J. Immunol. 153: 3565-3573.
45. Batista, F. D., and N. E. Harwood. 2009. The who, how and where of antigen presentation to B cells. Nat. Rev. Immunol. 9: 15-27.
46. Solberg, O. D., S. J. Mack, A. K. Lancaster, R. M. Single, Y. Tsai, A. Sanchez-Mazas, and G. Thomson. 2008. Balancing selection and heterogeneity across the classical human leukocyte antigen loci: a meta-analytic review of 497 population studies. Hum. Immunol. 69: 443-464.
47. Roos, A. K., F. Eriksson, J. A. Timmons, J. Gerhardt, U. Nyman, L. Gudmundsdotter, A. Brave, B. Wahren, and P. Pisa. 2009. Skin electroporation: effects on transgene expression, DNA persistence and local tissue environment. PLoS. One. 4: e7226.
48. Roos, A. K., F. Eriksson, D. C. Walters, P. Pisa, and A. D. King. 2009. Optimization of skin electroporation in mice to increase tolerability of DNA vaccine delivery to patients. Mol. Ther. 17: 1637-1642.
49. Blaney, J. E. et al., 2013. Antibody Quality and Protection from Lethal Ebola Virus Challenge in Nonhuman Primates Immunized with Rabies Virus Based Bivalent Vaccine. *PLoS Pathogens*, 9(5). Available at: ncbi.nlm-.nih.gov/pmc/articles/PMC3667758/[Accessed Jun. 9, 2015].
50. Kibuuka, H. et al., 2015. Safety and immunogenicity of Ebola virus and Marburg virus glycoprotein DNA vaccines assessed separately and concomitantly in healthy Ugandan adults: a phase 1b, randomised, double-blind, placebo-controlled clinical trial. *Lancet* (London, England), 385(9977), pp. 1545-1554.
51. Marzi, A. et al., 2013. Antibodies are necessary for rVSV/ZEBOV-GP-mediated protection against lethal Ebola virus challenge in nonhuman primates. *Proceedings of the National Academy of Sciences of the United States of America,* 110(5), pp. 1893-1898.
52. Stanley, D. A. et al., 2014. Chimpanzee adenovirus vaccine generates acute and durable protective immunity against ebolavirus challenge. *Nature Medicine,* 20(10), pp. 1126-1129.
53. Sullivan, N.J. et al., 2011. CD8+ cellular immunity mediates rAd5 vaccine protection against Ebola virus infection of nonhuman primates. *Nature Medicine,* 17(9), pp. 1128-1131.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

What is claimed is:

1. A nucleic acid comprising a sequence encoding an antibody, a scFv or a Fab fragment comprising light chain complementarity determining region (LCDR) 1 of SEQ ID NO:4; LCDR 2 of SEQ ID NO:5; and LCDR 3 of SEQ ID NO:6; and heavy chain complementarity determining region (HCDR) 1 of SEQ ID NO:7; HCDR 2 of SEQ ID NO:8 and; HDCR 3 of SEQ ID NO:9.

2. The nucleic acid of claim 1, further comprising a sequence encoding an antigen.

3. The nucleic acid of claim 1, further comprising a sequence encoding at least two distinct antigens.

4. The nucleic acid of claim 2, wherein antigen is derived from a pathogenic microorganism.

5. The nucleic acid of claim 4, wherein said pathogenic microorganism is influenza virus or Ebola virus.

6. The nucleic acid of claim 2, wherein said nucleic acid further comprises a linker sequence between said sequence encoding an antigen and said nucleic acid comprising a sequence encoding an antibody, a scFv or a Fab fragment.

7. The nucleic acid of claim 6, wherein said linker comprises a dimerization unit comprising a hinge region from an immunoglobulin and an immunoglobulin constant region.

8. The nucleic acid of claim 7, wherein said linker is a dimerization unit derived from a natural protein.

9. A pharmaceutical composition, comprising: the nucleic acid of claim 1 and a pharmaceutically acceptable carrier.

10. The composition of claim 9, wherein said composition further comprises an adjuvant.

11. The nucleic acid of claim 1, wherein the nucleic acid encodes the polypeptide of SEQ ID NO:1.

12. The nucleic acid of claim 4, wherein said pathogenic microorganism is selected from the group consisting of orthomyxoviruses, paramyxoviruses, adenoviruses, rhinoviruses, coronaviruses, reoviruses, togaviruses, parvoviruses, poxviruses, enteroviruses, hepatitis viruses, herpesviruses, rotaviruses, Norwalk viruses, hantavirus, arenavirus, rhabdovirus, retroviruses, papovaviruses, polyomaviruses, picornaviruses, Dengue virus, Filoviruses, Hantavirus, Rift Valley virus, HHV-8, Human papillomavirus, Bovine leukemia virus, Influenza virus, Guanarito virus, Lassa virus, Measles virus, Rubella virus, Mumps virus, Chickenpox, Monkey pox, Epstein Bahr virus, Parvovirus B 19, Hantaan virus, Sin Nombre virus, Venezuelan equine encephalitis, Sabia virus, West Nile virus and Yellow Fever virus.

* * * * *

SEQUENCE LISTING

```
<160> NUMBER OF SEQ ID NOS: 27

<210> SEQ ID NO 1
<211> LENGTH: 909
<212> TYPE: PRT
<213> ORGANISM: Artificial sequence
<220> FEATURE:
<223> OTHER INFORMATION: synthetic

<400> SEQUENCE: 1

Gln Thr Thr Ser Ser Leu Ser Ala Ser Leu Gly Asp Arg Val Thr Ile
1               5                   10                  15

Ser Cys Ser Ala Ser Gln Asp Ile Asn Asn Tyr Leu Asn Trp Tyr Gln
            20                  25                  30

Gln Lys Pro Asp Gly Thr Val Lys Leu Leu Ile Tyr Tyr Thr Ser Ser
        35                  40                  45

Leu His Ser Gly Val Pro Ser Arg Phe Ser Gly Ser Gly Ser Gly Thr
    50                  55                  60

Asp Tyr Ser Leu Thr Ile Ser Asn Leu Glu Pro Glu Asp Ile Ala Thr
65                  70                  75                  80

Tyr Tyr Cys Gln Gln Tyr Ser Lys Phe Pro Arg Thr Phe Gly Gly Gly
                85                  90                  95

Thr Lys Leu Glu Ile Lys Arg Gly Gly Gly Ser Gly Gly Gly Gly
            100                 105                 110

Ser Gly Gly Gly Gly Ser Gln Ile Gln Leu Val Gln Ser Gly Pro Glu
        115                 120                 125

Leu Lys Lys Pro Gly Glu Thr Val Lys Ile Ser Cys Lys Ala Ser Gly
    130                 135                 140
```

```
Tyr Thr Phe Ile Asn Tyr Gly Met Asn Trp Val Lys Gln Thr Pro Gly
145                 150                 155                 160

Lys Gly Leu Lys Trp Met Gly Trp Ile Asn Thr Tyr Ser Gly Glu Pro
            165                 170                 175

Thr Tyr Pro Asp Asp Phe Lys Gly Arg Phe Ala Phe Ser Leu Glu Thr
        180                 185                 190

Ser Ala Ser Thr Ala Tyr Leu Gln Leu Asn Asn Leu Lys Asn Glu Asp
        195                 200                 205

Met Ala Thr Tyr Phe Cys Ala Arg Gly Asp Tyr Tyr Gly Pro Phe Asp
210                 215                 220

Asn Trp Gly Gln Gly Thr Thr Leu Thr Val Ser Ser Glu Leu Lys Thr
225                 230                 235                 240

Pro Leu Gly Asp Thr Thr His Thr Glu Pro Lys Ser Cys Asp Thr Pro
                245                 250                 255

Pro Pro Cys Pro Arg Cys Pro Gly Gly Ser Ser Gly Gly Gly Ser
            260                 265                 270

Gly Gly Gln Pro Arg Glu Pro Gln Val Tyr Thr Leu Pro Pro Ser Arg
        275                 280                 285

Glu Glu Met Thr Lys Asn Gln Val Ser Leu Thr Cys Leu Val Lys Gly
        290                 295                 300

Phe Tyr Pro Ser Asp Ile Ala Val Glu Trp Glu Ser Gly Gln Pro
305                 310                 315                 320

Glu Asn Asn Tyr Asn Thr Thr Pro Pro Met Leu Asp Ser Asp Gly Ser
                325                 330                 335

Phe Phe Leu Tyr Ser Lys Leu Thr Val Asp Lys Ser Arg Trp Gln Gln
            340                 345                 350

Gly Asn Ile Phe Ser Cys Ser Val Met His Glu Ala Leu His Asn Arg
            355                 360                 365

Phe Thr Gln Lys Ser Leu Ser Leu Ser Pro Gly Lys Gly Leu Gly Gly
    370                 375                 380

Leu Arg Asp Thr Ile Cys Ile Gly Tyr His Ala Asn Asn Ser Thr Asp
385                 390                 395                 400

Thr Val Asp Thr Val Leu Glu Lys Asn Val Thr Val Thr His Ser Val
                405                 410                 415

Asn Leu Leu Glu Asp Ser His Asn Gly Lys Leu Cys Arg Leu Lys Gly
                420                 425                 430

Ile Ala Pro Leu Gln Leu Gly Lys Cys Asn Ile Ala Gly Trp Leu Leu
            435                 440                 445

Gly Asn Pro Glu Cys Asp Pro Leu Leu Pro Val Arg Ser Trp Ser Tyr
        450                 455                 460

Ile Val Glu Thr Pro Asn Ser Glu Asn Gly Ile Cys Tyr Pro Gly Asp
465                 470                 475                 480

Phe Ile Asp Tyr Glu Glu Leu Arg Glu Gln Leu Ser Ser Val Ser Ser
                485                 490                 495

Phe Glu Arg Phe Glu Ile Phe Pro Lys Glu Ser Ser Trp Pro Asn His
            500                 505                 510

Asn Thr Asn Gly Val Thr Ala Ala Cys Ser His Glu Gly Lys Ser Ser
            515                 520                 525

Phe Tyr Arg Asn Leu Leu Trp Leu Thr Glu Lys Glu Gly Ser Tyr Pro
        530                 535                 540

Lys Leu Lys Asn Ser Tyr Val Asn Lys Lys Gly Lys Glu Val Leu Val
545                 550                 555                 560
```

```
Leu Trp Gly Ile His His Pro Pro Asn Ser Lys Glu Gln Gln Asn Leu
            565                 570                 575

Tyr Gln Asn Glu Asn Ala Tyr Val Ser Val Val Thr Ser Asn Tyr Asn
        580                 585                 590

Arg Arg Phe Thr Pro Glu Ile Ala Glu Arg Pro Lys Val Arg Asp Gln
    595                 600                 605

Ala Gly Arg Met Asn Tyr Tyr Trp Thr Leu Leu Lys Pro Gly Asp Thr
610                 615                 620

Ile Ile Phe Glu Ala Asn Gly Asn Leu Ile Ala Pro Met Tyr Ala Phe
625                 630                 635                 640

Ala Leu Ser Arg Gly Phe Gly Ser Gly Ile Ile Thr Ser Asn Ala Ser
                645                 650                 655

Met His Glu Cys Asn Thr Lys Cys Gln Thr Pro Leu Gly Ala Ile Asn
            660                 665                 670

Ser Ser Leu Pro Tyr Gln Asn Ile His Pro Val Thr Ile Gly Glu Cys
        675                 680                 685

Pro Lys Tyr Val Arg Ser Ala Lys Leu Arg Met Val Thr Gly Leu Arg
    690                 695                 700

Asn Ile Pro Ser Ile Gln Ser Arg Gly Leu Phe Gly Ala Ile Ala Gly
705                 710                 715                 720

Phe Ile Glu Gly Gly Trp Thr Gly Met Ile Asp Gly Trp Tyr Gly Tyr
                725                 730                 735

His His Gln Asn Glu Gln Gly Ser Gly Tyr Ala Ala Asp Gln Lys Ser
            740                 745                 750

Thr Gln Asn Ala Ile Asn Gly Ile Thr Asn Lys Val Asn Thr Val Ile
        755                 760                 765

Glu Lys Met Asn Ile Gln Phe Thr Ala Val Gly Lys Glu Phe Asn Lys
    770                 775                 780

Leu Glu Lys Arg Met Glu Asn Leu Asn Lys Lys Val Asp Asp Gly Phe
785                 790                 795                 800

Leu Asp Ile Trp Thr Tyr Asn Ala Glu Leu Leu Val Leu Leu Glu Asn
                805                 810                 815

Glu Arg Thr Leu Asp Phe His Asp Ser Asn Val Lys Asn Leu Tyr Glu
            820                 825                 830

Lys Val Lys Ser Gln Leu Lys Asn Asn Ala Lys Glu Ile Gly Asn Gly
        835                 840                 845

Cys Phe Glu Phe Tyr His Lys Cys Asp Asn Glu Cys Met Glu Ser Val
    850                 855                 860

Arg Asn Gly Thr Tyr Asp Tyr Pro Lys Tyr Ser Glu Glu Ser Lys Leu
865                 870                 875                 880

Asn Arg Glu Lys Val Asp Gly Val Lys Leu Glu Ser Met Gly Ile Tyr
                885                 890                 895

Gln Ile Leu Ala Ile Tyr Ser Thr Val Ala Ser Ser Leu
            900                 905

<210> SEQ ID NO 2
<211> LENGTH: 917
<212> TYPE: PRT
<213> ORGANISM: Artificial sequence
<220> FEATURE:
<223> OTHER INFORMATION: synthetic

<400> SEQUENCE: 2

Asp Ile Gln Met Thr Gln Ser Pro Ala Ser Leu Ser Val Ser Val Gly
1               5                   10                  15
```

```
Glu Thr Val Thr Ile Thr Cys Arg Ala Ser Glu Asn Ile Tyr Ser Asn
             20                  25                  30

Leu Ala Trp Tyr Arg Gln Lys Gln Gly Lys Ser Pro Gln Leu Leu Val
         35                  40                  45

Phe Ala Ala Ser Asn Leu Ala Asp Gly Val Pro Ser Arg Phe Ser Gly
     50                  55                  60

Ser Gly Ser Gly Thr Gln Tyr Ser Leu Lys Ile Asn Ser Leu Gln Ser
65                  70                  75                  80

Glu Asp Phe Gly Asp Tyr Tyr Cys Gln His Phe Trp Thr Thr Pro Trp
                 85                  90                  95

Ala Phe Gly Gly Gly Thr Asn Leu Glu Ile Lys Arg Gly Gly Gly Gly
             100                 105                 110

Ser Gly Gly Gly Gly Ser Gly Gly Gly Ser Gln Ile Gln Leu Val
         115                 120                 125

Gln Ser Gly Pro Glu Leu Lys Lys Pro Gly Glu Thr Val Lys Ile Ser
     130                 135                 140

Cys Lys Ala Ser Gly Phe Thr Phe Thr Asn Tyr Gly Met Asn Trp Val
145                 150                 155                 160

Lys Gln Ala Pro Gly Lys Gly Leu Lys Trp Met Gly Trp Ile Asn Thr
                 165                 170                 175

Tyr Thr Arg Glu Pro Thr Tyr Ala Asp Asp Phe Lys Gly Arg Phe Ala
             180                 185                 190

Phe Ser Leu Glu Thr Ser Ala Ser Thr Ala Tyr Leu Gln Ile Asn Asn
         195                 200                 205

Leu Lys Asn Glu Asp Thr Ala Lys Tyr Phe Cys Ala Arg Asp Ile Thr
     210                 215                 220

Ala Val Val Pro Thr Gly Phe Asp Tyr Trp Gly Gln Gly Thr Thr Leu
225                 230                 235                 240

Thr Val Ser Ser Glu Leu Lys Thr Pro Leu Gly Asp Thr Thr His Thr
                 245                 250                 255

Glu Pro Lys Ser Cys Asp Thr Pro Pro Cys Pro Arg Cys Pro Gly
             260                 265                 270

Gly Gly Ser Ser Gly Gly Gly Ser Gly Gly Gln Pro Arg Glu Pro Gln
         275                 280                 285

Val Tyr Thr Leu Pro Pro Ser Arg Glu Glu Met Thr Lys Asn Gln Val
     290                 295                 300

Ser Leu Thr Cys Leu Val Lys Gly Phe Tyr Pro Ser Asp Ile Ala Val
305                 310                 315                 320

Glu Trp Glu Ser Ser Gly Gln Pro Glu Asn Asn Tyr Asn Thr Thr Pro
                 325                 330                 335

Pro Met Leu Asp Ser Asp Gly Ser Phe Phe Leu Tyr Ser Lys Leu Thr
             340                 345                 350

Val Asp Lys Ser Arg Trp Gln Gln Gly Asn Ile Phe Ser Cys Ser Val
         355                 360                 365

Met His Glu Ala Leu His Asn Arg Phe Thr Gln Lys Ser Leu Ser Leu
     370                 375                 380

Ser Pro Gly Lys Gly Leu Gly Leu Arg Asp Thr Ile Cys Ile Gly
385                 390                 395                 400

Tyr His Ala Asn Asn Ser Thr Asp Thr Val Asp Thr Val Leu Glu Lys
                 405                 410                 415

Asn Val Thr Val Thr His Ser Val Asn Leu Leu Glu Asp Ser His Asn
             420                 425                 430

Gly Lys Leu Cys Arg Leu Lys Gly Ile Ala Pro Leu Gln Leu Gly Lys
```

```
                435              440              445
Cys Asn Ile Ala Gly Trp Leu Leu Gly Asn Pro Glu Cys Asp Pro Leu
450              455              460

Leu Pro Val Arg Ser Trp Ser Tyr Ile Val Glu Thr Pro Asn Ser Glu
465                       470              475              480

Asn Gly Ile Cys Tyr Pro Gly Asp Phe Ile Asp Tyr Glu Glu Leu Arg
                485              490              495

Glu Gln Leu Ser Ser Val Ser Ser Phe Glu Arg Phe Glu Ile Phe Pro
             500              505              510

Lys Glu Ser Ser Trp Pro Asn His Asn Thr Asn Gly Val Thr Ala Ala
             515              520              525

Cys Ser His Glu Gly Lys Ser Ser Phe Tyr Arg Asn Leu Leu Trp Leu
530              535              540

Thr Glu Lys Glu Gly Ser Tyr Pro Lys Leu Lys Asn Ser Tyr Val Asn
545              550              555              560

Lys Lys Gly Lys Glu Val Leu Val Leu Trp Gly Ile His His Pro Pro
                565              570              575

Asn Ser Lys Glu Gln Gln Asn Leu Tyr Gln Asn Glu Asn Ala Tyr Val
             580              585              590

Ser Val Val Thr Ser Asn Tyr Asn Arg Arg Phe Thr Pro Glu Ile Ala
         595              600              605

Glu Arg Pro Lys Val Arg Asp Gln Ala Gly Arg Met Asn Tyr Tyr Trp
610              615              620

Thr Leu Leu Lys Pro Gly Asp Thr Ile Ile Phe Glu Ala Asn Gly Asn
625              630              635              640

Leu Ile Ala Pro Met Tyr Ala Phe Ala Leu Ser Arg Gly Phe Gly Ser
                645              650              655

Gly Ile Ile Thr Ser Asn Ala Ser Met His Glu Cys Asn Thr Lys Cys
             660              665              670

Gln Thr Pro Leu Gly Ala Ile Asn Ser Ser Leu Pro Tyr Gln Asn Ile
         675              680              685

His Pro Val Thr Ile Gly Glu Cys Pro Lys Tyr Val Arg Ser Ala Lys
690              695              700

Leu Arg Met Val Thr Gly Leu Arg Asn Ile Pro Ser Ile Gln Ser Arg
705              710              715              720

Gly Leu Phe Gly Ala Ile Ala Gly Phe Ile Glu Gly Gly Trp Thr Gly
                725              730              735

Met Ile Asp Gly Trp Tyr Gly Tyr His His Gln Asn Glu Gln Gly Ser
             740              745              750

Gly Tyr Ala Ala Asp Gln Lys Ser Thr Gln Asn Ala Ile Asn Gly Ile
         755              760              765

Thr Asn Lys Val Asn Thr Val Ile Glu Lys Met Asn Ile Gln Phe Thr
770              775              780

Ala Val Gly Lys Glu Phe Asn Lys Leu Glu Lys Arg Met Glu Asn Leu
785              790              795              800

Asn Lys Lys Val Asp Asp Gly Phe Leu Asp Ile Trp Thr Tyr Asn Ala
                805              810              815

Glu Leu Leu Val Leu Leu Glu Asn Glu Arg Thr Leu Asp Phe His Asp
             820              825              830

Ser Asn Val Lys Asn Leu Tyr Glu Lys Val Lys Ser Gln Leu Lys Asn
         835              840              845

Asn Ala Lys Glu Ile Gly Asn Gly Cys Phe Glu Phe Tyr His Lys Cys
850              855              860
```

Asp Asn Glu Cys Met Glu Ser Val Arg Asn Gly Thr Tyr Asp Tyr Pro
865                 870                 875                 880

Lys Tyr Ser Glu Glu Ser Lys Leu Asn Arg Glu Lys Val Asp Gly Val
            885                 890                 895

Lys Leu Glu Ser Met Gly Ile Tyr Gln Ile Leu Ala Ile Tyr Ser Thr
            900                 905                 910

Val Ala Ser Ser Leu
        915

<210> SEQ ID NO 3
<211> LENGTH: 241
<212> TYPE: PRT
<213> ORGANISM: Artificial sequence
<220> FEATURE:
<223> OTHER INFORMATION: synthetic

<400> SEQUENCE: 3

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Phe Pro Arg
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Ser Gln Ile Gln Leu Val
            115                 120                 125

Gln Ser Gly Pro Glu Leu Lys Lys Pro Gly Glu Thr Val Lys Ile Ser
130                 135                 140

Cys Lys Ala Ser Gly Tyr Thr Phe Ile Asn Tyr Gly Met Asn Trp Val
145                 150                 155                 160

Lys Gln Thr Pro Gly Lys Gly Leu Lys Trp Met Gly Trp Ile Asn Thr
                165                 170                 175

Tyr Ser Gly Glu Pro Thr Tyr Pro Asp Asp Phe Lys Gly Arg Phe Ala
            180                 185                 190

Phe Ser Leu Glu Thr Ser Ala Ser Thr Ala Tyr Leu Gln Leu Asn Asn
        195                 200                 205

Leu Lys Asn Glu Asp Met Ala Thr Tyr Phe Cys Ala Arg Gly Asp Tyr
    210                 215                 220

Tyr Gly Pro Phe Asp Asn Trp Gly Gln Gly Thr Thr Leu Thr Val Ser
225                 230                 235                 240

Ser

<210> SEQ ID NO 4
<211> LENGTH: 8
<212> TYPE: PRT
<213> ORGANISM: Artificial sequence
<220> FEATURE:
<223> OTHER INFORMATION: synthetic

<400> SEQUENCE: 4

Gln Asp Ile Asn Asn Tyr Leu Asn
1               5

<210> SEQ ID NO 5
<211> LENGTH: 11
<212> TYPE: PRT
<213> ORGANISM: Artificial sequence
<220> FEATURE:
<223> OTHER INFORMATION: synthetic

<400> SEQUENCE: 5

Leu Leu Ile Tyr Tyr Thr Ser Ser Leu His Ser
1               5                   10

<210> SEQ ID NO 6
<211> LENGTH: 9
<212> TYPE: PRT
<213> ORGANISM: Artificial sequence
<220> FEATURE:
<223> OTHER INFORMATION: synthetic

<400> SEQUENCE: 6

Gln Gln Tyr Ser Lys Phe Pro Arg Thr
1               5

<210> SEQ ID NO 7
<211> LENGTH: 10
<212> TYPE: PRT
<213> ORGANISM: Artificial sequence
<220> FEATURE:
<223> OTHER INFORMATION: synthetic

<400> SEQUENCE: 7

Gly Tyr Thr Phe Ile Asn Tyr Gly Met Asn
1               5                   10

<210> SEQ ID NO 8
<211> LENGTH: 15
<212> TYPE: PRT
<213> ORGANISM: Artificial sequence
<220> FEATURE:
<223> OTHER INFORMATION: synthetic

<400> SEQUENCE: 8

Trp Met Gly Trp Ile Asn Thr Tyr Ser Gly Glu Pro Thr Tyr Pro
1               5                   10                  15

<210> SEQ ID NO 9
<211> LENGTH: 10
<212> TYPE: PRT
<213> ORGANISM: Artificial sequence
<220> FEATURE:
<223> OTHER INFORMATION: synthetic

<400> SEQUENCE: 9

Arg Gly Asp Tyr Tyr Gly Pro Phe Asp Asn
1               5                   10

<210> SEQ ID NO 10
<211> LENGTH: 244
<212> TYPE: PRT
<213> ORGANISM: Artificial sequence
<220> FEATURE:
<223> OTHER INFORMATION: synthetic

<400> SEQUENCE: 10

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Arg Gln Lys Gln Gly Lys Ser Pro Gln Leu Leu Val
        35                  40                  45

Phe Ala Ala Ser Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Asp Tyr Tyr Cys Gln His Phe Trp Thr Thr Pro Trp
                85                  90                  95

Ala Phe Gly Gly Gly Thr Asn Leu Glu Ile Lys Arg Gly Gly Gly Gly
        100                 105                 110

Ser Gly Gly Gly Gly Ser Gly Gly Gly Ser Gln Ile Gln Leu Val
            115                 120                 125

Gln Ser Gly Pro Glu Leu Lys Lys Pro Gly Glu Thr Val Lys Ile Ser
    130                 135                 140

Cys Lys Ala Ser Gly Phe Thr Phe Thr Asn Tyr Gly Met Asn Trp Val
145                 150                 155                 160

Lys Gln Ala Pro Gly Lys Gly Leu Lys Trp Met Gly Trp Ile Asn Thr
                165                 170                 175

Tyr Thr Arg Glu Pro Thr Tyr Ala Asp Asp Phe Lys Gly Arg Phe Ala
        180                 185                 190

Phe Ser Leu Glu Thr Ser Ala Ser Thr Ala Tyr Leu Gln Ile Asn Asn
    195                 200                 205

Leu Lys Asn Glu Asp Thr Ala Lys Tyr Phe Cys Ala Arg Asp Ile Thr
210                 215                 220

Ala Val Val Pro Thr Gly Phe Asp Tyr Trp Gly Gln Gly Thr Thr Leu
225                 230                 235                 240

Thr Val Ser Ser

<210> SEQ ID NO 11
<211> LENGTH: 8
<212> TYPE: PRT
<213> ORGANISM: Artificial sequence
<220> FEATURE:
<223> OTHER INFORMATION: synthetic

<400> SEQUENCE: 11

Glu Asn Ile Tyr Ser Asn Leu Ala
1               5

<210> SEQ ID NO 12
<211> LENGTH: 11
<212> TYPE: PRT
<213> ORGANISM: Artificial sequence
<220> FEATURE:
<223> OTHER INFORMATION: synthetic

<400> SEQUENCE: 12

Leu Leu Val Phe Ala Ala Ser Asn Leu Ala Asp
1               5                   10

<210> SEQ ID NO 13
<211> LENGTH: 9
<212> TYPE: PRT
<213> ORGANISM: Artificial sequence
<220> FEATURE:
```

```
<223> OTHER INFORMATION: synthetic

<400> SEQUENCE: 13

Gln His Phe Trp Thr Thr Pro Trp Ala
1               5

<210> SEQ ID NO 14
<211> LENGTH: 8
<212> TYPE: PRT
<213> ORGANISM: Artificial sequence
<220> FEATURE:
<223> OTHER INFORMATION: synthetic

<400> SEQUENCE: 14

Gly Phe Thr Phe Thr Asn Tyr Gly
1               5

<210> SEQ ID NO 15
<211> LENGTH: 14
<212> TYPE: PRT
<213> ORGANISM: Artificial sequence
<220> FEATURE:
<223> OTHER INFORMATION: synthetic

<400> SEQUENCE: 15

Trp Met Gly Trp Ile Asn Thr Tyr Thr Arg Glu Pro Thr Tyr
1               5                   10

<210> SEQ ID NO 16
<211> LENGTH: 14
<212> TYPE: PRT
<213> ORGANISM: Artificial sequence
<220> FEATURE:
<223> OTHER INFORMATION: synthetic

<400> SEQUENCE: 16

Ala Arg Asp Ile Thr Ala Val Val Pro Thr Gly Phe Asp Tyr
1               5                   10

<210> SEQ ID NO 17
<211> LENGTH: 96
<212> TYPE: PRT
<213> ORGANISM: Artificial sequence
<220> FEATURE:
<223> OTHER INFORMATION: synthetic

<400> SEQUENCE: 17

Gly Asp Thr Arg Pro Arg Phe Leu Trp Gln Leu Lys Phe Glu Cys His
1               5                   10                  15

Phe Phe Asn Gly Thr Glu Arg Val Arg Leu Leu Glu Arg Cys Ile Tyr
                20                  25                  30

Asn Gln Glu Glu Ser Val Arg Phe Asp Ser Asp Val Gly Glu Tyr Arg
            35                  40                  45

Ala Val Thr Glu Leu Gly Arg Pro Asp Ala Glu Tyr Trp Asn Ser Gln
        50                  55                  60

Lys Asp Leu Leu Glu Gln Arg Arg Ala Ala Val Asp Thr Tyr Cys Arg
65                  70                  75                  80

His Asn Tyr Gly Val Gly Glu Ser Phe Thr Val Gln Arg Arg Val Glu
                85                  90                  95

<210> SEQ ID NO 18
<211> LENGTH: 96
<212> TYPE: PRT
<213> ORGANISM: Artificial sequence
```

<220> FEATURE:
<223> OTHER INFORMATION: synthetic

<400> SEQUENCE: 18

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Ala Ala Val Asp Thr Tyr Cys Arg
65                  70                  75                  80

His Asn Tyr Gly Val Gly Glu Ser Phe Thr Val Gln Arg Val Tyr
                85                  90                  95

<210> SEQ ID NO 19
<211> LENGTH: 96
<212> TYPE: PRT
<213> ORGANISM: Artificial sequence
<220> FEATURE:
<223> OTHER INFORMATION: synthetic

<400> SEQUENCE: 19

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
        35                  40                  45

Ala Val Thr Glu Leu Gly Arg Pro Asp Glu Glu Tyr Trp Asn Ser Gln
    50                  55                  60

Lys Asp Phe Leu Glu Asp Arg Arg Ala Ala Val Asp Thr Tyr Cys Arg
65                  70                  75                  80

His Asn Tyr Gly Val Gly Glu Ser Phe Thr Val Gln Arg Arg Val His
                85                  90                  95

<210> SEQ ID NO 20
<211> LENGTH: 96
<212> TYPE: PRT
<213> ORGANISM: Artificial sequence
<220> FEATURE:
<223> OTHER INFORMATION: synthetic

<400> SEQUENCE: 20

Gly Asp Thr Arg Pro Arg Phe Leu Glu Tyr Ser Thr Ser Glu Cys His
1               5                   10                  15

Phe Phe Asn Gly Thr Glu Arg Val Arg Phe Leu Asp Arg Tyr Phe Tyr
            20                  25                  30

Asn Gln Glu Glu Tyr Val Arg Phe Asp Ser Asp Val Gly Glu Phe Arg
        35                  40                  45

Ala Val Thr Glu Leu Gly Arg Pro Asp Glu Glu Tyr Trp Asn Ser Gln
    50                  55                  60

Lys Asp Phe Leu Glu Asp Arg Arg Ala Ala Val Asp Thr Tyr Cys Arg
65                  70                  75                  80

His Asn Tyr Gly Val Val Glu Ser Phe Thr Val Gln Arg Arg Val His
                85                  90                  95

<210> SEQ ID NO 21
<211> LENGTH: 94
<212> TYPE: PRT
<213> ORGANISM: Artificial sequence
<220> FEATURE:
<223> OTHER INFORMATION: synthetic

<400> SEQUENCE: 21

Arg Ala Thr Pro Glu Asn Tyr Leu Phe Gln Gly Arg Gln Glu Cys Tyr
1               5                   10                  15

Ala Phe Asn Gly Thr Gln Arg Phe Leu Glu Arg Tyr Ile Tyr Asn Arg
            20                  25                  30

Glu Glu Phe Val Arg Phe Asp Ser Asp Val Gly Asp Phe Arg Ala Val
        35                  40                  45

Thr Glu Leu Gly Arg Pro Asp Glu Glu Tyr Trp Asn Ser Gln Lys Asp
    50                  55                  60

Ile Leu Glu Glu Glu Arg Ala Val Pro Asp Arg Met Cys Arg His Asn
65                  70                  75                  80

Tyr Glu Leu Gly Gly Phe Met Thr Leu Gln Arg Arg Val Gln
                85                  90

<210> SEQ ID NO 22
<211> LENGTH: 94
<212> TYPE: PRT
<213> ORGANISM: Artificial sequence
<220> FEATURE:
<223> OTHER INFORMATION: synthetic

<400> SEQUENCE: 22

Arg Ala Thr Pro Glu Asn Tyr Leu Phe Gln Gly Arg Gln Glu Cys Tyr
1               5                   10                  15

Ala Phe Asn Gly Thr Gln Arg Phe Leu Glu Arg Tyr Ile Tyr Asn Arg
            20                  25                  30

Glu Glu Phe Ala Arg Phe Asp Ser Asp Val Gly Glu Phe Arg Ala Val
        35                  40                  45

Thr Glu Leu Gly Arg Pro Ala Ala Glu Tyr Trp Asn Ser Gln Lys Asp
    50                  55                  60

Ile Leu Glu Glu Lys Arg Ala Val Pro Asp Arg Met Cys Arg His Asn
65                  70                  75                  80

Tyr Glu Leu Gly Gly Phe Met Thr Leu Gln Arg Arg Val Gln
                85                  90

<210> SEQ ID NO 23
<211> LENGTH: 96
<212> TYPE: PRT
<213> ORGANISM: Artificial sequence
<220> FEATURE:
<223> OTHER INFORMATION: synthetic

<400> SEQUENCE: 23

Arg Asp Ser Pro Glu Asp Phe Val Tyr Gln Phe Lys Gly Met Cys Tyr
1               5                   10                  15

Phe Thr Asn Gly Thr Glu Arg Val Arg Leu Val Ser Arg Ser Ile Tyr
            20                  25                  30

Asn Arg Glu Glu Ile Val Arg Phe Asp Ser Asp Val Gly Glu Phe Arg
        35                  40                  45

Ala Val Thr Leu Leu Gly Leu Pro Ala Ala Glu Tyr Trp Asn Ser Gln
    50                  55                  60

Lys Asp Ile Leu Glu Arg Lys Arg Ala Ala Val Asp Arg Val Cys Arg

```
                65                  70                  75                  80
His Asn Tyr Gln Leu Glu Leu Arg Thr Thr Leu Gln Arg Arg Val Glu
                    85                  90                  95
```

<210> SEQ ID NO 24
<211> LENGTH: 96
<212> TYPE: PRT
<213> ORGANISM: Artificial sequence
<220> FEATURE:
<223> OTHER INFORMATION: synthetic

<400> SEQUENCE: 24

```
Arg Asp Ser Pro Glu Asp Phe Val Tyr Gln Phe Lys Gly Met Cys Tyr
1               5                   10                  15

Phe Thr Asn Gly Thr Glu Arg Val Arg Leu Val Thr Arg Tyr Ile Tyr
                20                  25                  30

Asn Arg Glu Glu Tyr Ala Arg Phe Asp Ser Asp Val Gly Val Tyr Arg
            35                  40                  45

Ala Val Thr Pro Leu Gly Pro Pro Ala Ala Glu Tyr Trp Asn Ser Gln
        50                  55                  60

Lys Glu Val Leu Glu Arg Thr Arg Ala Glu Leu Asp Thr Val Cys Arg
65                  70                  75                  80

His Asn Tyr Gln Leu Glu Leu Arg Thr Thr Leu Gln Arg Arg Val Glu
                85                  90                  95
```

<210> SEQ ID NO 25
<211> LENGTH: 94
<212> TYPE: PRT
<213> ORGANISM: Artificial sequence
<220> FEATURE:
<223> OTHER INFORMATION: synthetic

<400> SEQUENCE: 25

```
Ser Arg Pro Trp Phe Leu Glu Tyr Cys Lys Ser Glu Cys His Phe Tyr
1               5                   10                  15

Asn Gly Thr Gln Arg Val Arg Leu Leu Val Arg Tyr Phe Tyr Asn Leu
                20                  25                  30

Glu Glu Asn Leu Arg Phe Asp Ser Asp Val Gly Glu Phe Arg Ala Val
            35                  40                  45

Thr Glu Leu Gly Arg Pro Asp Ala Glu Asn Trp Asn Ser Gln Pro Glu
        50                  55                  60

Phe Leu Glu Gln Lys Arg Ala Glu Val Asp Thr Val Cys Arg His Asn
65                  70                  75                  80

Tyr Glu Ile Phe Asp Asn Phe Leu Val Pro Arg Arg Val Glu
                85                  90
```

<210> SEQ ID NO 26
<211> LENGTH: 51
<212> TYPE: DNA
<213> ORGANISM: Artificial sequence
<220> FEATURE:
<223> OTHER INFORMATION: synthetic

<400> SEQUENCE: 26
ggcggaggtg gctctggcgg tggcggatcg cagatccagt tggtgcagtc t         51

<210> SEQ ID NO 27
<211> LENGTH: 35
<212> TYPE: DNA
<213> ORGANISM: Artificial sequence
<220> FEATURE:

-continued

<223> OTHER INFORMATION: synthetic

<400> SEQUENCE: 27
gacgtacgac tcacctgagg agactgtgag agtgg 35